（12）United States Patent
Barnes et al.

(10) Patent No.: US 11,154,613 B2
(45) Date of Patent: Oct. 26, 2021

(54) HCV VACCINES

(71) Applicant: Oxford University Innovation Ltd., Oxford (GB)

(72) Inventors: Eleanor Barnes, Oxford (GB); Annette Von Delft, Oxford (GB); Jose Lorenco, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 16/087,352

(22) PCT Filed: Mar. 24, 2017

(86) PCT No.: PCT/GB2017/050840
§ 371 (c)(1),
(2) Date: Sep. 21, 2018

(87) PCT Pub. No.: WO2017/163083
PCT Pub. Date: Sep. 28, 2017

(65) Prior Publication Data
US 2021/0138063 A1    May 13, 2021

(30) Foreign Application Priority Data
Mar. 24, 2016  (GB) .................... 1605099

(51) Int. Cl.
*A61K 39/29* (2006.01)
*C07K 14/005* (2006.01)
*A61K 39/00* (2006.01)

(52) U.S. Cl.
CPC ............ *A61K 39/29* (2013.01); *C07K 14/005* (2013.01); *A61K 2039/53* (2013.01); *A61K 2039/70* (2013.01); *C12N 2770/24222* (2013.01); *C12N 2770/24234* (2013.01)

(58) Field of Classification Search
None
See application file for complete search history.

(56) References Cited

FOREIGN PATENT DOCUMENTS

| WO | WO2001021189 A1 | 3/2001 |
| WO | WO2005118626 A2 | 12/2005 |
| WO | WO2010011870 A2 | 1/2010 |

OTHER PUBLICATIONS

Chen et al., "Immunization with a synthetic multiepitope antigen induces humoral and cellular immune responses to hepatitis C virus in mice," Mar. 2007, Viral Immunology, 20(1): 170-179.
Partial International Search Report and Written Opinion dated Jun. 19, 2017, in International Application No. PCT/GB2017/050840, 14 pages.
Yan et al., "Induction of strong cytotoxic T-lymphocyte responses to hepatitis C virus with recombinant poly-epitope in BALB/c mice," Apr. 2006, Viral Immunology, 19(1): 64-73.
European Search Report dated Aug. 31, 2020 in European application No. 17715523.1, Barnes et al., a corresponding foreign application of U.S. Appl. No. 16/087,352, 13 pages.
Klade, "Hepatitis C virus-specific T cell responses against conserved regions on recovered patients," May 2009. Vaccine, 27(23): 3099-3108.
Latimer, "Strong HCV NS3/4a, NS4b, NS5a, NS5b-specific cellular immune responses induced in Rhesus macaques by a novel HCV genotype 1a/1b consensus DNA vaccine," Aug. 2014. Human Vaccines & Immunotherapeutics, 10(8): 2357-2365.
Von Delft, "The generation of a simian adenoviral vectored HCV vaccine encoding genetically conserved gene segments to target multiple HCV genotypes," Jan. 2018. Vaccine, 36(2):313-321.

*Primary Examiner* — Stacy B Chen
(74) *Attorney, Agent, or Firm* — Lee & Hayes, P.C.

(57) ABSTRACT

The invention concerns a fusion polypeptide comprising a plurality of conserved peptide sequences, or variants thereof, wherein at least one of the conserved sequences is conserved across: i) HCV genotypes 1a and 1b; ii) HCV genotypes 1 and 3; or iii) HCV genotypes 1 to 6; and wherein at least one of the conserved peptide sequences comprises at least part of a sequence of a non-structural protein of the HCV genotypes; including associated nucleic acid and vector sequences, and use in methods of treatment or prophylaxis, such as vaccination.

10 Claims, 15 Drawing Sheets

Figure 1:
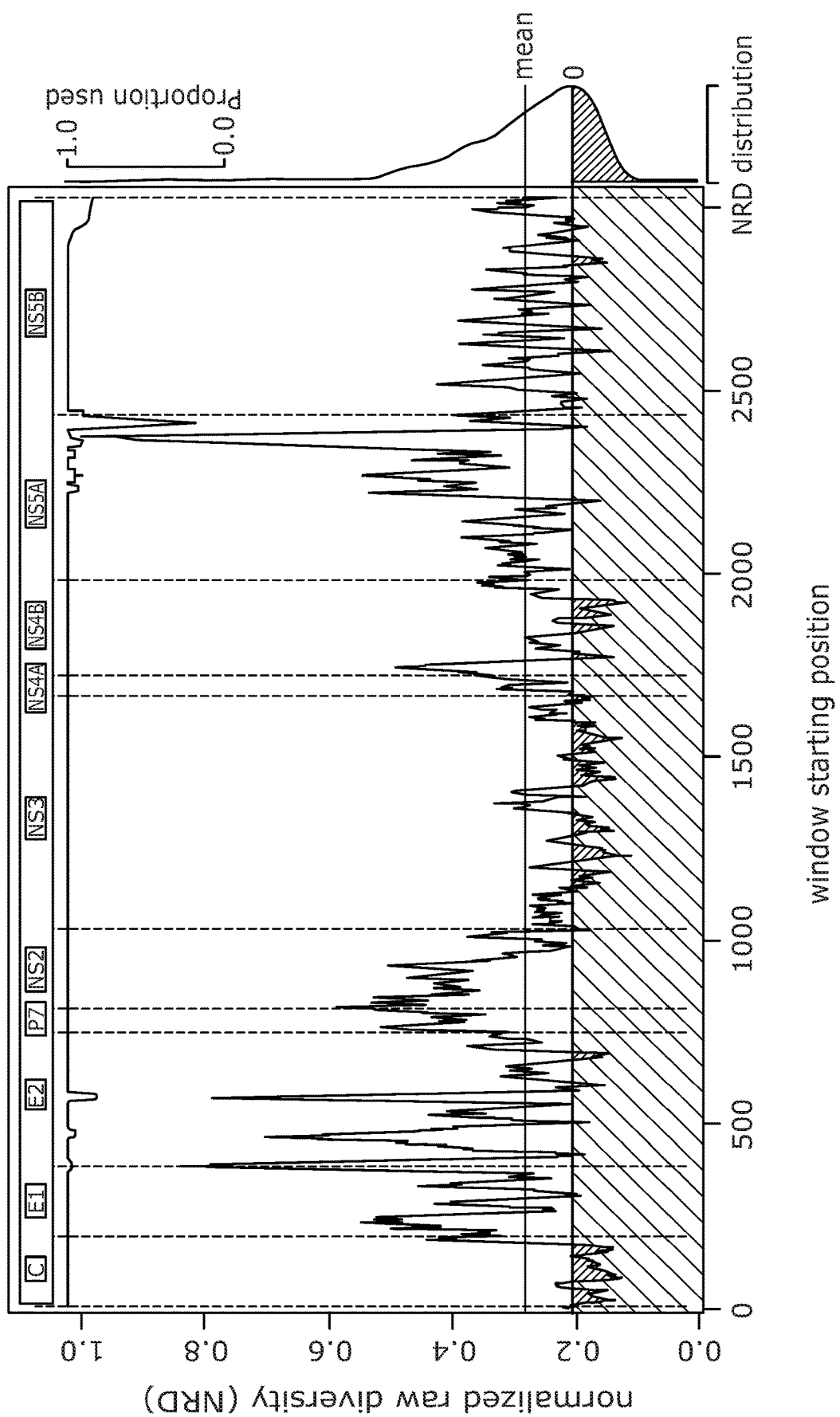
Figure 2A:
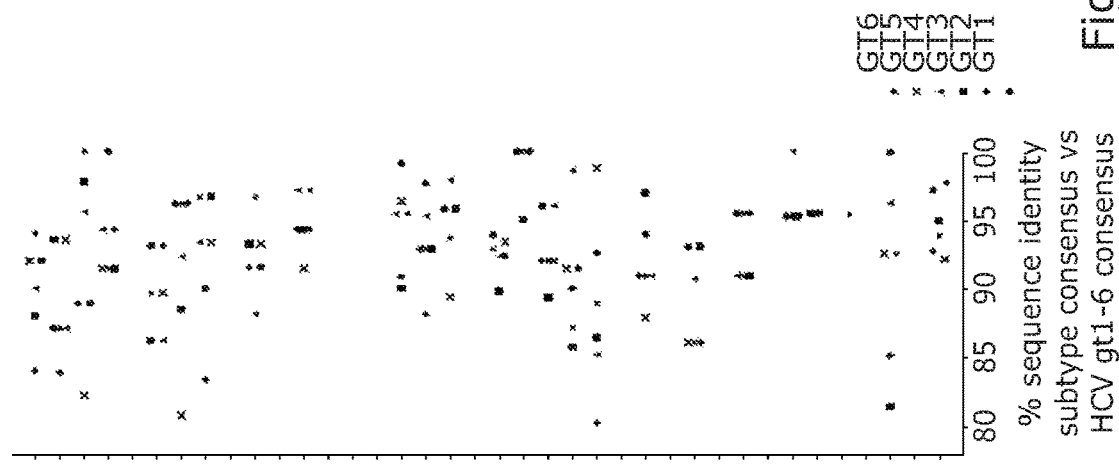
Figure 2A:
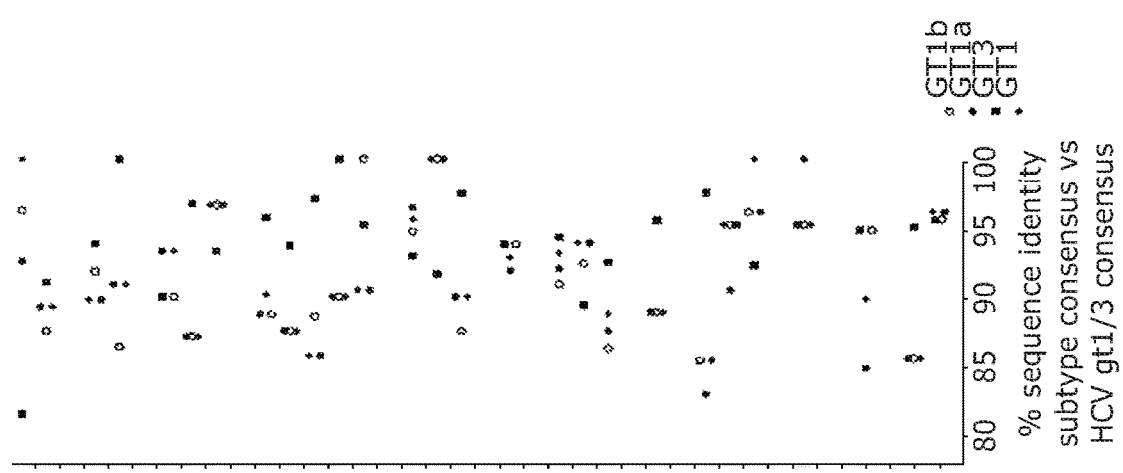
Figure 2A:
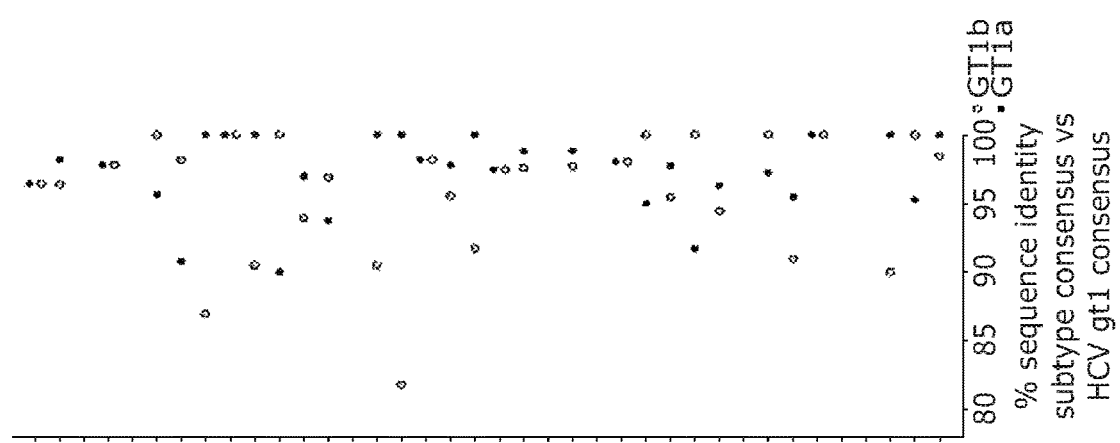
Figure 2B:
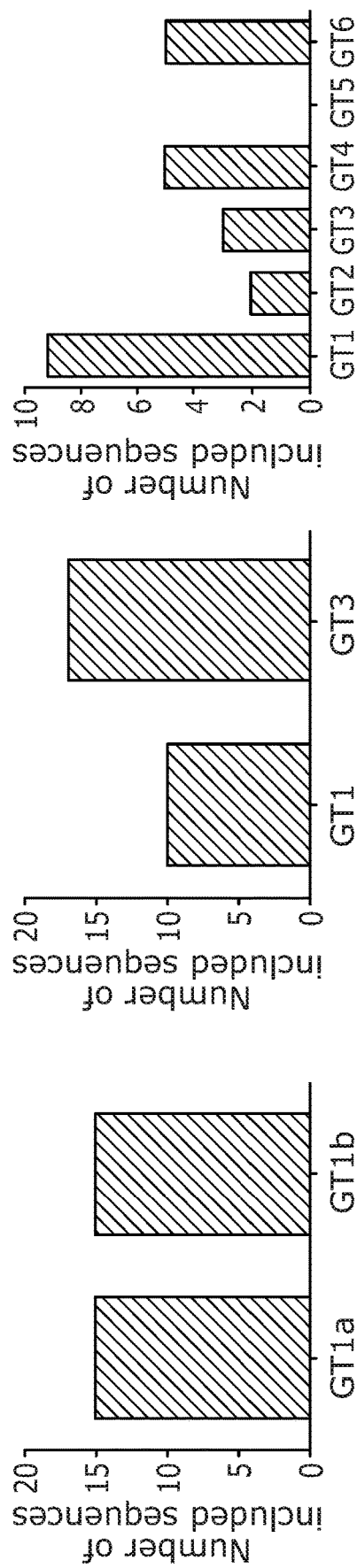

Specification includes a Sequence Listing.

Figure 1 (continued)

Figure 1 (continued)

HCV VACCINES

CROSS REFERENCE TO RELATED APPLICATIONS

This application is a U.S. National Phase Application of International Application No. PCT/GB2017/050840, filed Mar. 24, 2017, which claims the benefit of priority of GB Patent Application No. 1605099.9, filed on Mar. 24, 2016, both of which are hereby incorporated by reference in their entirety.

This invention relates to polypeptides, particularly immunogenic polypeptides, and associated viral vectors for use in a vaccine against HCV infection.

With 3-4 million new infections occurring annually, hepatitis C virus (HCV) is a major global health problem. There is increasing evidence to suggest that HCV will be highly amenable to a vaccine approach, and despite advances in treatment, a vaccine remains the most cost-effective and realistic means to significantly reduce the worldwide mortality and morbidity associated with persistent HCV infection. Currently, there is no licensed vaccine for HCV and treatment is based on pegylated-interferon-α (IFNα) and the nucleoside analogue ribavirin. This is expensive, relatively toxic, prolonged (24-48 weeks) and leads to a sustained virological response (SVR) in only 50-60% of patients, depending on the infecting genotype.

The characteristic of HCV that will offer the biggest problem for vaccine design is its viral variability. With sequence diversity believed to be 10 times that of human immunodeficiency virus (HIV), HCV strains are classified into 7 genotypes (numbered 1-7), which differ at 31-34% of their nucleotide positions, and which can be further divided into over 100 subtypes. This diversity is largely due to a lack of proof-reading capacity of the viral RNA-dependent polymerase (NS5b) used by HCV during replication; therefore, HCV exists within a host as a constantly evolving population of closely related but diverse quasispecies.

Attempts are being made to develop vaccines that are based on conserved outer surface features, such as the envelope glycoproteins E1 and E2, which are believed to be essential for the infection of liver cells. Alternative strategies have been proposed, which differ from a conventional vaccine by seeking to induce a T cell immune response using viral vectors to express large parts of HCV in a cell for MHC presentation. Synthetic HCV peptides have been used to induce T-cell immunity through direct presentation on antigen-presenting cells. However, peptide vaccines are HLA-specific and target only a selected subset of epitope sequences within HCV, limiting their breadth and coverage within the population.

Plasmids encoding HCV NS3/4a (ChronVac-c) or core/E1/E2 (CICGB-230) have shown some efficacy as potential therapeutic vaccines for HCV, but there is no published data on their effectiveness as prophylactic vaccines.

Genotypes 1a and 1b account for over 60% of chronic HCV infections worldwide, and much vaccine development to date has concentrated on raising an immune response to these genotypes due to their prevalence. However, a need exists to provide effective pan-genotypic HCV T cell vaccine in humans, which can provide protection against a larger range of HCV genotypes.

Therefore, an aim of the present invention is to provide an improved vaccine for HCV infection.

According to a first aspect of the invention, there is provided a polypeptide comprising a plurality of conserved peptide sequences, or variants thereof, wherein at least one of the conserved sequences is conserved across:
  i) HCV genotypes 1a and 1b;
  ii) HCV genotypes 1 and 3; or
  iii) HCV genotypes 1 to 6; and
  wherein at least one of the conserved peptide sequences comprises at least part of a sequence of a non-structural protein of the HCV genotypes.

The invention advantageously provides a novel alternative and safer approach to vaccination whereby T cells can be induced to the relatively conserved internal (non-structural) antigens of the virion. The use of specially selected conserved viral segments from the non-structural proteins can provide protection against multiple or all genotypes.

In one embodiment, the polypeptide is a fusion polypeptide. The polypeptide may not be a wild-type polypeptide. The polypeptide may be synthetic/artificial, for example, the polypeptide may not exist in nature. In one embodiment, the polypeptide may not comprise a complete gene sequence. The polypeptide may consist essentially of conserved peptide sequences. In one embodiment, the polypeptide is a recombinant polypeptide, such as a recombinant fusion polypeptide.

The term "fusion polypeptide" used herein is understood to mean a polypeptide comprising a combination of sequences from different gene products (for example different HCV non-structural proteins) or combinations of sequences from the same gene product (for example a single HCV non-structural protein), wherein the sequences are from distinct/separate regions of the wild-type gene product. For example the fusion polypeptide may comprise combinations of sequences which are normally separated by other sequence segments in wild-type, and the separating sequence(s) have been removed.

The term "conserved peptide sequence" or "conserved segment" used herein is defined as a sequence that is found in more than one genotype or within variant populations of the same genotype, whereby the sequence is identical or highly similar between the genotypes or variants within a genotype. Conserved peptide sequences may be identified using an algorithm which uses a sliding window-based method. In one embodiment, a conserved segment (or otherwise termed conserved peptide sequence) is where the homology of any window of 20 amino acids is at least 90% in an alignment of amino acid sequences. In another embodiment, a conserved segment is where the homology of any window of 20 amino acids is at least 91% in an alignment of amino acid sequences. In another embodiment, a conserved segment is where the homology of any window of 20 amino acids is at least 92% in an alignment of amino acid sequences. In another embodiment, a conserved segment is where the homology of any window of 20 amino acids is at least 93% in an alignment of amino acid sequences. In another embodiment, a conserved segment is where the homology of any window of 20 amino acids is at least 94% in an alignment of amino acid sequences. In another embodiment, a conserved segment is where the homology of any window of 20 amino acids is at least 95% in an alignment of amino acid sequences. In another embodiment, a conserved segment is where the homology of any window of 20 amino acids is at least 98% in an alignment of amino acid sequences. In another embodiment, a conserved segment is where the homology of any window of 20 amino acids is at least 99% in an alignment of amino acid sequences. The skilled person will understand that the 20 amino acid window uses an average homology/identity across the 20 amino acid window. Therefore, it is possible that a sequence of less than 20 amino acids may be identified as a conserved peptide sequence within the above definition.

The plurality of conserved peptide sequences may comprise 5 or more conserved peptide sequences. In another embodiment, the plurality of conserved peptide sequences may comprise 6 or more conserved peptide sequences. In another embodiment, the plurality of conserved peptide sequences may comprise 7 or more conserved peptide sequences. In another embodiment, the plurality of conserved peptide sequences may comprise 8 or more conserved peptide sequences. In another embodiment, the plurality of conserved peptide sequences may comprise 9 or more conserved peptide sequences. The plurality of conserved sequences may comprise 10 or more conserved peptide sequences. In another embodiment, the plurality of conserved peptide sequences may comprise 11 or more conserved peptide sequences. The plurality of conserved peptide sequences may comprise 15 or more conserved peptide sequences. In another embodiment, the plurality of conserved peptide sequences may comprise 20 or more conserved peptide sequences. In another embodiment, the plurality of conserved peptide sequences may comprise 30 or more conserved peptide sequences. In one embodiment, the plurality of conserved peptide sequences consists of about 11 conserved peptide sequences. In one embodiment, the plurality of conserved peptide sequences consists of about 12 conserved peptide sequences. In one embodiment, the plurality of conserved peptide sequences consists of about 24 conserved peptide sequences. In one embodiment, the plurality of conserved peptide sequences consists of about 27 conserved peptide sequences. In one embodiment, the plurality of conserved peptide sequences consists of about 30 conserved peptide sequences.

In one embodiment at least one conserved peptide sequence is conserved across HCV genotypes 1a and 1b. In one embodiment at least two conserved peptide sequences are conserved across HCV genotypes 1a and 1b. In another embodiment at least three conserved peptide sequences are conserved across HCV genotypes 1a and 1b. In another embodiment at least four conserved peptide sequences are conserved across HCV genotypes 1a and 1b. In another embodiment at least five conserved peptide sequences are conserved across HCV genotypes 1a and 1b. In another embodiment at least six conserved peptide sequences are conserved across HCV genotypes 1a and 1b. In another embodiment at least 7 conserved peptide sequences are conserved across HCV genotypes 1a and 1b. In another embodiment at least 8 conserved peptide sequences are conserved across HCV genotypes 1a and 1b. In another embodiment at least 9 conserved peptide sequences are conserved across HCV genotypes 1a and 1b. In another embodiment at least 10 conserved peptide sequences are conserved across HCV genotypes 1a and 1b. In another embodiment at least 11 conserved peptide sequences are conserved across HCV genotypes 1a and 1b. In another embodiment at least 12 conserved peptide sequences are conserved across HCV genotypes 1a and 1b. In another embodiment at least 20 conserved peptide sequences are conserved across HCV genotypes 1a and 1b. In another embodiment at least 25 conserved peptide sequences are conserved across HCV genotypes 1a and 1b. In another embodiment at least 27 conserved peptide sequences are conserved across HCV genotypes 1a and 1b. In another embodiment at least 30 conserved peptide sequences are conserved across HCV genotypes 1a and 1b.

In one embodiment at least one conserved peptide sequence is conserved across HCV genotypes 1 and 3. In one embodiment at least two conserved peptide sequences are conserved across HCV genotypes 1 and 3. In another embodiment at least three conserved peptide sequences are conserved across HCV genotypes 1 and 3. In another embodiment at least four conserved peptide sequences are conserved across HCV genotypes 1 and 3. In another embodiment at least five conserved peptide sequences are conserved across HCV genotypes 1 and 3. In another embodiment at least six conserved peptide sequences are conserved across HCV genotypes 1 and 3. In another embodiment at least 7 conserved peptide sequences are conserved across HCV genotypes 1 and 3. In another embodiment at least 8 conserved peptide sequences are conserved across HCV genotypes 1 and 3. In another embodiment at least 9 conserved peptide sequences are conserved across HCV genotypes 1 and 3. In another embodiment at least 10 conserved peptide sequences are conserved across HCV genotypes 1 and 3. In another embodiment at least 11 conserved peptide sequences are conserved across HCV genotypes 1 and 3. In another embodiment at least 12 conserved peptide sequences are conserved across HCV genotypes 1 and 3. In another embodiment at least 20 conserved peptide sequences are conserved across HCV genotypes 1 and 3. In another embodiment at least 25 conserved peptide sequences are conserved across HCV genotypes 1 and 3. In another embodiment at least 27 conserved peptide sequences are conserved across HCV genotypes 1 and 3. In another embodiment at least 30 conserved peptide sequences are conserved across HCV genotypes 1 and 3.

In one embodiment at least one conserved peptide sequence is conserved across all of HCV genotypes 1 to 6. In one embodiment at least two conserved peptide sequences are conserved across all of HCV genotypes 1 to 6. In another embodiment at least three conserved peptide sequences are conserved across all of HCV genotypes 1 to 6. In another embodiment at least four conserved peptide sequences are conserved across all of HCV genotypes 1 to 6. In another embodiment at least five conserved peptide sequences are conserved across all of HCV genotypes 1 to 6. In another embodiment at least six conserved peptide sequences are conserved across all of HCV genotypes 1 to 6. In another embodiment at least 7 conserved peptide sequences are conserved across all of HCV genotypes 1 to 6. In another embodiment at least 8 conserved peptide sequences are conserved across all of HCV genotypes 1 to 6. In another embodiment at least 9 conserved peptide sequences are conserved across all of HCV genotypes 1 to 6. In another embodiment at least 10 conserved peptide sequences are conserved across all of HCV genotypes 1 to 6. In another embodiment at least 11 conserved peptide sequences are conserved across all of HCV genotypes 1 to 6. In another embodiment at least 12 conserved peptide sequences are conserved across all of HCV genotypes 1 to 6. In another embodiment at least 20 conserved peptide sequences are conserved across all of HCV genotypes 1 to 6. In another embodiment at least 25 conserved peptide sequences are conserved across all of HCV genotypes 1 to 6. In another embodiment at least 27 conserved peptide sequences are conserved across all of HCV genotypes 1 to 6. In another embodiment at least 30 conserved peptide sequences are conserved across all of HCV genotypes 1 to 6.

The plurality of conserved peptide sequences may be derived from distinct regions of sequence relative to each other (i.e. not-naturally concurrent). For example, in the wild-type genotype the conserved sequences may be separated in the wild-type genotypes by variable/non-conserved sequences. The plurality of conserved peptide sequences may not, or may not significantly, overlap with each other. Two or more, or all, of the plurality of conserved peptide sequences may be directly joined together in the polypeptide, for example not comprising any non-conserved/variable residues there between. The polypeptide sequence may not be found in nature. The polypeptide may not comprise non-conserved sequences or residues. The conserved peptide sequences may not be distanced apart by more than 1, 2, 3, 4, or 5 residues in the polypeptide sequence, for example in embodiments where there are linker/junction residues between the conserved peptide sequences. Alternatively, the conserved peptide sequences may not be distanced apart by more than 6, 7, 8, 9, or 10 residues in the polypeptide sequence, for example in embodiments where there are linker/junction residues between the conserved peptide sequences. The polypeptide may not comprise non-conserved sequences longer than 2, 3, 4, 5, 6, 7, 8, 9, or 10 amino acids.

In one embodiment, linker residues may be provided between one or more, or all, conserved peptide sequences (e.g. providing junctions between the conserved peptide sequences in the polypeptide). The linker residues may comprise random amino acid sequences, or amino-acids that have been selected to be non-immunogenic based on epitope prediction computer programs or experiments in animal models. For example, a linker may not be considered if it is predicted or known to be an epitope (i.e. in order to avoid an immune response to epitopes, e.g. artificial epitopes, not found in HCV. The linker may be flexible. The linker may comprise or consist of K, G, P or S amino acid residues, or combinations thereof. In one embodiment, the linker may comprise or consist of G and/or P amino acid residues. The linker residues may be between 1 and 10 amino acids in length. In another embodiment, the linker residues may be between 2 and 8 residues in length. In another embodiment, the linker residues may be between 1 and 6 residues in length. The conserved peptide sequences may be distanced apart by between 1 and 10 residues in the polypeptide sequence, for example in embodiments where there are linker/junction residues between the conserved peptide sequences.

In one embodiment, the polypeptide may consist essentially of conserved peptide sequences and one or more linkers, optionally wherein the one or more linkers are disposed between adjacent conserved peptide sequence.

The conserved peptide sequences may be selected from any of the group comprising SEQ ID NO: 1 to 117; variants thereof or combinations thereof. In another embodiment, the conserved peptide sequences may be selected from any of the group comprising SEQ ID NO: 1 to 38; variants thereof or combinations thereof. In another embodiment, the conserved peptide sequences may be selected from any of the group comprising SEQ ID NO: 1 to 6; 7 or 8; 9; 10 or 11; 12; 13 or 14; 15 or 16; 17; 18 or 19; 20; 21 or 22; 23 to 26; 27 or 28; 29 to 34; 35 or 36; 37; and 38; variants thereof or combinations thereof.

In another embodiment, the conserved peptide sequences may be selected from any of the group comprising SEQ ID NO: 1; 7 or 8; 13 or 14; 15 or 16; 17; 18 or 19; 20; 23; 33; 35 or 36; and 37; variants thereof or combinations thereof.

In another embodiment, the conserved peptide sequences may be selected from any of the group comprising SEQ ID NO: 39 or 40; variants thereof or combinations thereof. In another embodiment, the conserved peptide sequences may be selected from any of the group comprising SEQ ID NO: 39 or 40; 41 or 42; 43 to 47; 48 or 49; 50 or 51; 52 or 53; 54 or 55; 56 or 57; 58 or 59; 60; 61 or 62; 63; 64; 65 or 66; 67 or 68; 69 or 70; 71; 72; 73 or 74; 75; 76 or 77; 78 or 79; and 80; variants thereof or combinations thereof.

In another embodiment, the conserved peptide sequences may be selected from any of the group comprising SEQ ID NO: 39 or 40; 47; 48 or 49; 50 or 51; 52 or 53; 54 or 55; 56 or 57; 61 or 62; 69 or 70; 76 or 77; and 78 or 79; variants thereof or combinations thereof.

In another embodiment, the conserved peptide sequences may be selected from any of the group comprising SEQ ID NO: 44; and 81-117; variants thereof or combinations thereof.

In another embodiment, the conserved peptide sequences may be selected from any of the group comprising SEQ ID NO: 44; 81 or 82; 83-85; 86 or 87; 88 or 89; 90 or 91; 92 or 93; 94 or 95; 96; 97 or 98; 99 or 100; 101 or 102; 103 or 104; 105; 106 or 107; 108; 109; 110 or 111; 112; 113; 114 or 115; and 116 or 117; variants thereof or combinations thereof.

In another embodiment, the conserved peptide sequences may be selected from any of the group comprising SEQ ID NO: 81 or 82; 85; 86 or 87; 90 or 91; 92 or 93; 94 or 95; 97 or 98; 99 or 100; 101 or 102; 103 or 104; 106 or 107; and 116 or 117; variants thereof or combinations thereof.

In another embodiment, the conserved peptide sequences may be selected from any of the group comprising SEQ ID NOs: 126 to 149; variants thereof or combinations thereof.

In another embodiment, the conserved peptide sequences may be selected from any of the group comprising SEQ ID NOs: 150 to 193; variants thereof or combinations thereof.

Some or all of the conserved peptide sequences may be derived from non-structural HCV proteins (i.e. comprising a sequence identical to, or substantially similar to a sequence of a non-structural HCV protein). The non-structural proteins may comprise any of NS2, NS3, NS4A, NS4B, NS5A, and NS5B; or combinations thereof. In another embodiment, the non-structural proteins may comprise any of NS3, NS4B, and NS5B; or combinations thereof. One or more of the conserved peptide sequences may also be derived from the HCV core protein (i.e. comprising a sequence identical to, or substantially similar to a sequence of the core HCV protein). One or more of the conserved peptide sequences may also be derived from the HCV E1 and E2 protein. For example, comprising a sequence identical to, or substantially similar to a sequence of the E1 and, or E2 HCV protein or fragments thereof. Fragments may be at least the minimum number of residues for specific T cell recognition.

The polypeptide may comprise or consist of the sequence of SEQ ID NO: 118; or variants thereof. In one embodiment, the polypeptide may comprise or consist of the sequence of SEQ ID NO: 119; or variants thereof. In another embodiment, the polypeptide may comprise or consist of the sequence of SEQ ID NO: 120; or variants thereof. In another embodiment, the polypeptide may comprise or consist of the sequence of SEQ ID NO: 121 or variants thereof. In another embodiment, the polypeptide may comprise or consist of the sequence of SEQ ID NO: 122; or variants thereof. In another embodiment, the polypeptide may comprise or consist of the sequence of SEQ ID NO: 123; or variants thereof. In another embodiment, the polypeptide may comprise or consist of the sequence of SEQ ID NO: 124; or variants thereof. In another embodiment, the polypeptide may comprise or consist of the sequence of SEQ ID NO: 125; or variants thereof.

The polypeptide may comprise or consist of the sequence of SEQ ID NO: 118 without the TPA peptide adjuvant, or with an alternative peptide adjuvant such as the shark invariant chain; or variants thereof. In one embodiment, the polypeptide may comprise or consist of the sequence of SEQ ID NO: 119 without the TPA peptide adjuvant, or with an alternative peptide adjuvant such as the shark invariant chain; or variants thereof. In another embodiment, the polypeptide may comprise or consist of the sequence of SEQ ID NO: 120 without the TPA peptide adjuvant, or with an alternative peptide adjuvant such as the shark invariant chain; or variants thereof. In another embodiment, the polypeptide may comprise or consist of the sequence of SEQ ID NO: 121 without the TPA peptide adjuvant, or with an alternative peptide adjuvant such as the shark invariant chain; or variants thereof. In another embodiment, the polypeptide may comprise or consist of the sequence of SEQ ID NO: 122 without the TPA peptide adjuvant, or with an alternative peptide adjuvant such as the shark invariant chain; or variants thereof. In another embodiment, the polypeptide may comprise or consist of the sequence of SEQ ID NO: 123 without the TPA peptide adjuvant, or with an alternative peptide adjuvant such as the shark invariant chain; or variants thereof. In another embodiment, the polypeptide may comprise or consist of the sequence of SEQ ID NO: 124 without the TPA peptide adjuvant, or with an alternative peptide adjuvant such as the shark invariant chain; or variants thereof. In another embodiment, the polypeptide may comprise or consist of the sequence of SEQ ID NO: 125 without the TPA peptide adjuvant, or with an alternative peptide adjuvant, such as the shark invariant chain; or variants thereof. Embodiments of the polypeptide without a peptide adjuvant may also not comprise the associated first (N-terminal) linker sequence.

The polypeptide may comprise any one of GT1_short_A_TPA described herein. In another embodiment, the polypeptide may comprise GT1_long_D_TPA described herein. In another embodiment, the polypeptide may comprise GT1&3_short_A_TPA described herein.

In another embodiment, the polypeptide may comprise GT1&3_long_D_TPA described herein. In another embodiment, the polypeptide may comprise GT1-6_short_A_TPA described herein. In another embodiment, the polypeptide may comprise GT1-6_long_D_TPA described herein. In another embodiment, the polypeptide may comprise GT1-6_long_D_TPA_no linkers described herein. In another embodiment, the polypeptide may comprise GT1-6_long_D_Non-TPA_linkers described herein. Variants of the above polypeptides may also be provided with or without the TPA peptide adjuvant, or with an alternative peptide adjuvant.

In one embodiment, the polypeptide may consist essentially of conserved peptide sequences and a peptide adjuvant. In one embodiment, the polypeptide may consist essentially of conserved peptide sequences, one or more linkers, and a peptide adjuvant. The one or more linkers may be disposed between adjacent conserved peptide sequence. The peptide adjuvant may be N-terminal.

Variants of the polypeptide may comprise or consist of a sequence having at least 80% identity with the polypeptide of the invention, for example any one of SEQ ID NO: 118 to 125. Alternatively, variants of the polypeptide may comprise or consist of a sequence having at least 85% identity with the polypeptide of the invention. Variants of the polypeptide may comprise or consist of a sequence having at least 90% identity with the conserved sequence. Variants of the polypeptide may comprise or consist of a sequence having at least 95% identity with the polypeptide of the invention. Variants of the polypeptide may comprise or consist of a sequence having at least 98% identity with the polypeptide of the invention. Variants of the polypeptide may comprise or consist of a sequence having at least 99% identity with the polypeptide of the invention. Variants of the polypeptides of SEQ ID NO: 118 to 125 may include the consensus sequence of one or more conserved peptide sequences instead of the specific patient sequence, or vice versa.

Variants of conserved peptide sequences may comprise or consist of a sequence having at least 80% identity with the conserved peptide sequence. Alternatively, variants of conserved peptide sequences may comprise or consist of a sequence having at least 85% identity with the conserved peptide sequence. Variants of conserved peptide sequences may comprise or consist of a sequence having at least 90% identity with the conserved peptide sequence. Variants of conserved peptide sequences may comprise or consist of a sequence having at least 95% identity with the conserved peptide sequence. Variants of conserved peptide sequences may comprise or consist of a sequence having at least 98% identity with the conserved peptide sequence. Variants of conserved peptide sequences may comprise or consist of a sequence having at least 99% identity with the conserved peptide sequence. Variants of conserved peptide sequences may comprise or consist of a truncated sequence of the conserved peptide sequences. For example any one or more of the sequences of SEQ ID NOs: 1-117, herein may be truncated and still provide immunogenicity in the polypeptide. The truncated sequence may comprise a sufficient number of amino acids to form a recognisable epitope (e.g. at least the minimum number of residues for specific T cell recognition) from a sequence within any one of the sequences of SEQ ID NOs: 1-117. The truncated sequence may comprise at least 7 amino acids of the sequences of SEQ ID NOs: 1-117. Alternatively, the truncated sequence may comprise at least 8 amino acids of the sequences of SEQ ID NOs: 1-117. Alternatively, the truncated sequence may comprise at least 9, 10, 11 or 12 amino acids of the sequences of SEQ ID NOs: 1-117. Multiple truncated sequences may be provided within one of the conserved peptide sequences of SEQ ID NOs: 1-117.

In one embodiment, any one of the conserved peptide sequences of SEQ ID NOs: 1-117 may be varied, for example by residue substitution, addition or deletion. The variant conserved peptide sequences may still function to provide recognisable HCV epitopes. The skilled person will understand that natural variation exists in any given population and that these variants may have some sequence variation with the consensus sequence, or example patient sequences provided in SEQ ID NOs: 1-117. Therefore, the variant conserved peptide sequences may have at least 70% sequence identity with any one of SEQ ID NOs: 1-117. In another embodiment, the variant conserved peptide sequences may have at least 74% sequence identity with any one of SEQ ID NOs: 1-117. In another embodiment, the variant conserved peptide sequences may have at least 75% sequence identity with any one of SEQ ID NOs: 1-117. In another embodiment, the variant conserved peptide sequences may have at least 79% sequence identity with any one of SEQ ID NOs: 1-117. In another embodiment, the variant conserved peptide sequences may have at least 80% sequence identity with any one of SEQ ID NOs: 1-117. In another embodiment, the variant conserved peptide sequences may have at least 82% sequence identity with any one of SEQ ID NOs: 1-117. In another embodiment, the variant conserved peptide sequences may have at least 83% sequence identity with any one of SEQ ID NOs: 1-117. In another embodiment, the variant conserved peptide sequences may have at least 85% sequence identity with any one of SEQ ID NOs: 1-117. In another embodiment, the variant conserved peptide sequences may have at least 88% sequence identity with any one of SEQ ID NOs: 1-117. In another embodiment, the variant conserved peptide sequences may have at least 90% sequence identity with any one of SEQ ID NOs: 1-117. In another embodiment, the variant conserved peptide sequences may have at least 92% sequence identity with any one of SEQ ID NOs: 1-117. In another embodiment, the variant conserved peptide sequences may have at least 95% sequence identity with any one of SEQ ID NOs: 1-117. In another embodiment, the variant conserved peptide sequences may have at least 98% sequence identity with any one of SEQ ID NOs: 1-117. In another embodiment, the variant conserved peptide sequences may have at least 99% sequence identity with any one of SEQ ID NOs: 1-117. In another embodiment, the variant conserved peptide sequences may have at least 99.5% sequence identity with any one of SEQ ID NOs: 1-117.

Reference to sequence "identity" used herein may refer to the percentage identity between two aligned sequences using standard NCBI BLASTp parameters (http://blast.ncbi.nlm.nih.gov).

The conserved peptide sequences may vary in length, with the minimum length being defined as the minimum number of residues required to form a recognisable epitope. Therefore the conserved peptide sequence may be from about 7 to 250 amino acids in length, or more. For example, at least one conserved peptide sequence may be at least about 7 amino acids in length. In another embodiment, at least one conserved peptide sequence may be at least about 8 amino acids in length. In another embodiment, at least one conserved peptide sequence may be at least about 10 amino acids in length. In another embodiment, at least one conserved peptide sequence may be at least about 15 amino acids in length. In another embodiment, at least one conserved peptide sequence may be at least about 20 amino acids in length. In another embodiment, at least one conserved peptide sequence may be at least about 30 amino acids in length. In one embodiment, at least one conserved peptide sequence may be between about 20 and about 220 amino acids in length. In one embodiment, at least one conserved peptide sequence may be no more than about 300 amino acids in length. In another embodiment, at least one conserved peptide sequence may be no more than about 250 amino acids in length. In another embodiment, at least one conserved peptide sequence may be no more than about 200 amino acids in length. In another embodiment, at least one conserved peptide sequence may be no more than about 150 amino acids in length. In another embodiment, at least one conserved peptide sequence may be no more than about 100 amino acids in length. In another embodiment, at least one conserved peptide sequence may be no more than about 50 amino acids in length.

The conserved peptide sequences may be an average length of between about 20 and about 80 amino acids in a population of conserved peptide sequences.

In some embodiments of the invention, the polypeptide of the invention may further comprise a peptide adjuvant, such as a TPA (tissue plasminogen activator) sequence, or functional variants thereof. The TPA may comprise or consist of the sequence: MDAMKRGLCCVLLLCGAVFVSPSQEIHARFRR (SEQ ID NO: 194), or a functional variant thereof. In one embodiment, the peptide adjuvant may comprise a Shark invariant chain, for example of the sequence SLLWGGVTVLAAMLIAGQVASSVVFLV (SEQ ID NO: 195), or a functional variant thereof. The peptide adjuvant may be N-terminal on the polypeptide of the invention. A functional variant of a peptide adjuvant may be a truncated or mutated peptide variant, which can still function as an adjuvant, for example a truncated or mutated variant of the TPA or shark invariant chain, which still function as an adjuvant. The skilled person will appreciate that 1, 2, 3, 4, 5 or more amino acid residues may be substituted, added or removed without affecting function. For example, conservative substitutions may be considered.

In one embodiment the polypeptide is an isolated polypeptide. In another embodiment, the polypeptide may be encoded in nucleic acid or in a viral vector.

Combinations of different polypeptides according to the invention may be provided as a vaccine. For example, a prime and/or boost vaccine formulation may comprise nucleic acid or viral vector encoding two or more polypeptides of the invention, which may be different relative to each other.

The polypeptide may be used in a vaccine in combination with another therapeutically or prophylactically active ingredient. The polypeptide may be used in a vaccine in combination with an adjuvant.

The polypeptide, nucleic acid encoding the polypeptide, or associated viral particle may be provided in a pharmaceutically acceptable carrier.

According to another aspect of the invention there is provided a composition comprising a plurality of different polypeptides according to the invention, optionally wherein the composition is a pharmaceutically acceptable composition.

According to another aspect of the invention there is provided a nucleic acid comprising a sequence encoding a polypeptide according to the invention herein.

The nucleic acid may be a plasmid vector for vaccination. The nucleic acid may comprise viral vector sequences.

According to another aspect of the invention there is provided a viral vector comprising the nucleic acid according to the invention herein.

The viral vector may comprise a virus. The viral vector may comprise an adenovirus, such as a human or simian adenovirus. The viral vector may comprise an adenovirus when used in a prime vaccine of a prime boost regime. The viral vector may comprise ChAdOx1 (a group E simian adenovirus, like the AdCh63 vector used safely in malaria trials) or ChAdOx2 (as described in Morris et al 2016. Future Virol 11(9), pp. 649-659) The viral vector may comprise AdCh63. The viral vector may comprise AdC3 or AdH6. The viral vector may be a human serotype. The viral vector may comprise Modified Vaccinia Ankara (MVA). The viral vector may comprise MVA when used as a vaccine boost in a prime boost regime. The viral vector may comprise Adeno-associated virus (AAV) or lentivirus. The viral vector may be an attenuated viral vector. The polypeptide sequence of the invention may be cloned into any suitable viral vector that is known to elicit good immune response. Suitable viral vectors have been described in Dicks et al (Vaccine. 2015 Feb. 25; 33(9):1121-8. doi: 10.1016/j.vaccine.2015.01.042. Epub 2015 Jan. 25), Antrobus et al (Mol Ther. 2014 March; 22(3):668-74. doi: 10.1038/mt.2013.284. Epub 2013 Dec. 30.), and (Warimwe et al. (Virol J. 2013 Dec. 5; 10:349. doi: 10.1186/1743-422X-10-349), which are incorporated herein by reference.

According to another aspect of the invention there is provided a composition comprising one or more of:
the polypeptide according to the invention;
the nucleic acid according to the invention; and
the viral vector according to the invention.

The composition may be immunogenic, for example in a mammal, such as a human. The composition may comprise a pharmaceutically acceptable carrier. The composition may be a pharmaceutical composition comprising a pharmaceutically acceptable carrier. The composition may be for use in the prophylaxis or treatment of HCV infection.

According to another aspect of the invention there is provided a method of treatment or prophylaxis of HCV infection comprising the administration of:
the polypeptide according to the invention;
the nucleic acid according to the invention;
the composition according to the invention or
the viral vector according to the invention.

The method of treatment or prophylaxis of HCV infection may be a method of vaccination.

According to another aspect of the invention there is provided an agent for use in the prophylaxis or treatment of HCV infection, the agent comprising or consisting of:
the polypeptide according to the invention;
the composition according to the invention;
the nucleic acid according to the invention; or
the viral vector according to the invention.

According to another aspect of the invention there is provided the polypeptide according to the invention; the composition according to the invention; the nucleic acid according to the invention; or the viral vector according to the invention; for use in, or as, a vaccine.

According to another aspect of the invention there is provided a vaccine comprising the polypeptide of the invention comprising or consisting of:
the polypeptide according to the invention;
the composition according to the invention;
the nucleic acid according to the invention; or
the viral vector according to the invention.

The vaccine may be a prime vaccine. The vaccine may be a boost vaccine. Where a boost vaccine is provided following a prime vaccine, the polypeptide may be different. For example, the polypeptide may comprise a re-ordered sequence of conserved peptide sequences. The conserved peptide sequences may be identical, but the order in which they are provided in the polypeptide may be changed. Therefore, the invention herein provides any of the sequences/embodiments of the invention wherein the order in which conserved peptide sequences are provided may be changed. Such embodiments may also include re-ordered or differed linker/junction sequences.

Advantageously, the re-ordering of the conserved peptide sequences of the polypeptide between prime and boost vaccines can avoid the provision of "false" epitopes formed across junctions of one conserved peptide sequence with another conserved peptide sequence. i.e. the same junction may not occur in the re-ordered polypeptide.

According to another aspect of the invention, there is provided a polypeptide according to the invention for use in, or as, a vaccine.

According to another aspect of the invention, there is provided a prime boost vaccination kit comprising
a prime vaccination according to the invention;
a boost vaccination according to the invention.

The prime and boost vaccinations may be different. The prime and boost vaccination may differ in the polypeptide sequence. The prime and boost vaccination may comprise different viral vectors.

The term "immunogenic", when applied to the polypeptide or composition of the present invention means capable of eliciting an immune response in a human or animal body. The immune response may be protective.

The term "isolated", when applied to the polypeptide of the present invention means a polypeptide: (i) encoded by nucleic acids using recombinant DNA methods; or (ii); synthesized by, for example, chemical synthetic methods; or (iii) separated from naturally-occurring biological materials, and then purified using polypeptide analytical procedures; or (iv) associated with chemical moieties (e.g. peptides, carbohydrates, fatty acids, and the like) other than those associated with the antigenic peptide in its naturally-occurring state; or (v) that do not occur in nature. An isolated polypeptide of the invention includes a polypeptide expressed from a nucleotide sequence encoding the polypeptide, or from a recombinant vector containing a nucleotide sequence encoding the polypeptide. An isolated polypeptide of the invention may include a polypeptide expressed from a virus-like particle.

The term "protective" means prevention of a disease, a reduced risk of disease infection, transmission and/or progression, reduced severity of disease, a cure of a condition or disease, an alleviation of symptoms, or a reduction in severity of a disease or disease symptoms.

The term "prophylaxis" means prevention of or protective treatment for a disease. The prophylaxis may include a reduced risk of disease infection, transmission and/or progression, or reduced severity of disease.

The term "treatment", means a cure of a condition or disease, an alleviation of symptoms, or a reduction in severity of a disease or disease symptoms.

According to another aspect of the invention, there is provided a composition comprising a polypeptide according to the invention herein, and a pharmaceutically acceptable carrier.

The composition may not comprise wild-type HCV. The composition may not comprise full length/complete structural or non-structural HCV protein sequence.

The use may be with a pharmaceutically acceptable carrier. Additionally or alternatively, the use may be with an adjuvant.

According to another aspect of the invention, there is provided a nucleic acid encoding essentially or at least the polypeptide according to the invention herein.

According to another aspect of the invention, there is provided a viral vector encoding the polypeptide according to the invention herein.

The viral vector or nucleic acid may be provided in a composition, wherein composition may comprise a pharmaceutically acceptable carrier. The viral vector or nucleic acid may not encode wild-type HCV or full length/complete HCV NS protein. The viral vector or nucleic acid may not encode structural protein sequence of HCV. The viral vector or nucleic acid may not encode non-conserved protein/peptide sequence of HCV.

The skilled person will understand that optional features of one embodiment or aspect of the invention may be applicable, where appropriate, to other embodiments or aspects of the invention.

Embodiments of the invention will now be described in more detail, by way of example only, with reference to the accompanying drawings.

FIG. 1: Identification of conserved HCV peptide segments. Sequence diversity plot of the full HCV genome with defined conserved HCV segments. (A) The calculated sequence diversity for an example sequence dataset is shown for the full HCV genome (sequence dataset HCV gt1/3a, containing 72 sequences) using a window size of k=20. For conserved vaccine design, segments with a variability <25% (lowest quartile, marked blue) were defined as conserved and selected for conserved immunogen design. (B) Consensus sequences for selected conserved segments for three different immunogen analyses HCV genotype 1 (a, blue) (SEQ ID NO: 1-7, 9, 10. 12, 13, 15, 17, 18. 20, 21, 23-27, 29-35, 37 and 38), HCV genotype 1/3 (b, green) (SEQ ID NO: 39, 41, 43-48, 50, 52, 54, 56, 58, 60, 61, 63-65, 67, 69, 71-73, 75, 76, 78 and 80) and HCV genotype 1-6 (c, orange) (SEQ ID NO: 81, 83, 84, 44, 85, 86, 88, 90, 92, 94, 96, 97, 99, 101, 103, 105, 106, 108, 109, 110, 112-114 and 116) are depicted. Conserved segments are numbered after position on the HCV genome, with viral regions specified.

FIG. 2: Patient sequence selection for final immunogen design. (A) Similarity of subtype consensus sequences (depicted as coloured spots) to overall consensus sequences at each conserved segment, shown for analyses HCV gt1 (a, left), HCV gt1/3 (b, middle) and HCV gt1-6 (c, right) immunogens. (B) Number of patient sequences selected of each genotype for the final conserved immunogens HCV gt1 (left), HCV gt1/3 (middle) and HCV gt1-6 (right).

Figure 3:
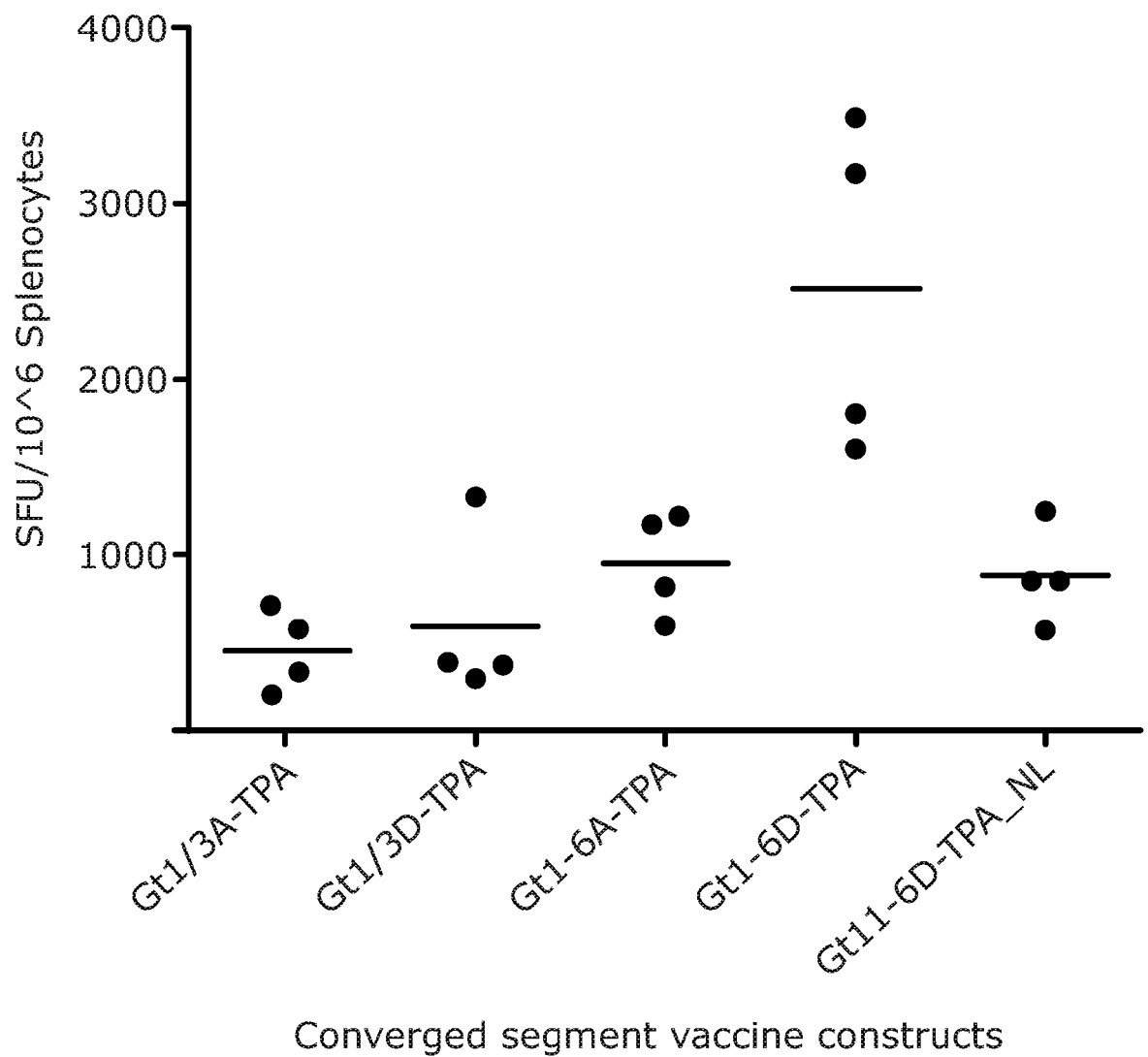

FIG. 3: The Total magnitude of HCV specific T cell responses to conserved segment vaccines in mouse models. BALB/c mice (4/group) are vaccinated with each vaccine at $10^8$IU intramuscularly. Splenocytes are harvested 2 weeks later. The total magnitude of HCV specific T cell responses using pools of HCV genotype 1b peptides in ex vivo IFN-γ ELISpot assays. Bars represent the mean.

Figure 4A:
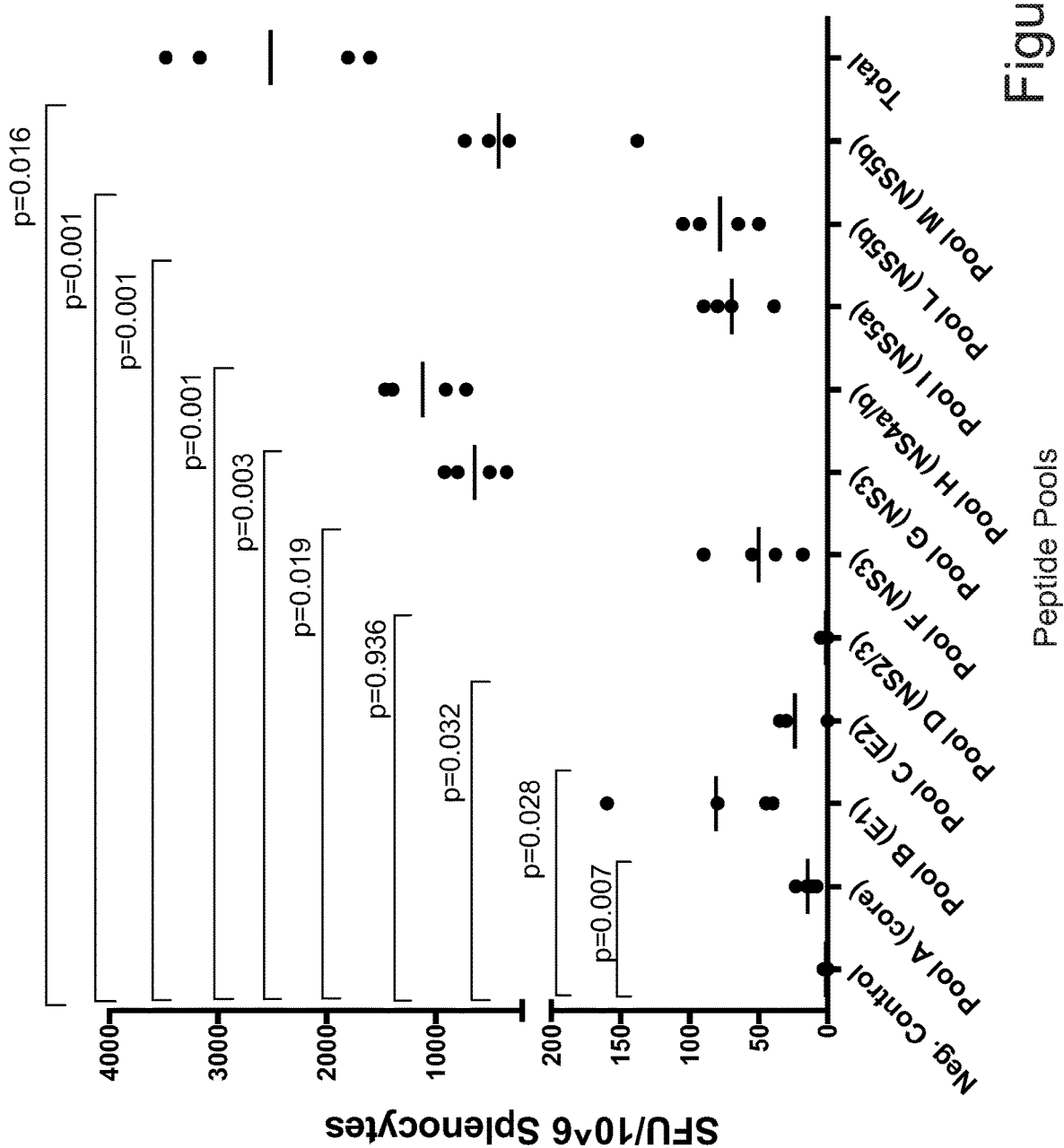

FIG. 4: The breadth of HCV specific T cell responses to conserved segment vaccines. BALB/c mice receive $10^8$IU vaccine intramuscularly. Splenocytes are harvested 2 weeks later. The magnitude of HCV specific T cell responses to individual pools (A-M) of HCV genotype 1b peptides spanning the viral genome and concavalin A (positive control) are assessed in ex vivo IFN-γ ELISpot assays. Bars represent the mean+/−SD. (A) Individual data in four mice receiving Gt1-6D-TPA vaccine is shown. (B) HCV specific T cell responses to gt1-6D, GT1/3D and ChAdOx1 GFP control vaccines are shown.

Figure 5:
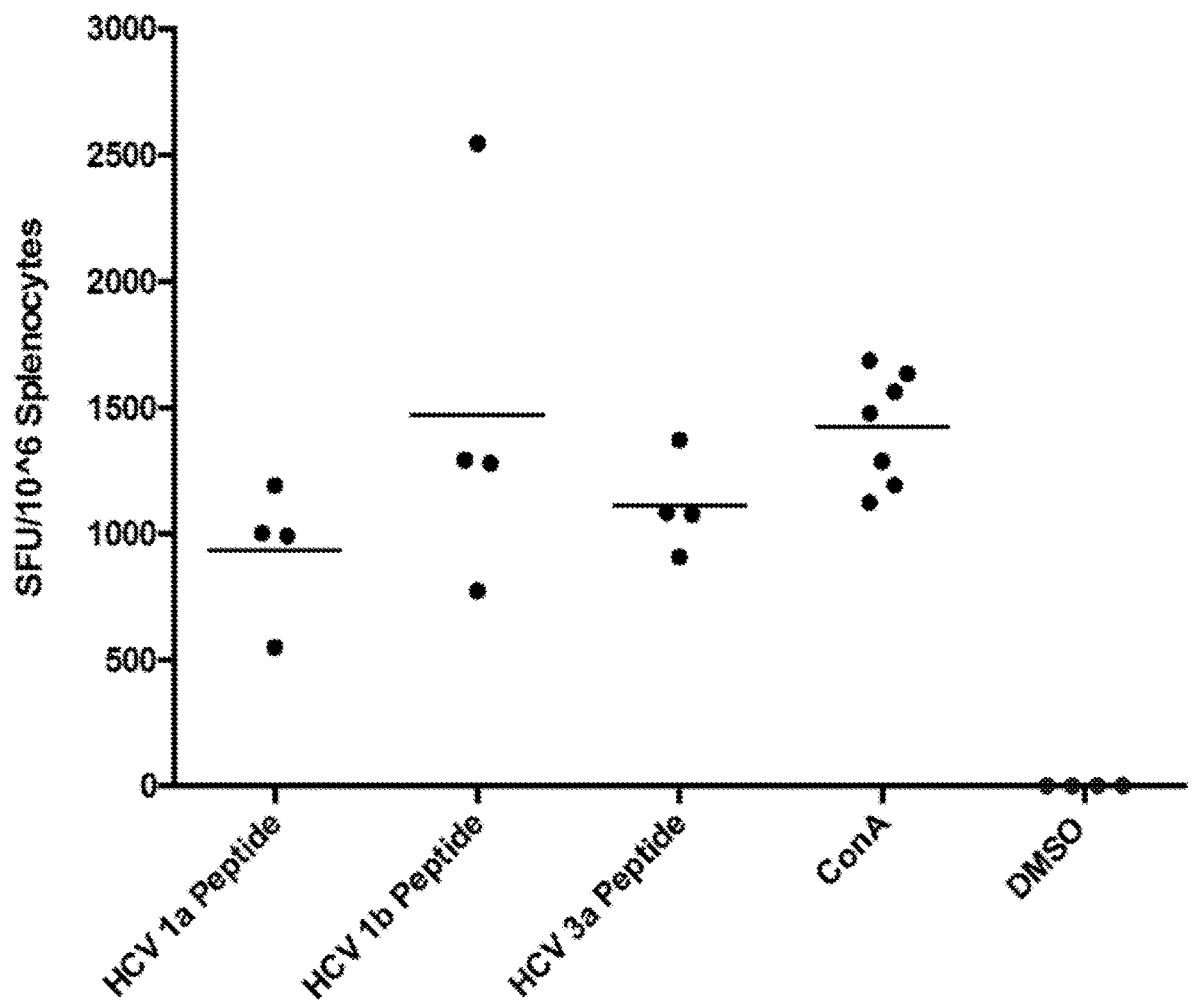

FIG. 5: Inter-genotypic T cell cross-reactivity of total HCV specific T cell responses to conserved segment vaccines. C57BL/6 mice receive $10^8$ IU Gt1-6D-TPA vaccine intramuscularly. Splenocytes are harvested 2 weeks later. The total magnitude of HCV specific T cell responses to HCV genotype 1a, ab and 3a peptides spanning the entire immunogen are shown. Bars represent the mean.

Figure 6:
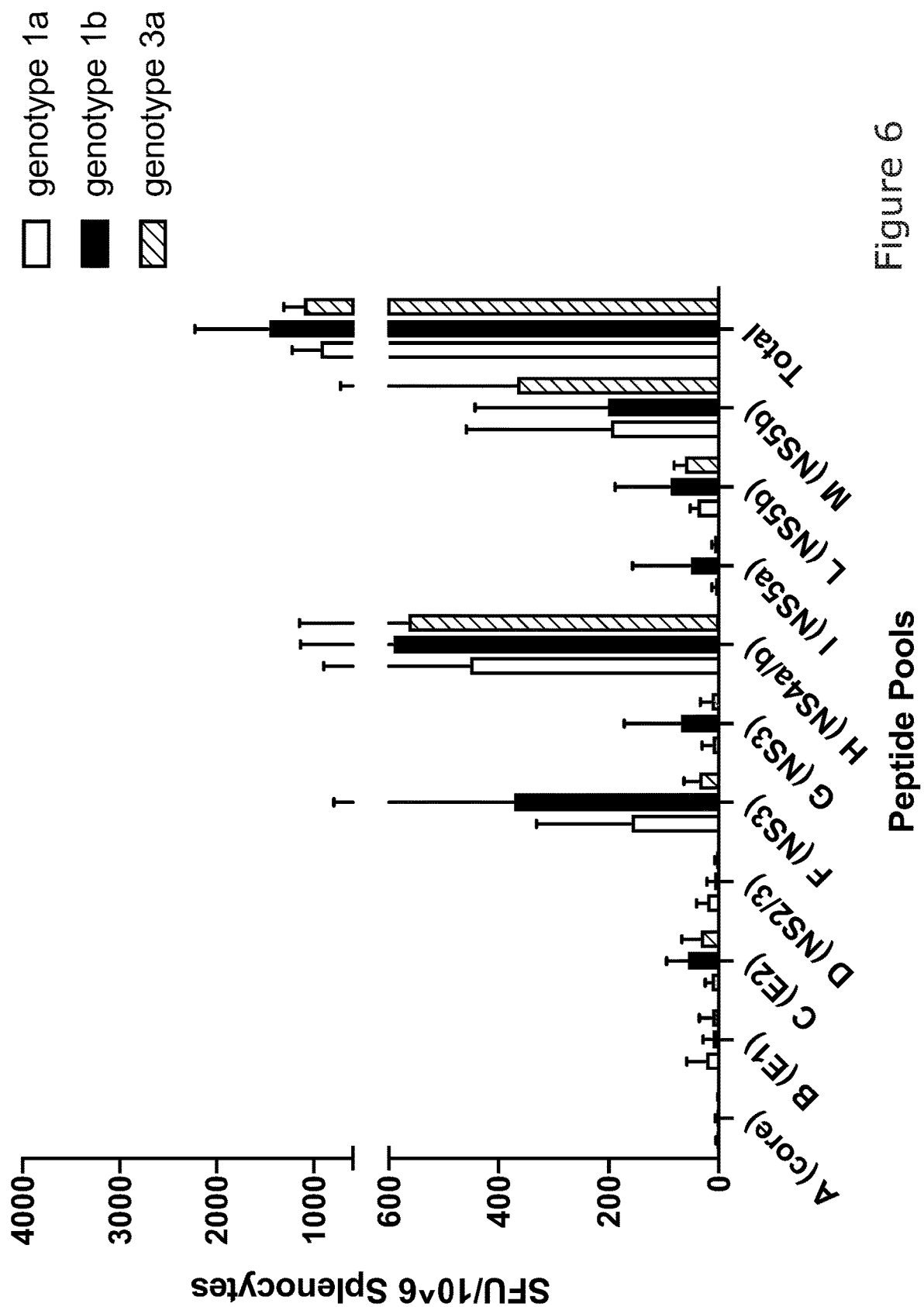

FIG. 6: Inter-genotypic T cell cross-reactivity in peptide pools to conserved segment vaccines. C57BL/6 mice receive $10^8$ IU of gt1-6D-TPA vaccine intramuscularly. Splenocytes are harvested 2 weeks later. The magnitude of HCV specific T cell responses to individual pools of HCV genotype 1a, 1b and 3b peptides spanning the viral genome are assessed in ex vivo IFN-γ ELISpot assays. Bars represent the mean+/−SD.

Figure 7A:
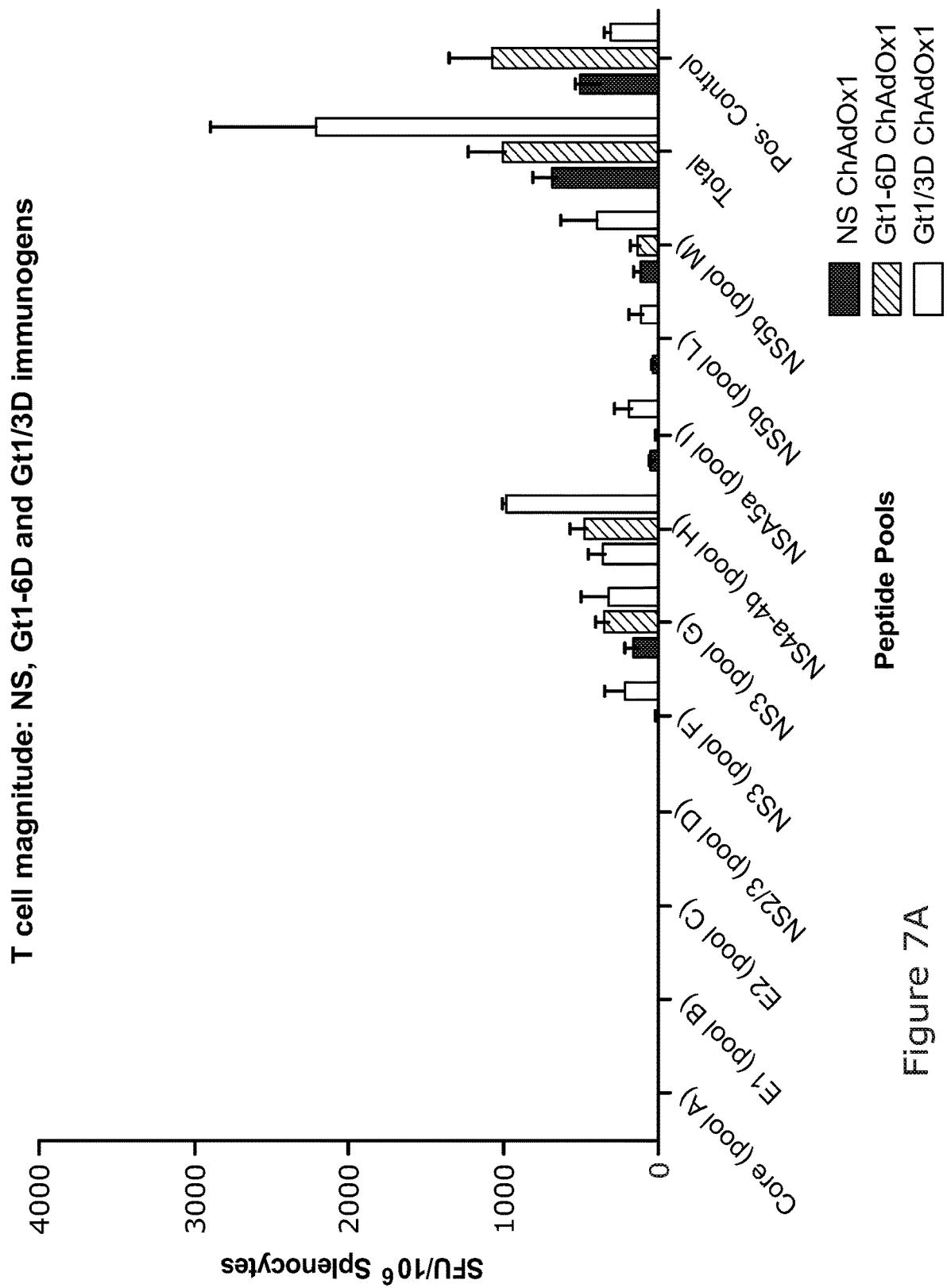
Figure 7B:
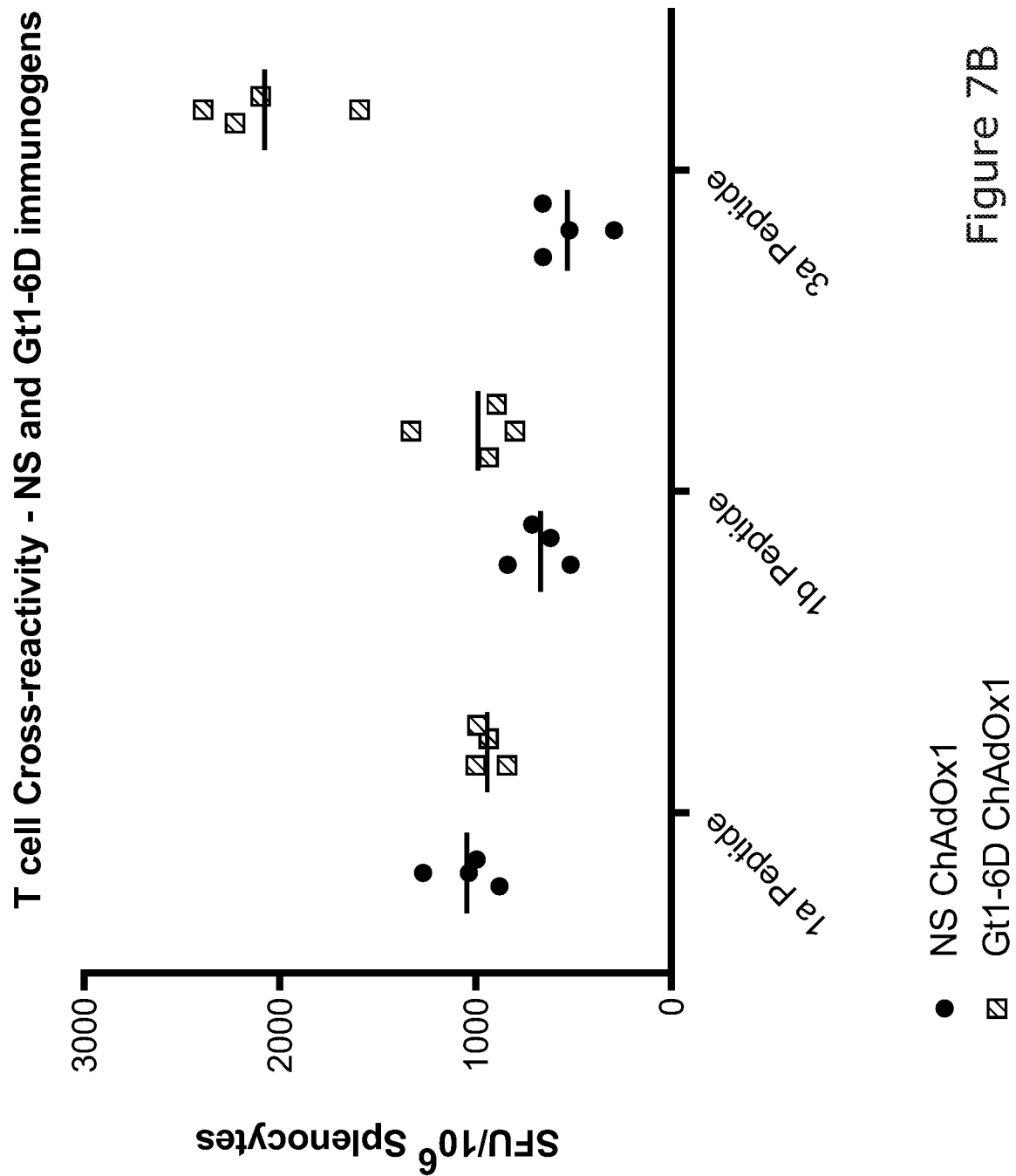
Figure 7C:
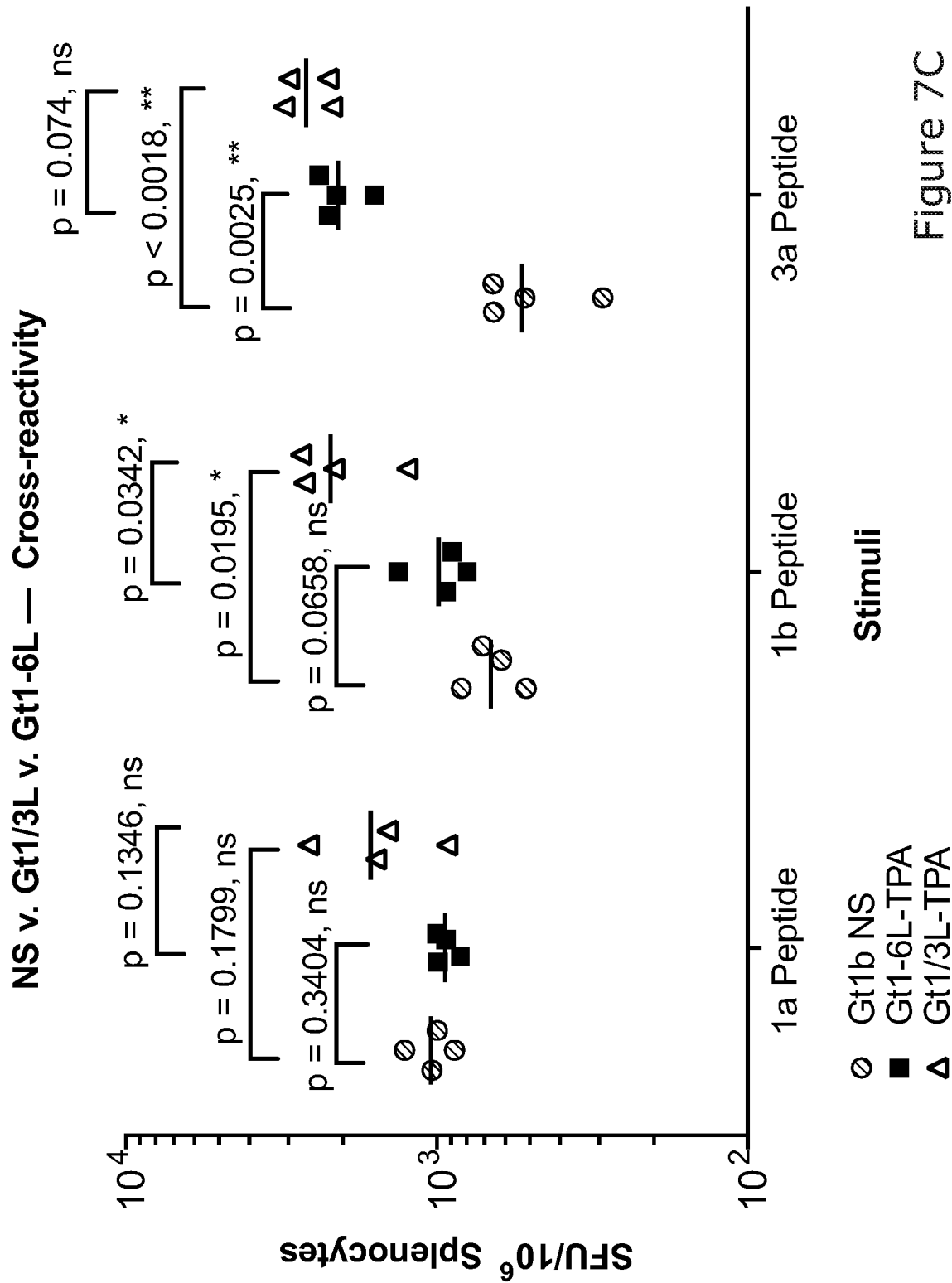

FIG. 7: Breadth, magnitude and T cell cross-reactivity of conserved segment compared to an NS genotype 1b immunogen. BALB/c mice receive $10^8$IU of gt1-6D-TPA, Gt1/3D ChAdOx1 or NS1b ChAdOx1 vaccine intramuscularly. Splenocytes are harvested 2 weeks later and stimulated with HCV peptides or the positive control concavalin A in in ex vivo IFN-γ ELISpot assays. (A) The magnitude of HCV specific T cell responses to individual peptide pools (genotype 1b; A-M) is shown for each vaccine. (B) and (C) total T cell cross-reactivity to HCV 1a, 1b and 3b peptides spanning the viral genome are assessed. Bars represent the mean+/−SD.

Figure 8:
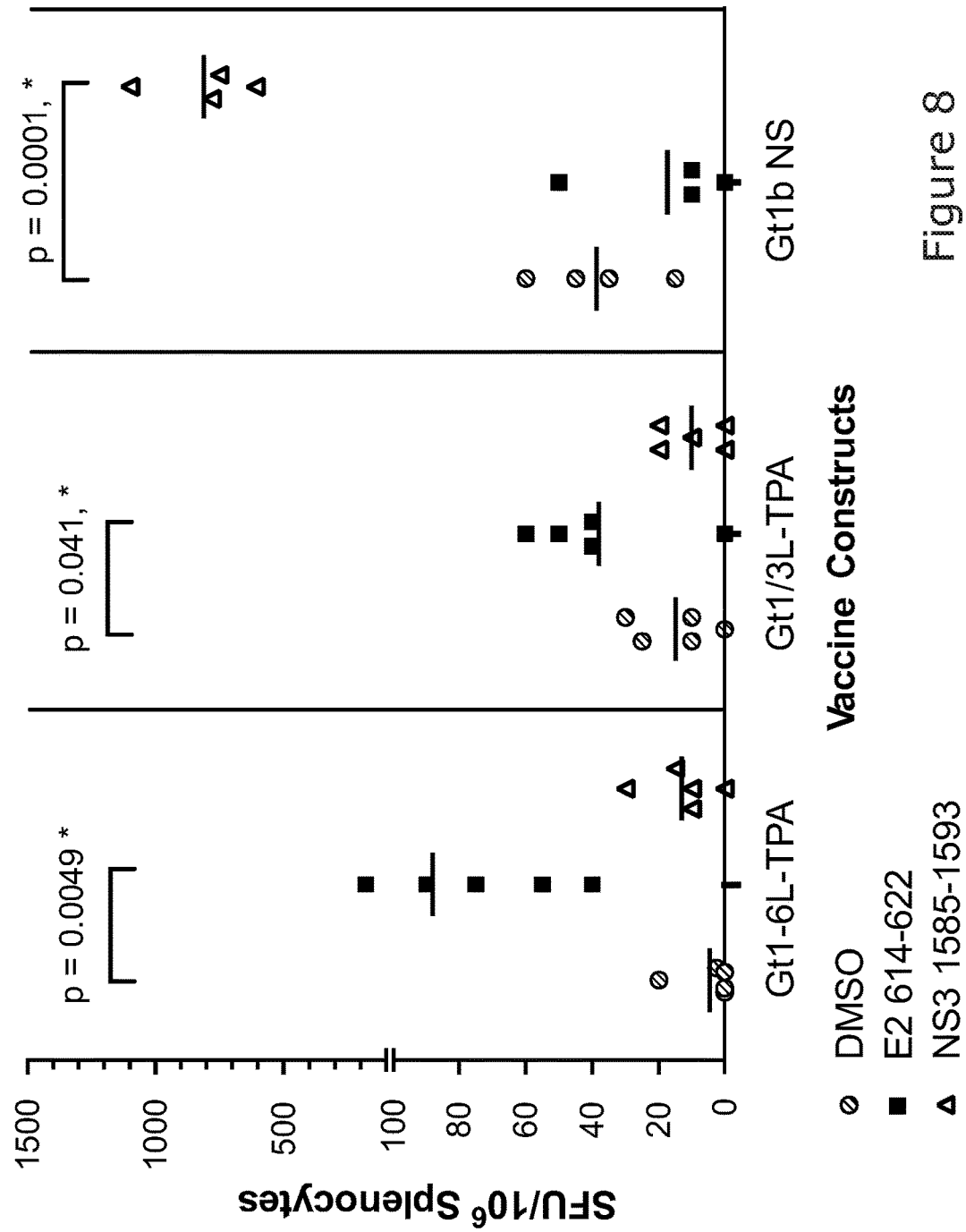

FIG. 8: A2-restricted HCV-specific T cell responses in C57BL/6-Tg (HLA-A2.1) transgenic mice. Ex vivo IFNg ELISpot responses from transgenic C57BL/6-Tg (HLA A2.1) mice when vaccinated, intramuscularly, with conserved segment HCV vaccines, Gt1/3D-TPA and Gt1-6D-TPA, and a Gt1b NS-TPA control. At 14 days post-vaccination, splenocytes were harvest and stimulated with 15-18mer peptides matching known HCV A2 epitopes. Of the 10-15 A2-specific epitopes present in the conserved segment vaccines, only the statistically significant responses are shown (unpaired T-test). Note, the significant A2-specific T cell response in Gt1-6D was stimulated by the Gt-3 variant of E2614, despite the recalled T cell population initially primed with a Gt-1a sequence during vaccination. Bars represent the geometric mean.

Figure 9:
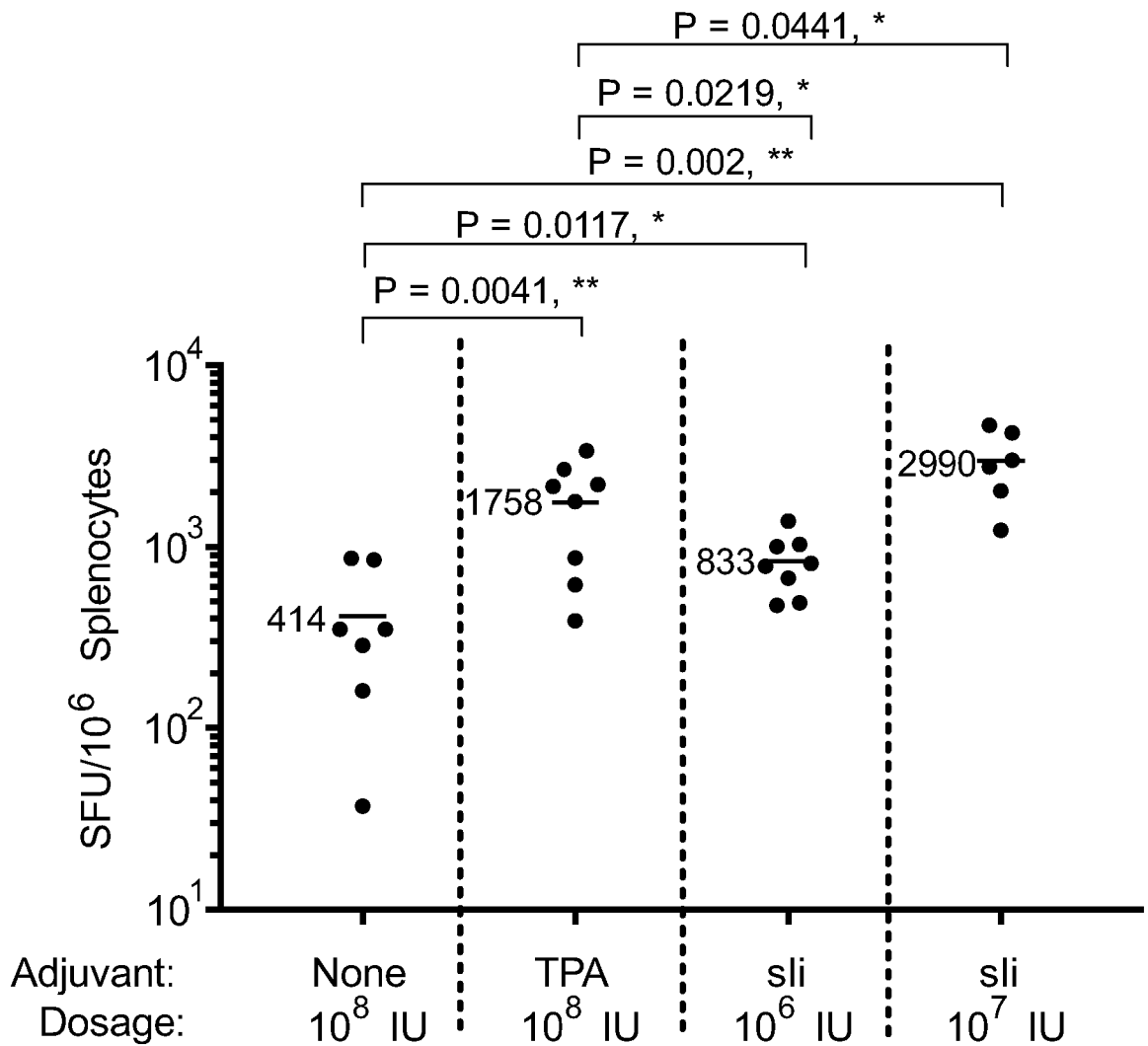

FIG. 9: Effect of shark invariant chain (sIi) on the immunogenicity of conserved segment vaccine, Gt1-6D. T cell magnitude of conserved segment vaccine, Gt1-6L, is shown with different genetic adjuvants tethered to the immunogen cassette. Outbred CD-1 mice (8/group) received various dosages (IU) of gt1-6D-TPA vaccine, in a ChAdOx1 vector, intramuscularly. Splenocytes were harvested 3-weeks post-vaccination and stimulated with HCV 1b peptides. Bars represent the mean.

1. We developed a computer algorithm to identify HCV genomic segments from open resource databases and in-house sequences that were conserved between viral subtypes. Conserved segments below a pre-defined threshold spanning the entire HCV coding genome were selected (FIG. 1A) and combined to create novel immunogens of either approximately 1000 amino acids (denoted in vaccine name by letter A), or 1500 AA (denoted in vaccine name by letter D) for each of HCV genotypes 1a and 1b, genotypes 1 and 3, and genotypes 1 to 6. In the vaccine constructs following homology was observed—Genotype 1: 94.8%, Genotypes 1-3:95.5%, genotypes 1-6: 90.3%.

We note 1141 amino-acids are 100% conserved between the GT1, GT1/3 and GT1-6 vaccines, which equates to 74% for GT1 (1141/1544), 79% for GT1/3 (1141/1444) and 83% for GT1-6 (1141/1377).

2. The exact sequence to be included in each conserved segment was identified in 2 steps-(i) assessing the HCV subtype or genotype consensus sequence that was most homologous with a consensus of all HCV sequences in the algorithm, and (ii) identifying a real patient sequence that was most homologous with the HCV subtype consensus sequence (FIG. 2).

3. Putative artificial epitopes restricted by common HLA super-types in junction regions were abrogated through the insertion of amino-acid linkers and analysed using BLAST to exclude potential cross-reactivity with human self-peptides.

4. Plasmid DNA, encoding HCV conserved genomic segments with linkers, tissue plasminogen activator (TPA) leader sequence and Kozak sequence were chemically synthesised using ThermoFisher Scientific GeneArt™ Gene Synthesis service. Gene constructs were cloned into a pENTR4 vector downsteam to the human cytomegalovirus immediate early promoter and tetracycline operator sequences. The entire coding cassette was then moved into the ChAdOx1 destination vector using Thermo Fisher Scientific LR gateway cloning procedure. Simian adenoviral vaccines (ChAdOx1) encoding the new HCV immunogens were derived by transfecting ChAdOx1-$HCV_{cons}$ plasmids into T-REx™-293 cells (Thermo Fisher Scientific). All the ChAdOx1-HCV$_{cons}$ vaccines were generated at the viral vector core facility at the Jenner Institute, University of Oxford, Oxford, UK.

Figure 4B:
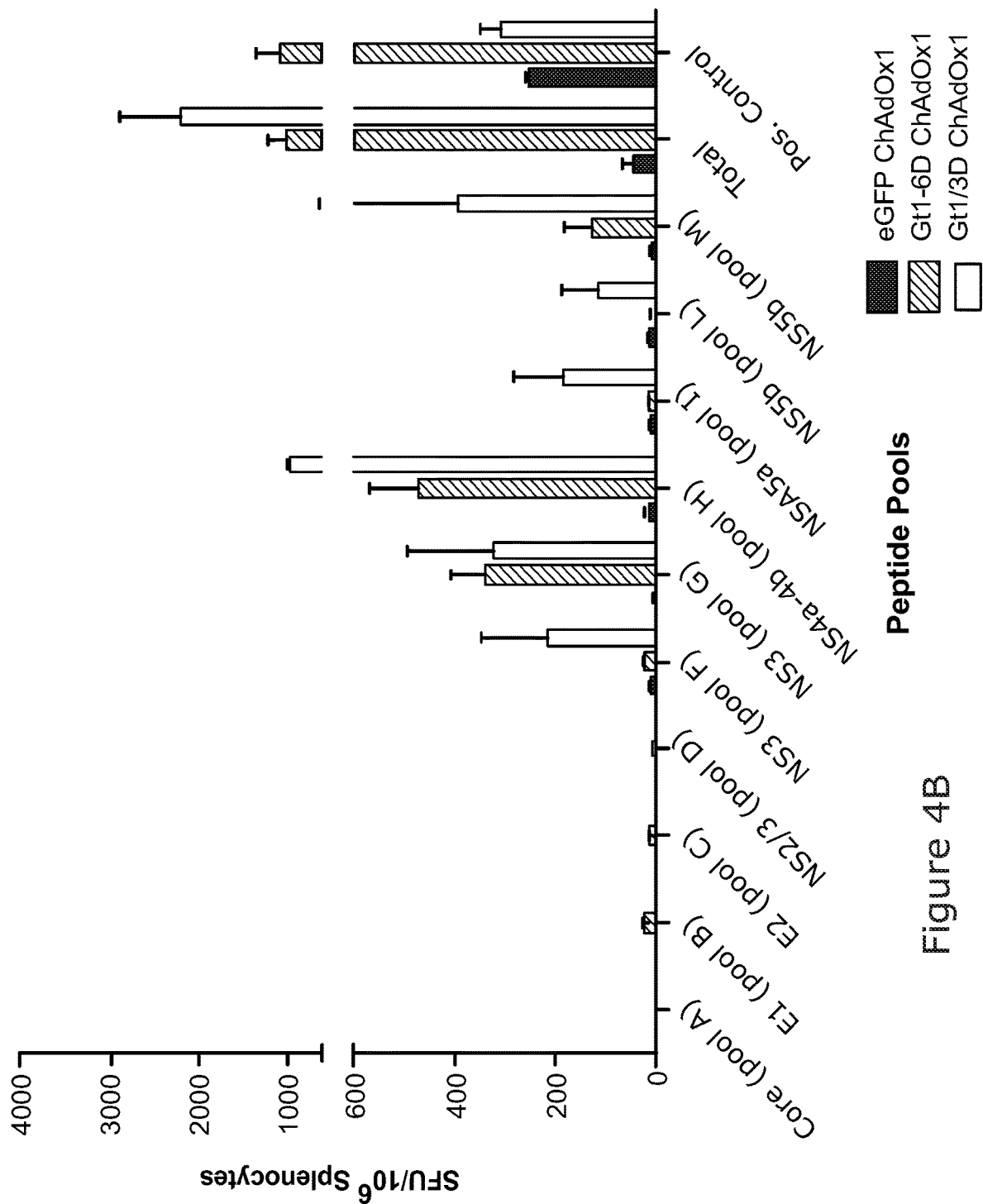

5. We show that conserved immunogens administered using the adenoviral vector ChAdOx1 prime potent T-cell response in mice. In BALB/c mice, total responses for Gt1/3D ChAdOx1 and Gt1-6D ChAdOx1 had an average SFU/10$^6$ splenocytes of 594 and 2514 (FIG. 3). These immunogens gave significant responses to most individual HCV peptides pools when compared to the DMSO control (FIG. 4a; gt1-6D-TPA shown and to the control eGFP ChAdOx1 vaccine (FIG. 4b).

6. Vaccination with conserved immunogen vaccines induced T cell responses that were highly cross-reactive with different HCV genotypes. C57BL6 mice were vaccinated with Gt1-6D ChAdOx1. Splenocytes were harvested 2 weeks later and stimulated with peptides from HCV genotypes 1a, 1b and 3a giving mean total magnitude responses of 935, 1474 and 1112 SFU/10$^6$ splenocytes respectively that were significantly higher than the negative DMSO control (FIG. 5). T cell responses that were cross-reactive were also observed at the level of the individual HCV peptide pools (FIG. 6). The novel conserved immunogen vaccines were equally immunogenic and more cross-reactive with multiple HCV genotypes than a vaccine encoding a single HCV genotype-1b genome (NS1b ChAdOx1) encoded by the same ChAdOx1 vector (FIG. 7).

Conclusions: Novel pan-genotypic HCV simian adenoviral vectored vaccines encoding conserved segments from all major HCV genotypes are highly immunogenic target multiple areas of the HCV genome and are cross-reactive between HCV genotypes, in mouse models. These studies pave the way for the assessment of pan-genotypic HCV T cell vaccines in humans.

Overview on Immunogens Designed, Generated and Tested in Mice

TABLE 1

Experimental stages of designed HCV conserved vaccine constructs. Constructs are marked in an "X" if they have moved forward to the next experimental stage.

| Immunogen ID | Designed | pENTR4/plasmid cloning | Inserted into ChAdOx1 | Tested in mice |
| --- | --- | --- | --- | --- |
| GT1_short_A_TPA_linkers | X | X | X | |
| GT1_long_D_TPA_linkers | X | | | |
| GT1/3_short_A_TPA_linkers | X | X | X | X |
| GT1/3_long_D_TPA_linkers | X | X | X | X |
| GT1-6_short_A_TPA_linkers | X | X | X | X |
| GT1-6_long_D_TPA_linkers | X | X | X | X |
| GT1-6_long_D_TPA_nolinkers | X | X | X | X |
| GT1-6_long_D_noTPA_linkers | X | | | |

Key for sequences below:
TPA leader sequence (underlined bold):

(SEQ ID NO: 194)
MDAMKRGLCCVLLLCGAVFVSPSQEIHARFRR

Linkers=in lower case and marked in bold.

>GT1_short_A_TPA (SEQ ID NO: 118)
MDAMKRGLCCVLLLCGAVFVSPSQEIHARFRRkgggpgggkSTNPKPQRKTKRNTNRRP

QDVKFPGGGQIVGGVYLLPRRGPRLGVRATRKTSERSQPRGRRQPIPKARRPEGRTWAQ

PGYPWPLYGNEGCGWAGWLLSPRGSRPSWGPTDPRRRSRNLGKVIDTLTCGFADLMGYI

PLVGAPLGGAARALAHGVRVLEDGVNYATGNLPGCSFSIFLLALLSCLTVPASAggsgD

RDRSELSPLLLSTTQWQVLPCSFTTLPALSTGLIHLHQNIVDVQYLYGVGSSVgpPCTC

GSSDLYLVTRHADVIPVRRRGDSRGSLLSPRPISYLKGSSGGPLLCPSGHAVGIFRAAV

CTRGVAKAVDFIPVESMETTMRSPVFTDNSSPPAVPQTFQVAHLHAPTGSGKSTKVPAA

YAAQGYKVLVLNPSVAATLGFGAYMSKAHGVsgTGVRTITTGSPITYSTYGKFLADGGC

SGGAYDIIICDECHSTDATSILGIGTVLDQAETAGARLVVLATATPPGSVTVPHPNIEE

VgpgNAVAYYRGLDVSVIPTSGDVVVVATDALMTGFTGDFDSVIDCNTCVTQTVDFSLD

PTFTIETTTLPQDAVSRTQRRGRTGRGRpgggsgggYRFVTPGERPSGMFDSSVLCECY

DAGCAWYELTPAETTVRLRAYLNTPGLPVCQDHLEFWEGVFTGLTHIDAHFLSQTKQAG

DNFPYLVAYQATVCARAQAPPPSWDQMWKCLIRLKPggkgpggKYIMTCMSADLEVVTS

TWVLVGGVLAALAAYCLSTGCVVIVGRIVLSGgsgGSIGLGKVLVDILAGYGAGVAGAL

-continued

VAFKIMSGEVPSTEDLVNLLPAILSPGALVVGVVCAAILRRHVGPGEGAVQWMNRLIAF

ASRGNHVSPTHYVPESDAAARVTQILSgpSLTERLYVGGPLTNSKGQNCGYRRCRASGV

LTTSCGNTLTCYLKASAACRAAKLggpgSLRAFTEAMTRYSAPPGDPPQPEYDLELITS

CSSNVSVAHDASGKRVYYLTRDPTTPLARAAWETARHTPVNSWLGNIIMYAPTLWARMI

LggsggEPLDLPQIIQRLHGLSAFSLHSYSPGEINRVAACLRKLGVPPLRAWRHRARSV

RA

>GT1_long_D_TPA (SEQ ID NO: 119)

MDAMKRGLCCVLLLCGAVFVSPSQEIHARFRRkgggpgggkSTNPKPQRKTKRNTNRRP

QDVKFPGGGQIVGGVYLLPRRGPRLGVRATRKTSERSQPRGRRQPIPKARRPEGRTWAQ

PGYPWPLYGNEGCGWAGWLLSPRGSRPSWGPTDPRRRSRNLGKVIDTLTCGFADLMGYI

PLVGAPLGGAARALAHGVRVLEDGVNYATGNLPGCSFSIFLLALLSCLTVPASAggsgY

VGDLCGSVFLVSQLFTFSPRpYPGHITGHRMAWDMMMNWSPVCGPVYCFTPSPVVVGTT

DRTDVFLLNNTRPPLGNWFGCTWMCPTDCFRKHPEATYSRCGSGPWLTPRCLVDYPYRL

WgDRDRSELSPLLLSTTQWQVLPCSFTTLPALSTGLIHLHQNIVDVQYLYGVGSSVARV

CACLWMMLLIAQAEAALENLVKGWRLLAPITAYAQQTRGLLGCIITSLTGRDKNQVEGE

VQIVSTQSFLATCINGVCWTVYHGAGPCTCGSSDLYLVTRHADVIPVRRRGDSRGSLLS

PRPISYLKGSSGGPLLCPSGHAVGIFRAAVCTRGVAKAVDFIPVESMETTMRSPVFTDN

SSPPAVPQTFQVAHLHAPTGSGKSTKVPAAYAAQGYKVLVLNPSVAATLGFGAYMSKAH

GVsgTGVRTITTGSPITYSTYGKFLADGGCSGGAYDIIICDECHSTDATSILGIGTVLD

QAETAGARLVVLATATPPGSVTVPHPNIEEVgpgNAVAYYRGLDVSVIPTSGDVVVVAT

DALMTGFTGDFDSVIDCNTCVTQTVDFSLDPTFTIETTTLPQDAVSRTQRRGRTGRGRp gggsgggYRFVTPGERPSGMFDSSVLCECYDAGCAWYELTPAETTVRLRAYLNTPGLPV

CQDHLEFWEGVFTGLTHIDAHFLSQTKQAGDNFPYLVAYQATVCARAQAPPPSWDQMWK

CLIRLKPggkgpggKYIMTCMSADLEVVTSTWVLVGGVLAALAAYCLSTGCVVIVGRIV

LSGgpgFWAKHMWNFISGIQYLAGLSTLPGNPAIASLMAFTASVTSPLTTQpGSIGLGK

VLVDILAGYGAGVAGALVAFKIMSGEVPSTEDLVNLLPAILSPGALVVGVVCAAILRRH

VGPGEGAVQWMNRLIAFASRGNHVSPTHYVPESDAAARVTQILSSWLRDIWDWICEVLS

DFKTWLKCPCQVPSPEFFTELDGVRLHRkkgpgsgpgpRRLARGSPPSLASSSASQLSAPSLKA

TCTTNHSDAESYSSMPPLEGEPGDPDLSDGWSTVSSEAgsgsLSNSLLRHHNMVYATTS

RSAgpLTPPHSAKSKFGYGAKDVRCHsgsgggsKPARLIVFPDLGVRVCEKMALYDVVg gPMGFSYDTRCFDSTVTESDIRTEggsgggSLTERLYVGGPLTNSKGQNCGYRRCRASG

VLTTSCGNTLTCYLKASAACRAAKLggsggCTMLVCGDDLVVICESAGTQEDASLRAFT

EAMTRYSAPPGDPPQPEYDLELITSCSSNVSVAHDASGKRVYYLTRDPTTPLARAAWET

ARHTPVNSWLGNIIMYAPTLWARMILggsggEPLDLPQIIQRLHGLSAFSLHSYSPGEI

NRVAACLRKLGVPPLRAWRHRARSVRAsGGRAAICGKYLFNWAVRTKLKLTPIPAA

>GT1 & 3_short_A_TPA (SEQ ID NO: 120)

MDAMKRGLCCVLLLCGAVFVSPSQEIHARFRRkgggpgggkSTNPKPQRKTKRNTNRRP

QDVKFPGGGQIVGGVYLLPRRGPRLGVRATRKTSERSQPRGRRQPIPKARRPEGRSWAQ

PGYPWPLYGNEGCGWAGWLLSPRGSRPSWGPTDPRRRSRNLGKVIDTLTCGFADLMGYI

PLVGAPLGGAARALAHGVRVLEDGVNYATGNLPGCSFSIFLLALLSCLTVPASgkggTT

-continued

```
ELAILPCSFTPLPALSTGLIHLHQNIVDVQYLYGVGSGMMGWRLLAPITAYAQQTRGLL

GTIVTSLTGRDKNVVTGEVQVLSTAgsgPCTCGSADLYLVTRDADVIPARRRGDSTASL

LSPRPLACLKGSSGGPVMCPSGHVAGIFRAAVCTRGVAKALQFIPVETLRSPVFSDNSS

PPAVPQSYQVAHLHAPTGSGKSTKVPAAYAAQGYKVLVLNPSVAATLGFGAYMSKATGN

RTITTGAKLTYSTYGKFLADGGCSGGAYDVIICDECHAQDATSILGIGTVLDQAETAGV

RLTVLATATPPGSITVPHSNIEEVALSVIPTAGDVVVCATDALMTGFTGDFDSVIDCNV

AVEQYVDFSLDPTFSIETRTAPQDAVSRSQRRGRTGRGRLGTYRYVGPGERPSGMFDSV

VLCECYDAGCAWYELQPAETTVRLRAYLSTPGLPVCQDHLDFWESVFTGLTHIDAHFLS

QTKQQGLNFPYLTAYQATVCARAQAPPPSWDEMWKCLVRLKPTLHGPTPLLYRLGPVQN ggsgkggIGSVGLGKVLVDILAGYGAGVAGALVAFKIMSGEIPSTEDLVNLLPAILSPG

ALVVGVVCAAILRRHVGPGEGAVQWMNRLIAFASRGNHVSPTHYVPESDAAARVTAILS

SLTsgQSVVCCSMSYSWTGALITPCSAEEEKLPINPLSNSLLRHHNLVYSTSSRSASQR

QKKVTFDRLQVLDDHYKKGKRYYYLTRDPTTPLARAAWETARHTPVNSWLGNIIMYAPT

IWVRMVMgkgpgsYGATYSVTPLDLPAIIERLHGLSAFTLHSYSPVELNRVAGTLRKLG

CPPLRAWRHR

>GT1 & 3_long_D_TPA
                                                        (SEQ ID NO: 121)
MDAMKRGLCCVLLLCGAVFVSPSQEIHARFRRkgggpgggkSTNPKPQRKTKRNTNRRP

QDVKFPGGGQIVGGVYLLPRRGPRLGVRATRKTSERSQPRGRRQPIPKARRPEGRSWAQ

PGYPWPLYGNEGCGWAGWLLSPRGSRPSWGPTDPRRRSRNLGKVIDTLTCGFADLMGYI

PLVGAPLGGAARALAHGVRVLEDGVNYATGNLPGCSFSIFLLALLSCLTVPASgggsgg gVDLLVGAATMCSALYVGDMCGpHWGVLAGLAYYSMQGNWAKVSVCGPVYCFTPSPVVV GTTDRgpgsgkgpggRCGSGPWLTPRCLVDYPYRLWHYPCTAACNWTRGERCDIEDRDR SELggsgTTELAILPCSFTPLPALSTGLIHLHQNIVDVQYLYGVGSGMMGWRLLAPITA YAQQTRGLLGTIVTSLTGRDKNVVTGEVQVLSTAgsgPCTCGSADLYLVTRDADVIPAR

RRGDSTASLLSPRPLACLKGSSGGPVMCPSGHVAGIFRAAVCTRGVAKALQFIPVETLR

SPVFSDNSSPPAVPQSYQVAHLHAPTGSGKSTKVPAAYAAQGYKVLVLNPSVAATLGFG

AYMSKATGNRTITTGAKLTYSTYGKFLADGGCSGGAYDVIICDECHAQDATSILGIGTV

LDQAETAGVRLTVLATATPPGSITVPHSNIEEVALSVIPTAGDVVVCATDALMTGFTGD

FDSVIDCNVAVEQYVDFSLDPTFSIETRTAPQDAVSRSQRRGRTGRGRLGTYRYVGPGE

RPSGMFDSVVLCECYDAGCAWYELQPAETTVRLRAYLSTPGLPVCQDHLDFWESVFTGL

THIDAHFLSQTKQQGLNFPYLTAYQATVCARAQAPPPSWDEMWKCLVRLKPTLHGPTPL

LYRLGPVQNgppMACMSADLEVTTSTWVLLGGVLAALAAYCLSVGCVVIVGHFWAKHMW

NFISGIQYLAGLSTLPGNPAIASLMAFTAgpIGSVGLGKVLVDILAGYGAGVAGALVAF

KIMSGEIPSTEDLVNLLPAILSPGALVVGVVCAAILRRHVGPGEGAVQWMNRLIAFASR

GNHVSPTHYVPESDAAARVTAILSSLTCPCQVPAPEFFTEVDGVRLHRgggppgggIGS

QLPCEPEPDVSVLTSMLpTAARRLARGSPPSEASSSASQLSAPSLKATCQTHRESDSES

CSSMPPLEGEPGDPDLSCDSWSTVSDQSVVCCSMSYSWTGALITPCSAEEEKLPINPLS

NSLLRHHNLVYSTSSRSASQRQKKVTFDRLQVLDDHYKgpgPEKGGRKPARLIVYPDLG

VRVCEKMALYDVpgpgggWTSKKTPMGFSYDTRCFDSTVTEQDIRVEEEgpCGYRRCRA

SGVLTTSCGNTLTCYIKARAACggsggALRAFTEAMTRYSAPPGDAPQPggKGKRYYYL

TRDPTTPLARAAWETARHTPVNSWLGNIIMYAPTIWVRMVMgkgpgsYGATYSVTPLDL
```

-continued

PAIIERLHGLSAFTLHSYSPVELNRVAGTLRKLGCPPLRAWRHRggpggpggVRAKLLS
QGGRAAICGKYLFNWAVRTK >GT1-6_short_A_TPA (SEQ ID NO: 122)

MDAMKRGLCCVLLLCGAVFVSPSQEIHARFRRkgggpgggTKRNTNRRPMDVKFPGGGQ
IVGGVYLLPRRGPRLGVRATRKTSERSQPRGRRQPIPKARRPEGRSWAQPGYPWPLYGN
EGCGWAGWLLSPRGSRPSWGPNDPRRRSRNLGKVIDTLTCGFADLMGYIPLVGAPVGGV
ARALAHGVRALEDGINYATGNLPGCSFSIFLLALLSCLTVPASCPTDCFRKHPEATYTK
CGSGPWLTPRCLVDYPYRLWHYPCTVNFgsgLLLSTTEWQILPCSFTTLPALSTGLIHL
HQNIVDVQYLYGVGSgpPCTCGSSDLYLVTRHADVIPVRRRGDSRGSLLSPRPISYLKG
SSGGPVLCPSGHAVGIFRAAVCTRGVAKAVDFIPVESLEMRSPVFTDNSTPPAVPQTYQ
VAHLHAPTGSGKSTKVPAAYAAQGYKVLVLNPSVAATLGFGAYMSKAYGIggsRSGVRT
ITTGAPITYSTYGKFLADGGCSGGAYDIIICDECHSTDSTTILGIGTVLDQAETAGVRL
VVLATATPPGgNAVAYYRGLDVSVIPTSGDVVVVATDALMTGFTGDFDSVIDCNTCVTQ
TVDFSLDPTFTIETTTVPQDAVSRSQRRGRTGRGRRGIYRFVTPGERPSGMFDSSVLCE
CYDAGCAWYELTPAETSVRLRAYLNTPGLPVCQDHLEFWEGVFTGLTHIDAHFLSQTKQ
AGDNFPYLVAYQATVCARAQAPPPSWDQMWTHPITKYIMACMSADLEVVTSTWVLVGGV
LAALAAYCLSVGSVVIVGgpgFWAKHMWNFISGIQYLAGLSTLPGNPAIASLMAFTAAV
TSPLGAAVGSVGLGKVLVDILAGYGAGVAGALVAFKIMSGEVPSTEDLVNLLPAILSPG
ALVVGVVCAAILRRHVGPGEGAVQWMNRLIAFASRGNHVSPTHYVPESDAAARVgggsg
ggVCCSMSYSWTGALITPCAAEEEKLPINPLSNSLIRHHNMVYSTTSRSASLRQKKVTF
DRgggkgggpTPLARAAWETARHTPVNSWLGNIIMYAPTIWVRMVLMTHFFSILQgggs
ggpELNRVGACLRKLGVPPLRAWRHRARAVRAKLIAQGGKAAICGKYLFNWAV >GT1-6_long_D_TPA (SEQ ID NO: 123)

MDAMKRGLCCVLLLCGAVFVSPSQEIHARFRRkgggpgggTKRNTNRRPMDVKFPGGGQ
IVGGVYLLPRRGPRLGVRATRKTSERSQPRGRRQPIPKARRPEGRSWAQPGYPWPLYGN
EGCGWAGWLLSPRGSRPSWGPNDPRRRSRNLGKVIDTLTCGFADLMGYIPLVGAPVGGV
ARALAHGVRALEDGINYATGNLPGCSFSIFLLALLSCLTVPASpgCNCSIYPGHITGHR
MAWDMMMNWSPTTkkNGSWHINRTALNCNDSLNTGFIgpggSVCGPVYCFTPSPVVVGT
TDRgpgCPTDCFRKHPEATYTKCGSGPWLTPRCLVDYPYRLWHYPCTVNFgsgLLLSTT
EWQILPCSFTTLPALSTGLIHLHQNIVDVQYLYGVGSMGWRLLAPITAYAQQTRGLLGT
IVTSLTGRDKNPCTCGSSDLYLVTRHADVIPVRRRGDSRGSLLSPRPISYLKGSSGGPV
LCPSGHAVGIFRAAVCTRGVAKAVDFIPVESLEMRSPVFTDNSTPPAVPQTYQVAHLHA
PTGSGKSTKVPAAYAAQGYKVLVLNPSVAATLGFGAYMSKAYGIggsRSGVRTITTGAP
ITYSTYGKFLADGGCSGGAYDIIICDECHSTDSTTILGIGTVLDQAETAGVRLVVLATA
TPPGgkggkgIKGGRHLIFCHSKKKCDELAgpgNAVAYYRGLDVSVIPTSGDVVVVATD
ALMTGFTGDFDSVIDCNTCVTQTVDFSLDPTFTIETTTVPQDAVSRSQRRGRTGRGRRG
IYRFVTPGERPSGMFDSSVLCECYDAGCAWYELTPAETSVRLRAYLNTPGLPVCQDHLE
FWEGVFTGLTHIDAHFLSQTKQAGDNFPYLVAYQATVCARAQAPPPSWDQMWTHPITKY
IMACMSADLEVVTSTWVLVGGVLAALAAYCLSVGSVVIVGgpgFWAKHMWNFISGIQYL
AGLSTLPGNPAIASLMAFTAAVTSPLGAAVGSVGLGKVLVDILAGYGAGVAGALVAFKI

```
MSGEVPSTEDLVNLLPAILSPGALVVGVVCAAILRRHVGPGEGAVQWMNRLIAFASRGN

HVSPTHYVPESDAAARVgpTAETAARRLARGSPPSLASSSASQLSAPSLKATCTVCCSM

SYSWTGALITPCAAEEEKLPINPLSNSLIRHHNMVYSTTSRSASLRQKKVTFDRggsgg pgPSKGGRKPARLIVYPDLGVRVCEKRALYDVpggpKKTPMGFSYDTRCFDSTVTERDI RTEgggpggCGYRRCRASGVLTTSMGNTITCYIKALAAEAMTRYSAPPGDPPQPEYDLE LITSCSSNVSVAHDggsggTPLARAAWETARHTPVNSWLGNIIMYAPTIWVRMVLMTHF FSILQggpgYGATYSVTPLDLPAIIERLHGLSAFTLHSYSggpggpELNRVGACLRKLG

VPPLRAWRHRARAVRAKLIAQGGKAAICGKYLFNWAV

>GT1-6_long_D_Nolinkers
                                                        (SEQ ID NO: 124)
MDAMKRGLCCVLLLCGAVFVSPSQEIHARFRRkgggpgggTKRNTNRRPMDVKFPGGGQ

IVGGVYLLPRRGPRLGVRATRKTSERSQPRGRRQPIPKARRPEGRSWAQPGYPWPLYGN

EGCGWAGWLLSPRGSRPSWGPNDPRRRSRNLGKVIDTLTCGFADLMGYIPLVGAPVGGV

ARALAHGVRALEDGINYATGNLPGCSFSIFLLALLSCLTVPASCNCSIYPGHITGHRMA

WDMMMNWSPTTNGSWHINRTALNCNDSLNTGFISVCGPVYCFTPSPVVVGTTDRCPTDC

FRKHPEATYTKCGSGPWLTPRCLVDYPYRLWHYPCTVNFLLLSTTEWQILPCSFTTLPA

LSTGLIHLHQNIVDVQYLYGVGSMGWRLLAPITAYAQQTRGLLGTIVTSLTGRDKNPCT

CGSSDLYLVTRHADVIPVRRRGDSRGSLLSPRPISYLKGSSGGPVLCPSGHAVGIFRAA

VCTRGVAKAVDFIPVESLEMRSPVFTDNSTPPAVPQTYQVAHLHAPTGSGKSTKVPAAY

AAQGYKVLVLNPSVAATLGFGAYMSKAYGIRSGVRTITTGAPITYSTYGKFLADGGCSG

GAYDIIICDECHSTDSTTILGIGTVLDQAETAGVRLVVLATATPPGIKGGRHLIFCHSK

KKCDELANAVAYYRGLDVSVIPTSGDVVVVATDALMTGFTGDFDSVIDCNTCVTQTVDF

SLDPTFTIETTTVPQDAVSRSQRRGRTGRGRRGIYRFVTPGERPSGMFDSSVLCECYDA

GCAWYELTPAETSVRLRAYLNTPGLPVCQDHLEFWEGVFTGLTHIDAHFLSQTKQAGDN

FPYLVAYQATVCARAQAPPPSWDQMWTHPITKYIMACMSADLEVVTSTWVLVGGVLAAL

AAYCLSVGSVVIVGFWAKHMWNFISGIQYLAGLSTLPGNPAIASLMAFTAAVTSPLGAA

VGSVGLGKVLVDILAGYGAGVAGALVAFKIMSGEVPSTEDLVNLLPAILSPGALVVGVV

CAAILRRHVGPGEGAVQWMNRLIAFASRGNHVSPTHYVPESDAAARVTAETAARRLARG

SPPSLASSSASQLSAPSLKATCTVCCSMSYSWTGALITPCAAEEEKLPINPLSNSLIRH

HNMVYSTTSRSASLRQKKVTFDRPSKGGRKPARLIVYPDLGVRVCEKRALYDVKKTPMG

FSYDTRCFDSTVTERDIRTECGYRRCRASGVLTTSMGNTITCYIKALAAEAMTRYSAPP

GDPPQPEYDLELITSCSSNVSVAHDTPLARAAWETARHTPVNSWLGNIIMYAPTIWVRM

VLMTHFFSILQYGATYSVTPLDLPAIIERLHGLSAFTLHSYSELNRVGACLRKLGVPPL

RAWRHRARAVRAKLIAQGGKAAICGKYLFNWAV

>GT1-6_long_D_Non-TPA_linkers
                                                        (SEQ ID NO: 125)
MTKRNTNRRPMDVKFPGGGQIVGGVYLLPRRGPRLGVRATRKTSERSQPRGRRQPIPKA

RRPEGRSWAQPGYPWPLYGNEGCGWAGWLLSPRGSRPSWGPNDPRRRSRNLGKVIDTLT

CGFADLMGYIPLVGAPVGGVARALAHGVRALEDGINYATGNLPGCSFSIFLLALLSCLT

VPASpgCNCSIYPGHITGHRMAWDMMMNWSPTTkkNGSWHINRTALNCNDSLNTGFIgp ggSVCGPVYCFTPSPVVVGTTDRgpgCPTDCFRKHPEATYTKCGSGPWLTPRCLVDYPY RLWHYPCTVNFgsgLLLSTTEWQILPCSFTTLPALSTGLIHLHQNIVDVQYLYGVGSMG

WRLLAPITAYAQQTRGLLGTIVTSLTGRDKNPCTCGSSDLYLVTRHADVIPVRRRGDSR
```

-continued

GSLLSPRPISYLKGSSGGPVLCPSGHAVGIFRAAVCTRGVAKAVDFIPVESLEMRSPVF
TDNSTPPAVPQTYQVAHLHAPTGSGKSTKVPAAYAAQGYKVLVLNPSVAATLGFGAYMS
KAYGIggsRSGVRTITTGAPITYSTYGKFLADGGCSGGAYDIIICDECHSTDSTTILGI
GTVLDQAETAGVRLVVLATATPPGgkggkgIKGGRHLIFCHSKKKCDELAgpgNAVAYY
RGLDVSVIPTSGDVVVVATDALMTGFTGDFDSVIDCNTCVTQTVDFSLDPTFTIETTTV
PQDAVSRSQRRGRTGRGRRGIYRFVTPGERPSGMFDSSVLCECYDAGCAWYELTPAETS
VRLRAYLNTPGLPVCQDHLEFWEGVFTGLTHIDAHFLSQTKQAGDNFPYLVAYQATVCA
RAQAPPPSWDQMWTHPITKYIMACMSADLEVVTSTWVLVGGVLAALAAYCLSVGSVVIV
GgpgFWAKHMWNFISGIQYLAGLSTLPGNPAIASLMAFTAAVTSPLGAAVGSVGLGKVL
VDILAGYGAGVAGALVAFKIMSGEVPSTEDLVNLLPAILSPGALVVGVVCAAILRRHVG
PGEGAVQWMNRLIAFASRGNHVSPTHYVPESDAAARVgpTAETAARRLARGSPPSLASS
SASQLSAPSLKATCTVCCSMSYSWTGALITPCAAEEEKLPINPLSNSLIRHHNMVYSTT
SRSASLRQKKVTFDRggsggpgPSKGGRKPARLIVYPDLGVRVCEKRALYDVpggpKKT
PMGFSYDTRCFDSTVTERDIRTEgggpggCGYRRCRASGVLTTSMGNTITCYIKALAAE
AMTRYSAPPGDPPQPEYDLELITSCSSNVSVAHDggsggTPLARAAWETARHTPVNSWL
GNIIMYAPTIWVRMVLMTHFFSILQggpgYGATYSVTPLDLPAIIERLHGLSAFTLHSY
SggpggpELNRVGACLRKLGVPPLRAWRHRARAVRAKLIAQGGKAAICGKYLFNWAV Summary of Conserved Sequences in Each Example Embodiment

| GT1 long | |
|---|---|
| 1-192 | SEQ ID NO: 1 |
| 276-297 | SEQ ID NO: 2 |
| 309-329 | SEQ ID NO: 3 |
| 502-522 | SEQ ID NO: 4 |
| 534-556 | SEQ ID NO: 5 |
| 581-617 | SEQ ID NO: 6 |
| 656-710 | SEQ ID NO: 7/8 |
| 729-753 | SEQ ID NO: 9 |
| 1021-1065 | SEQ ID NO: 10/11 |
| 1067-1087 | SEQ ID NO: 12 |
| 1122-1275 | SEQ ID NO: 13/14 |
| 1280-1366 | SEQ ID NO: 15/16 |
| 1413-1496 | SEQ ID NO: 17 |
| 1499-1617 | SEQ ID NO: 18/19 |
| 1643-1691 | SEQ ID NO: 20 |
| 1760-1805 | SEQ ID NO: 21/22 |
| 1840-1950 | SEQ ID NO: 23 |
| 1975-1997 | SEQ ID NO: 24 |
| 2112-2133 | SEQ ID NO: 25 |
| 2188-2220 | SEQ ID NO: 26 |
| 2380-2413 | SEQ ID NO: 27/28 |
| 2445-2465 | SEQ ID NO: 29 |
| 2511-2532 | SEQ ID NO: 30 |
| 2575-2600 | SEQ ID NO: 31 |
| 2634-2657 | SEQ ID NO: 32 |
| 2675-2729 | SEQ ID NO: 33 |
| 2731-2754 | SEQ ID NO: 34 |
| 2755-2846 | SEQ ID NO: 35/36 |
| 2875-2930 | SEQ ID NO: 37 |
| 2935-2963 | SEQ ID NO: 38 |

| GT1 short | |
|---|---|
| 1-192 | SEQ ID NO: 1 |
| 656-710 | SEQ ID NO: 7/8 |
| 1122-1275 | SEQ ID NO: 13/14 |
| 1280-1366 | SEQ ID NO: 15/16 |
| 1413-1496 | SEQ ID NO: 17 |
| 1499-1617 | SEQ ID NO: 18/19 |
| 1643-1691 | SEQ ID NO: 20 |
| 1840-1950 | SEQ ID NO: 23 |
| 2675-2729 | SEQ ID NO: 33 |
| 2755-2846 | SEQ ID NO: 35/36 |
| 2875-2930 | SEQ ID NO: 37 |

| GT1/3 long | |
|---|---|
| 1-191 | SEQ ID NO: 39/40 |
| 262-283 | SEQ ID NO: 41/42 |
| 352-372 | SEQ ID NO: 43 |
| 503-524 | SEQ ID NO: 44 |
| 603-629 | SEQ ID NO: 45 |
| 649-670 | SEQ ID NO: 46 |
| 676-717 | SEQ ID NO: 47 |
| 1028-1073 | SEQ ID NO: 48/49 |
| 1129-1209 | SEQ ID NO: 50/51 |
| 1213-1379 | SEQ ID NO: 52/53 |
| 1287-1375 | SEQ ID NO: 54/55 |
| 1431-1641 | SEQ ID NO: 56/57 |
| 1653-1693 | SEQ ID NO: 58/59 |
| 1767-1803 | SEQ ID NO: 60 |
| 1846-1960 | SEQ ID NO: 61/62 |
| 2119-2140 | SEQ ID NO: 63 |
| 2163-2183 | SEQ ID NO: 64 |
| 2192-2227 | SEQ ID NO: 65/66 |
| 2391-2423 | SEQ ID NO: 67/68 |
| 2427-2498 | SEQ ID NO: 69/70 |
| 2581-2611 | SEQ ID NO: 71 |
| 2640-2671 | SEQ ID NO: 72 |
| 2706-2736 | SEQ ID NO: 73/74 |
| 2767-2789 | SEQ ID NO: 75 |
| 2809-2858 | SEQ ID NO: 76/77 |
| 2880-2936 | SEQ ID NO: 78/79 |
| 2939-2966 | SEQ ID NO: 80 |

| GT1/3 short | |
|---|---|
| 1-191 | SEQ ID NO: 39/40 |
| 676-717 | SEQ ID NO: 47 |
| 1028-1073 | SEQ ID NO: 48/49 |
| 1129-1209 | SEQ ID NO: 50/51 |
| 1213-1379 | SEQ ID NO: 52/53 |
| 1287-1375 | SEQ ID NO: 54/55 |

| | |
|---|---|
| 1431-1641 | SEQ ID NO: 56/57 |
| 1846-1960 | SEQ ID NO: 61/62 |
| 2427-2498 | SEQ ID NO: 69/70 |
| 2809-2858 | SEQ ID NO: 76/77 |
| 2880-2936 | SEQ ID NO: 78/79 |
| GT1-6 long | |
| 11-191 | SEQ ID NO: 81/82 |
| 304-331 | SEQ ID NO: 83 |
| 417-439 | SEQ ID NO: 84 |
| 503-524 | SEQ ID NO: 44 |
| 588-632 | SEQ ID NO: 85 |
| 672-715 | SEQ ID NO: 86/87 |
| 1028-1061 | SEQ ID NO: 88/89 |
| 1129-1210 | SEQ ID NO: 90/91 |
| 1212-1282 | SEQ ID NO: 92/93 |
| 1286-1361 | SEQ ID NO: 94/95 |
| 1392-1412 | SEQ ID NO: 96 |
| 1420-1616 | SEQ ID NO: 97/98 |
| 1645-1692 | SEQ ID NO: 99/100 |
| 1767-1809 | SEQ ID NO: 101/102 |
| 1843-1952 | SEQ ID NO: 103/104 |
| 2189-2224 | SEQ ID NO: 105 |
| 2453-2512 | SEQ ID NO: 106/107 |
| 2604-2634 | SEQ ID NO: 108 |
| 2666-2692 | SEQ ID NO: 109 |
| 2729-2758 | SEQ ID NO: 110/111 |
| 2796-2831 | SEQ ID NO: 112 |
| 2845-2890 | SEQ ID NO: 113 |
| 2903-2934 | SEQ ID NO: 114/115 |
| 2936-2986 | SEQ ID NO: 116/117 |
| GT1-6 short | |
| 11-191 | SEQ ID NO: 81/82 |
| 588-632 | SEQ ID NO: 85 |
| 672-715 | SEQ ID NO: 86/87 |
| 1129-1210 | SEQ ID NO: 90/91 |
| 1212-1282 | SEQ ID NO: 92/93 |
| 1286-1361 | SEQ ID NO: 94/95 |
| 1420-1616 | SEQ ID NO: 97/98 |
| 1645-1692 | SEQ ID NO: 99/100 |
| 1767-1809 | SEQ ID NO: 101/102 |
| 1843-1952 | SEQ ID NO: 103/104 |
| 2453-2512 | SEQ ID NO: 106/107 |
| 2936-2986 | SEQ ID NO: 116/117 |

Conserved Peptide Sequences Produced from Alignments of GT1/GT1 and 3/GT1-6:

```
                                      SEQ ID NO: 126
TKRNTNRRPQDVKFPGGGQIVGGVYLLPRRGPRLGVRATRKTSERSQPR

GRRQPIPKARRPEGR(T/S)WAQPGYPWPLYGNEGCGWAGWLLSPRGSR

PSWGP(T/N)DPRRRSRNLGKVIDTLTCGFADLMGYIPLVGAP(L/V)G

G(A/V)ARALAHGVR(V/A)LEDG(V/I)N(Y/F)ATGNLPGCSFSIFL

LALLSCLT(V/H)PAS

SEQ ID NO: 127
VCGPVYCFTPSPVVVGTTDR

SEQ ID NO: 128
(R/K)CGSGPWLTPRCLVDYPYRLW

SEQ ID NO: 129
TTE(W/L)(Q/A)(V/I)LPCSFT(T/P)LPALSTGLIHLHQNIVDVQY

LYGVGS

SEQ ID NO: 130
(Q/M/K)GWRLLAPITAYAQQTRGLLG(C/T)I(I/V)TSLTGRDKN

SEQ ID NO: 131
PCTCGSSDLYLVTRHADVIP(V/A)RRRGDSR(G/A)SLLSPRP(I/L)

(S/A)(Y/T)LKGSSGGP(L/V)LCPSGH(A/V)(A/V)GIFRAAVCTR

GVAKA(V/L)(D/Q)FIPVE(S/T)L

SEQ ID NO: 132
RSP(V/S)F(T/S)DNS(S/T)PPAVPQ(T/S)(F/Y)QV(A/G)HLHA

PTGSGKSTKVPAAYAAQGYKVLVLNPSVAATLGFGAYMSKA

SEQ ID NO: 133
TG(V/N)RT(I/V)TTGA(P/K)ITYSTYGKFLADGGCSGGAYDIIICD

ECHS(T/Q)DAT(S/T)ILGIGTVLDQAETAG(A/V)RL(V/T)VLATA

TPPG

SEQ ID NO: 134
SVIPTSGDVVV(V/C)ATDALMTGFTGDFDSVIDCN(T/V)(C/A)V (T/E)QTVDFSLDPTF(T/S)IETTT(L/A)PQDAVSR(T/S)QRRG

RTGRGR

SEQ ID NO: 135
YR(F/Y)V(T/S)PGERPSGMFDS(S/V)VLCECYDAGCAWYEL(T/Q)

PAETTVRLRAYLNTPGLPVCQDHLEFWE(G/S)VFTGLTHIDAHFLSQ

TKQ(A/Q/G)G(E/L)NFPYLVAYQATVCARA(Q/K)APPPSWD(Q/

E/T)MW

SEQ ID NO: 136
M(T/A)CMSADLEV(V/T)TSTWVL(V/L)GGVLAALAAYCLS(T/V)G

CVVIVG

SEQ ID NO: 137
FWAKHMWNFISGIQYLAGLSTLPGNPA(I/V)ASLMAFTA

SEQ ID NO: 138
GSIGLGKVLVDILAGYGAGVAGALVAFKIM(S/G)GE(V/L/K)PSTED (L/M)VNLLPAILSPGALVVGVVCAAILRRHVGPGEGAVQWMNRLIAFA

SRGNHVSPTHYVPESDAAARV

SEQ ID NO: 139
RRLARGSPPS(L/E)ASSSASQLSAPSLKATC(T/Q)

SEQ ID NO: 140
ES(Y/C)SSMPPLEGEPGDPDL(S/E)(D/F)(G/E)(S/Q)(W/V)

(S/E)(T/S)(V/Q)

SEQ ID NO: 141
LSNSLLRHHN(M/L)VY(A/S)T(T/S)SRSA

SEQ ID NO: 142
KPARLIV(F/Y)PDLGVRVCEK(M/R)ALYDV

SEQ ID NO: 143
PMGFSYDTRCFDSTVTE(S/Q/R)DIR(T/V)E

SEQ ID NO: 144
CGYRRCRASGVL(T/P)TS(C/M)GNTLTCY(L/I)KA(S/T/L)AA

SEQ ID NO: 145
EAMTRYSAPPGD(P/A)PQP

SEQ ID NO: 146
TPLARAAWETARHTPVNSWLGNIIM(F/Y)APT(L/I)W(A/V)RM (I/V)L

SEQ ID NO: 147
(E/T)PLDLP(Q/A)II(Q/E)RLHGLSAFSLHSYS
```

-continued

SEQ ID NO: 148
E(I/L)NRVA(A/G)CLRKLG(V/C)PPLRAWRHR

SEQ ID NO: 149
GGRAAICGKYLFNWAV

With reference to SEQ ID NOs: 126-149, the residues placed in parentheses are intended to be provided as options, such that one residue within the parentheses is selected. In one embodiment where the option is between two residues, the first option is selected in any given sequence. In another embodiment where the option is between two residues the second option is selected in any given sequence.

44 Conserved Peptide Sequences that are 100% Conserved Across HCV1-6 and Useful as an Epitope:

(SEQ ID NO: 150)
TKRNTNRRPQDVKFPGGGQIVGGVYLLPRRGPRLGVRATRKTSERSQPRG

RRQPIPKARRPEGR (SEQ ID NO: 151)
WAQPGYPWPLYGNEGCGWAGWLLSPRGSRPSWGP (SEQ ID NO: 152)
DPRRRSRNLGKVIDTLTCGFADLMGYIPLVGAP (SEQ ID NO: 153)
ARALAHGVR (SEQ ID NO: 154)
ATGNLPGCSFSIFLLALLSCLT (SEQ ID NO: 155)
VCGPVYCFTPSPVVVGTTDR (SEQ ID NO: 156)
CGSGPWLTPRCLVDYPYRLW (SEQ ID NO: 157)
LPALSTGLIHLHQNIVDVQYLYGVGS (SEQ ID NO: 158)
GWRLLAPITAYAQQTRGLLG (SEQ ID NO: 159)
TSLTGRDKN (SEQ ID NO: 160)
PCTCGSSDLYLVTRHADVIP (SEQ ID NO: 161)
LKGSSGGP (SEQ ID NO: 162)
GIFRAAVCTRGVAKA (SEQ ID NO: 163)
HLHAPTGSGKSTKVPAAYAAQGYKVLVLNPSVAATLGFGAYMSKA (SEQ ID NO: 164)
ITYSTYGKFLADGGCSGGAYDIIICDECHS (SEQ ID NO: 165)
ILGIGTVLDQAETAG (SEQ ID NO: 166)
VLATATPPG (SEQ ID NO: 167)
SVIPTSGDVVV (SEQ ID NO: 168)
ATDALMTGFTGDFDSVIDCN (SEQ ID NO: 169)
QTVDFSLDPTF

-continued (SEQ ID NO: 170)
QRRGRTGRGR (SEQ ID NO: 171)
PGERPSGMFDS (SEQ ID NO: 172)
VLCECYDAGCAWYEL (SEQ ID NO: 173)
PAETTVRLRAYLNTPGLPVCQDHLEFWE (SEQ ID NO: 174)
VFTGLTHIDAHFLSQTKQ (SEQ ID NO: 175)
NFPYLVAYQATVCARA (SEQ ID NO: 176)
CMSADLEV (SEQ ID NO: 177)
GGVLAALAAYCLS (SEQ ID NO: 178)
FWAKHMWNFISGIQYLAGLSTLPGNPA (SEQ ID NO: 179)
ASLMAFTA (SEQ ID NO: 180)
GSIGLGKVLVDILAGYGAGVAGALVAFKIM (SEQ ID NO: 181)
VNLLPAILSPGALVVGVVCAAILRRHVGPGEGAVQWMNRLIAFASRGNHV

SPTHYVPESDAAARV (SEQ ID NO: 182)
RRLARGSPPS (SEQ ID NO: 183)
ASSSASQLSAPSLKATC (SEQ ID NO: 184)
SSMPPLEGEPGDPDL (SEQ ID NO: 185)
LSNSLLRHH (SEQ ID NO: 186)
PDLGVRVCEK (SEQ ID NO: 187)
PMGFSYDTRCFDSTVTE (SEQ ID NO: 188)
CGYRRCRASGVL (SEQ ID NO: 189)
EAMTRYSAPPGD (SEQ ID NO: 190)
TPLARAAWETARHTPVNSWLGNIIM (SEQ ID NO: 191)
RLHGLSAFSLHSYS (SEQ ID NO: 192)
PPLRAWRHR (SEQ ID NO: 193)
GGRAAICGKYLFNWAV

The invention claimed is:

1. A nucleic acid encoding a fusion polypeptide comprising a plurality of conserved peptide sequences, wherein at least one of the conserved sequences is conserved across:
   i) HCV genotypes 1a and 1b;
   ii) HCV genotypes 1 and 3; or
   iii) HCV genotypes 1 to 6; and
   wherein at least one of the conserved peptide sequences comprises at least part of a sequence of a non-structural protein of the HCV genotypes, and wherein at least one of the conserved sequences is selected from SEQ ID NO: 118-125.

2. The nucleic acid according to claim 1, wherein the plurality of conserved peptide sequences comprise 5 or more conserved peptide sequences.

3. The nucleic acid according to claim 1, wherein the conserved peptide sequences are not distanced apart by more than 10 residues in the polypeptide sequence.

4. The nucleic acid according to claim 1, wherein two or more, or all, of the plurality of conserved peptide sequences are directly joined together in the polypeptide.

5. The nucleic acid according to claim 1, wherein some or all of the conserved peptide sequences are derived from non-structural HCV proteins.

6. The nucleic acid according to claim 1, wherein
   the polypeptide comprises or consists of the sequence of any one of SEQ ID NOs: 118 to 125 without the TPA peptide adjuvant, or with an alternative peptide adjuvant.

7. The nucleic acid according to claim 1, wherein the nucleic acid further encodes a peptide adjuvant.

8. The nucleic acid according to claim 1, wherein the nucleic acid is a viral vector.

9. A composition comprising the nucleic acid according to claim 1.

10. A method of treatment of HCV infection comprising the administration of:
    the nucleic acid according to claim 1; or
    a composition comprising the nucleic acid according to claim 1.

* * * * *

SEQUENCE LISTING

<160> NUMBER OF SEQ ID NOS: 195

<210> SEQ ID NO 1
<211> LENGTH: 191
<212> TYPE: PRT
<213> ORGANISM: Homo sapiens

<400> SEQUENCE: 1

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190

<210> SEQ ID NO 2
<211> LENGTH: 21
<212> TYPE: PRT
<213> ORGANISM: Homo sapiens

<400> SEQUENCE: 2

Tyr Val Gly Asp Leu Cys Gly Ser Val Phe Leu Val Ser Gln Leu Phe
1               5                   10                  15

Thr Phe Ser Pro Arg
            20

<210> SEQ ID NO 3
<211> LENGTH: 20
<212> TYPE: PRT
<213> ORGANISM: Homo sapiens

<400> SEQUENCE: 3

Tyr Pro Gly His Ile Thr Gly His Arg Met Ala Trp Asp Met Met Met
1               5                   10                  15

Asn Trp Ser Pro
            20

<210> SEQ ID NO 4
<211> LENGTH: 20
<212> TYPE: PRT
<213> ORGANISM: Homo sapiens

```
<400> SEQUENCE: 4

Val Cys Gly Pro Val Tyr Cys Phe Thr Pro Ser Pro Val Val Gly
1               5                   10                  15

Thr Thr Asp Arg
            20

<210> SEQ ID NO 5
<211> LENGTH: 22
<212> TYPE: PRT
<213> ORGANISM: Homo sapiens

<400> SEQUENCE: 5

Thr Asp Val Phe Leu Leu Asn Asn Thr Arg Pro Pro Leu Gly Asn Trp
1               5                   10                  15

Phe Gly Cys Thr Trp Met
            20

<210> SEQ ID NO 6
<211> LENGTH: 36
<212> TYPE: PRT
<213> ORGANISM: Homo sapiens

<400> SEQUENCE: 6

Cys Pro Thr Asp Cys Phe Arg Lys His Pro Glu Ala Thr Tyr Ser Arg
1               5                   10                  15

Cys Gly Ser Gly Pro Trp Leu Thr Pro Arg Cys Leu Val Asp Tyr Pro
            20                  25                  30

Tyr Arg Leu Trp
        35

<210> SEQ ID NO 7
<211> LENGTH: 54
<212> TYPE: PRT
<213> ORGANISM: Homo sapiens

<400> SEQUENCE: 7

Asp Arg Asp Arg Ser Glu Leu Ser Pro Leu Leu Leu Ser Thr Thr Glu
1               5                   10                  15

Trp Gln Val Leu Pro Cys Ser Phe Thr Thr Leu Pro Ala Leu Ser Thr
            20                  25                  30

Gly Leu Ile His Leu His Gln Asn Ile Val Asp Val Gln Tyr Leu Tyr
        35                  40                  45

Gly Val Gly Ser Ser Val
    50

<210> SEQ ID NO 8
<211> LENGTH: 54
<212> TYPE: PRT
<213> ORGANISM: Homo sapiens

<400> SEQUENCE: 8

Asp Arg Asp Arg Ser Glu Leu Ser Pro Leu Leu Leu Ser Thr Thr Gln
1               5                   10                  15

Trp Gln Val Leu Pro Cys Ser Phe Thr Thr Leu Pro Ala Leu Ser Thr
            20                  25                  30

Gly Leu Ile His Leu His Gln Asn Ile Val Asp Val Gln Tyr Leu Tyr
        35                  40                  45

Gly Val Gly Ser Ser Val
    50
```

```
<210> SEQ ID NO 9
<211> LENGTH: 24
<212> TYPE: PRT
<213> ORGANISM: Homo sapiens

<400> SEQUENCE: 9

Ala Arg Val Cys Ala Cys Leu Trp Met Met Leu Leu Ile Ala Gln Ala
1               5                   10                  15

Glu Ala Ala Leu Glu Asn Leu Val
            20

<210> SEQ ID NO 10
<211> LENGTH: 44
<212> TYPE: PRT
<213> ORGANISM: Homo sapiens

<400> SEQUENCE: 10

Gln Gly Trp Arg Leu Leu Ala Pro Ile Thr Ala Tyr Ala Gln Gln Thr
1               5                   10                  15

Arg Gly Leu Leu Gly Cys Ile Ile Thr Ser Leu Thr Gly Arg Asp Lys
            20                  25                  30

Asn Gln Val Glu Gly Glu Val Gln Ile Val Ser Thr
        35                  40

<210> SEQ ID NO 11
<211> LENGTH: 44
<212> TYPE: PRT
<213> ORGANISM: Homo sapiens

<400> SEQUENCE: 11

Lys Gly Trp Arg Leu Leu Ala Pro Ile Thr Ala Tyr Ala Gln Gln Thr
1               5                   10                  15

Arg Gly Leu Leu Gly Cys Ile Ile Thr Ser Leu Thr Gly Arg Asp Lys
            20                  25                  30

Asn Gln Val Glu Gly Glu Val Gln Ile Val Ser Thr
        35                  40

<210> SEQ ID NO 12
<211> LENGTH: 20
<212> TYPE: PRT
<213> ORGANISM: Homo sapiens

<400> SEQUENCE: 12

Gln Ser Phe Leu Ala Thr Cys Ile Asn Gly Val Cys Trp Thr Val Tyr
1               5                   10                  15

His Gly Ala Gly
            20

<210> SEQ ID NO 13
<211> LENGTH: 153
<212> TYPE: PRT
<213> ORGANISM: Homo sapiens

<400> SEQUENCE: 13

Pro Cys Thr Cys Gly Ser Ser Asp Leu Tyr Leu Val Thr Arg His Ala
1               5                   10                  15

Asp Val Ile Pro Val Arg Arg Arg Gly Asp Ser Arg Gly Ser Leu Leu
            20                  25                  30

Ser Pro Arg Pro Ile Ser Tyr Leu Lys Gly Ser Ser Gly Gly Pro Leu
        35                  40                  45
```

-continued

```
Leu Cys Pro Ser Gly His Ala Val Gly Ile Phe Arg Ala Ala Val Cys
 50                  55                  60

Thr Arg Gly Val Ala Lys Ala Val Asp Phe Ile Pro Val Glu Ser Leu
 65                  70                  75                  80

Glu Thr Thr Met Arg Ser Pro Val Phe Thr Asp Asn Ser Ser Pro Pro
                 85                  90                  95

Ala Val Pro Gln Thr Phe Gln Val Ala His Leu His Ala Pro Thr Gly
                100                 105                 110

Ser Gly Lys Ser Thr Lys Val Pro Ala Ala Tyr Ala Ala Gln Gly Tyr
            115                 120                 125

Lys Val Leu Val Leu Asn Pro Ser Val Ala Ala Thr Leu Gly Phe Gly
        130                 135                 140

Ala Tyr Met Ser Lys Ala His Gly Val
145                 150

<210> SEQ ID NO 14
<211> LENGTH: 153
<212> TYPE: PRT
<213> ORGANISM: Homo sapiens

<400> SEQUENCE: 14

Pro Cys Thr Cys Gly Ser Ser Asp Leu Tyr Leu Val Thr Arg His Ala
  1               5                  10                  15

Asp Val Ile Pro Val Arg Arg Arg Gly Asp Ser Arg Gly Ser Leu Leu
                 20                  25                  30

Ser Pro Arg Pro Ile Ser Tyr Leu Lys Gly Ser Ser Gly Gly Pro Leu
             35                  40                  45

Leu Cys Pro Ser Gly His Ala Val Gly Ile Phe Arg Ala Ala Val Cys
 50                  55                  60

Thr Arg Gly Val Ala Lys Ala Val Asp Phe Ile Pro Val Glu Ser Met
 65                  70                  75                  80

Glu Thr Thr Met Arg Ser Pro Val Phe Thr Asp Asn Ser Ser Pro Pro
                 85                  90                  95

Ala Val Pro Gln Thr Phe Gln Val Ala His Leu His Ala Pro Thr Gly
                100                 105                 110

Ser Gly Lys Ser Thr Lys Val Pro Ala Ala Tyr Ala Ala Gln Gly Tyr
            115                 120                 125

Lys Val Leu Val Leu Asn Pro Ser Val Ala Ala Thr Leu Gly Phe Gly
        130                 135                 140

Ala Tyr Met Ser Lys Ala His Gly Val
145                 150

<210> SEQ ID NO 15
<211> LENGTH: 86
<212> TYPE: PRT
<213> ORGANISM: Homo sapiens

<400> SEQUENCE: 15

Thr Gly Val Arg Thr Ile Thr Thr Gly Ala Pro Ile Thr Tyr Ser Thr
  1               5                  10                  15

Tyr Gly Lys Phe Leu Ala Asp Gly Gly Cys Ser Gly Gly Ala Tyr Asp
                 20                  25                  30

Ile Ile Ile Cys Asp Glu Cys His Ser Thr Asp Ala Thr Ser Ile Leu
             35                  40                  45

Gly Ile Gly Thr Val Leu Asp Gln Ala Glu Thr Ala Gly Ala Arg Leu
 50                  55                  60
```

-continued

Val Val Leu Ala Thr Ala Thr Pro Pro Gly Ser Val Thr Val Pro His
65                  70                  75                  80

Pro Asn Ile Glu Glu Val
                85

<210> SEQ ID NO 16
<211> LENGTH: 86
<212> TYPE: PRT
<213> ORGANISM: Homo sapiens

<400> SEQUENCE: 16

Thr Gly Val Arg Thr Ile Thr Thr Gly Ser Pro Ile Thr Tyr Ser Thr
1               5                   10                  15

Tyr Gly Lys Phe Leu Ala Asp Gly Gly Cys Ser Gly Gly Ala Tyr Asp
                20                  25                  30

Ile Ile Ile Cys Asp Glu Cys His Ser Thr Asp Ala Thr Ser Ile Leu
            35                  40                  45

Gly Ile Gly Thr Val Leu Asp Gln Ala Glu Thr Ala Gly Ala Arg Leu
        50                  55                  60

Val Val Leu Ala Thr Ala Thr Pro Pro Gly Ser Val Thr Val Pro His
65                  70                  75                  80

Pro Asn Ile Glu Glu Val
                85

<210> SEQ ID NO 17
<211> LENGTH: 83
<212> TYPE: PRT
<213> ORGANISM: Homo sapiens

<400> SEQUENCE: 17

Asn Ala Val Ala Tyr Tyr Arg Gly Leu Asp Val Ser Val Ile Pro Thr
1               5                   10                  15

Ser Gly Asp Val Val Val Ala Thr Asp Ala Leu Met Thr Gly Phe
                20                  25                  30

Thr Gly Asp Phe Asp Ser Val Ile Asp Cys Asn Thr Cys Val Thr Gln
            35                  40                  45

Thr Val Asp Phe Ser Leu Asp Pro Thr Phe Thr Ile Glu Thr Thr Thr
        50                  55                  60

Leu Pro Gln Asp Ala Val Ser Arg Thr Gln Arg Arg Gly Arg Thr Gly
65                  70                  75                  80

Arg Gly Arg

<210> SEQ ID NO 18
<211> LENGTH: 118
<212> TYPE: PRT
<213> ORGANISM: Homo sapiens

<400> SEQUENCE: 18

Tyr Arg Phe Val Thr Pro Gly Glu Arg Pro Ser Gly Met Phe Asp Ser
1               5                   10                  15

Ser Val Leu Cys Glu Cys Tyr Asp Ala Gly Cys Ala Trp Tyr Glu Leu
                20                  25                  30

Thr Pro Ala Glu Thr Thr Val Arg Leu Arg Ala Tyr Leu Asn Thr Pro
            35                  40                  45

Gly Leu Pro Val Cys Gln Asp His Leu Glu Phe Trp Glu Gly Val Phe
        50                  55                  60

Thr Gly Leu Thr His Ile Asp Ala His Phe Leu Ser Gln Thr Lys Gln

```
                 65                   70                   75                   80
Ala Gly Glu Asn Phe Pro Tyr Leu Val Ala Tyr Gln Ala Thr Val Cys
                     85                   90                   95

Ala Arg Ala Gln Ala Pro Pro Ser Trp Asp Gln Met Trp Lys Cys
                100                 105                 110

Leu Ile Arg Leu Lys Pro
            115

<210> SEQ ID NO 19
<211> LENGTH: 118
<212> TYPE: PRT
<213> ORGANISM: Homo sapiens

<400> SEQUENCE: 19

Tyr Arg Phe Val Thr Pro Gly Glu Arg Pro Ser Gly Met Phe Asp Ser
1               5                   10                  15

Ser Val Leu Cys Glu Cys Tyr Asp Ala Gly Cys Ala Trp Tyr Glu Leu
                20                  25                  30

Thr Pro Ala Glu Thr Thr Val Arg Leu Arg Ala Tyr Leu Asn Thr Pro
            35                  40                  45

Gly Leu Pro Val Cys Gln Asp His Leu Glu Phe Trp Glu Gly Val Phe
    50                  55                  60

Thr Gly Leu Thr His Ile Asp Ala His Phe Leu Ser Gln Thr Lys Gln
65                  70                  75                  80

Ala Gly Asp Asn Phe Pro Tyr Leu Val Ala Tyr Gln Ala Thr Val Cys
                    85                  90                  95

Ala Arg Ala Gln Ala Pro Pro Ser Trp Asp Gln Met Trp Lys Cys
                100                 105                 110

Leu Ile Arg Leu Lys Pro
            115

<210> SEQ ID NO 20
<211> LENGTH: 48
<212> TYPE: PRT
<213> ORGANISM: Homo sapiens

<400> SEQUENCE: 20

Lys Tyr Ile Met Thr Cys Met Ser Ala Asp Leu Glu Val Val Thr Ser
1               5                   10                  15

Thr Trp Val Leu Val Gly Gly Val Leu Ala Ala Leu Ala Ala Tyr Cys
                20                  25                  30

Leu Ser Thr Gly Cys Val Val Val Gly Arg Ile Val Leu Ser Gly
            35                  40                  45

<210> SEQ ID NO 21
<211> LENGTH: 45
<212> TYPE: PRT
<213> ORGANISM: Homo sapiens

<400> SEQUENCE: 21

Phe Trp Ala Lys His Met Trp Asn Phe Ile Ser Gly Ile Gln Tyr Leu
1               5                   10                  15

Ala Gly Leu Ser Thr Leu Pro Gly Asn Pro Ala Ile Ala Ser Leu Met
                20                  25                  30

Ala Phe Thr Ala Ala Val Thr Ser Pro Leu Thr Thr Gln
            35                  40                  45

<210> SEQ ID NO 22
```

<211> LENGTH: 45
<212> TYPE: PRT
<213> ORGANISM: Homo sapiens

<400> SEQUENCE: 22

Phe Trp Ala Lys His Met Trp Asn Phe Ile Ser Gly Ile Gln Tyr Leu
1               5                   10                  15

Ala Gly Leu Ser Thr Leu Pro Gly Asn Pro Ala Ile Ala Ser Leu Met
            20                  25                  30

Ala Phe Thr Ala Ser Val Thr Ser Pro Leu Thr Thr Gln
        35                  40                  45

<210> SEQ ID NO 23
<211> LENGTH: 110
<212> TYPE: PRT
<213> ORGANISM: Homo sapiens

<400> SEQUENCE: 23

Gly Ser Ile Gly Leu Gly Lys Val Leu Val Asp Ile Leu Ala Gly Tyr
1               5                   10                  15

Gly Ala Gly Val Ala Gly Ala Leu Val Ala Phe Lys Ile Met Ser Gly
            20                  25                  30

Glu Val Pro Ser Thr Glu Asp Leu Val Asn Leu Leu Pro Ala Ile Leu
        35                  40                  45

Ser Pro Gly Ala Leu Val Val Gly Val Val Cys Ala Ala Ile Leu Arg
    50                  55                  60

Arg His Val Gly Pro Gly Glu Gly Ala Val Gln Trp Met Asn Arg Leu
65                  70                  75                  80

Ile Ala Phe Ala Ser Arg Gly Asn His Val Ser Pro Thr His Tyr Val
                85                  90                  95

Pro Glu Ser Asp Ala Ala Ala Arg Val Thr Gln Ile Leu Ser
            100                 105                 110

<210> SEQ ID NO 24
<211> LENGTH: 22
<212> TYPE: PRT
<213> ORGANISM: Homo sapiens

<400> SEQUENCE: 24

Ser Trp Leu Arg Asp Ile Trp Asp Trp Ile Cys Glu Val Leu Ser Asp
1               5                   10                  15

Phe Lys Thr Trp Leu Lys
            20

<210> SEQ ID NO 25
<211> LENGTH: 21
<212> TYPE: PRT
<213> ORGANISM: Homo sapiens

<400> SEQUENCE: 25

Cys Pro Cys Gln Val Pro Ser Pro Glu Phe Phe Thr Glu Leu Asp Gly
1               5                   10                  15

Val Arg Leu His Arg
            20

<210> SEQ ID NO 26
<211> LENGTH: 32
<212> TYPE: PRT
<213> ORGANISM: Homo sapiens

<400> SEQUENCE: 26

Arg Arg Leu Ala Arg Gly Ser Pro Pro Ser Leu Ala Ser Ser Ser Ala
1               5                   10                  15

Ser Gln Leu Ser Ala Pro Ser Leu Lys Ala Thr Cys Thr Thr Asn His
            20                  25                  30

<210> SEQ ID NO 27
<211> LENGTH: 33
<212> TYPE: PRT
<213> ORGANISM: Homo sapiens

<400> SEQUENCE: 27

Ser Asp Ala Glu Ser Tyr Ser Ser Met Pro Pro Leu Glu Gly Glu Pro
1               5                   10                  15

Gly Asp Pro Asp Leu Ser Asp Gly Ser Trp Ser Thr Val Ser Ser Glu
            20                  25                  30

Glu

<210> SEQ ID NO 28
<211> LENGTH: 33
<212> TYPE: PRT
<213> ORGANISM: Homo sapiens

<400> SEQUENCE: 28

Ser Asp Ala Glu Ser Tyr Ser Ser Met Pro Pro Leu Glu Gly Glu Pro
1               5                   10                  15

Gly Asp Pro Asp Leu Ser Asp Gly Ser Trp Ser Thr Val Ser Ser Glu
            20                  25                  30

Ala

<210> SEQ ID NO 29
<211> LENGTH: 20
<212> TYPE: PRT
<213> ORGANISM: Homo sapiens

<400> SEQUENCE: 29

Leu Ser Asn Ser Leu Leu Arg His His Asn Met Val Tyr Ala Thr Thr
1               5                   10                  15

Ser Arg Ser Ala
            20

<210> SEQ ID NO 30
<211> LENGTH: 21
<212> TYPE: PRT
<213> ORGANISM: Homo sapiens

<400> SEQUENCE: 30

Leu Thr Pro Pro His Ser Ala Lys Ser Lys Phe Gly Tyr Gly Ala Lys
1               5                   10                  15

Asp Val Arg Cys His
            20

<210> SEQ ID NO 31
<211> LENGTH: 25
<212> TYPE: PRT
<213> ORGANISM: Homo sapiens

<400> SEQUENCE: 31

Lys Pro Ala Arg Leu Ile Val Phe Pro Asp Leu Gly Val Arg Val Cys
1               5                   10                  15

Glu Lys Met Ala Leu Tyr Asp Val Val

-continued

<210> SEQ ID NO 32
<211> LENGTH: 23
<212> TYPE: PRT
<213> ORGANISM: Homo sapiens

<400> SEQUENCE: 32

Pro Met Gly Phe Ser Tyr Asp Thr Arg Cys Phe Asp Ser Thr Val Thr
1               5                   10                  15

Glu Ser Asp Ile Arg Thr Glu
            20

<210> SEQ ID NO 33
<211> LENGTH: 54
<212> TYPE: PRT
<213> ORGANISM: Homo sapiens

<400> SEQUENCE: 33

Ser Leu Thr Glu Arg Leu Tyr Val Gly Gly Pro Leu Thr Asn Ser Lys
1               5                   10                  15

Gly Gln Asn Cys Gly Tyr Arg Arg Cys Arg Ala Ser Gly Val Leu Thr
            20                  25                  30

Thr Ser Cys Gly Asn Thr Leu Thr Cys Tyr Leu Lys Ala Ser Ala Ala
        35                  40                  45

Cys Arg Ala Ala Lys Leu
        50

<210> SEQ ID NO 34
<211> LENGTH: 23
<212> TYPE: PRT
<213> ORGANISM: Homo sapiens

<400> SEQUENCE: 34

Cys Thr Met Leu Val Cys Gly Asp Asp Leu Val Val Ile Cys Glu Ser
1               5                   10                  15

Ala Gly Thr Gln Glu Asp Ala
            20

<210> SEQ ID NO 35
<211> LENGTH: 91
<212> TYPE: PRT
<213> ORGANISM: Homo sapiens

<400> SEQUENCE: 35

Ser Leu Arg Ala Phe Thr Glu Ala Met Thr Arg Tyr Ser Ala Pro Pro
1               5                   10                  15

Gly Asp Pro Pro Gln Pro Glu Tyr Asp Leu Glu Leu Ile Thr Ser Cys
            20                  25                  30

Ser Ser Asn Val Ser Val Ala His Asp Ala Ser Gly Lys Arg Val Tyr
        35                  40                  45

Tyr Leu Thr Arg Asp Pro Thr Thr Pro Leu Ala Arg Ala Ala Trp Glu
    50                  55                  60

Thr Ala Arg His Thr Pro Val Asn Ser Trp Leu Gly Asn Ile Ile Met
65                  70                  75                  80

Phe Ala Pro Thr Leu Trp Ala Arg Met Ile Leu
                85                  90

<210> SEQ ID NO 36
<211> LENGTH: 91

```
<212> TYPE: PRT
<213> ORGANISM: Homo sapiens

<400> SEQUENCE: 36

Ser Leu Arg Ala Phe Thr Glu Ala Met Thr Arg Tyr Ser Ala Pro Pro
1               5                   10                  15

Gly Asp Pro Pro Gln Pro Glu Tyr Asp Leu Glu Leu Ile Thr Ser Cys
            20                  25                  30

Ser Ser Asn Val Ser Val Ala His Asp Ala Ser Gly Lys Arg Val Tyr
        35                  40                  45

Tyr Leu Thr Arg Asp Pro Thr Thr Pro Leu Ala Arg Ala Ala Trp Glu
    50                  55                  60

Thr Ala Arg His Thr Pro Val Asn Ser Trp Leu Gly Asn Ile Ile Met
65                  70                  75                  80

Tyr Ala Pro Thr Leu Trp Ala Arg Met Ile Leu
                85                  90

<210> SEQ ID NO 37
<211> LENGTH: 55
<212> TYPE: PRT
<213> ORGANISM: Homo sapiens

<400> SEQUENCE: 37

Glu Pro Leu Asp Leu Pro Gln Ile Ile Gln Arg Leu His Gly Leu Ser
1               5                   10                  15

Ala Phe Ser Leu His Ser Tyr Ser Pro Gly Glu Ile Asn Arg Val Ala
            20                  25                  30

Ala Cys Leu Arg Lys Leu Gly Val Pro Pro Leu Arg Ala Trp Arg His
        35                  40                  45

Arg Ala Arg Ser Val Arg Ala
    50                  55

<210> SEQ ID NO 38
<211> LENGTH: 28
<212> TYPE: PRT
<213> ORGANISM: Homo sapiens

<400> SEQUENCE: 38

Gly Gly Arg Ala Ala Ile Cys Gly Lys Tyr Leu Phe Asn Trp Ala Val
1               5                   10                  15

Arg Thr Lys Leu Lys Leu Thr Pro Ile Pro Ala Ala
            20                  25

<210> SEQ ID NO 39
<211> LENGTH: 190
<212> TYPE: PRT
<213> ORGANISM: Homo sapiens

<400> SEQUENCE: 39

Met Ser Thr Leu Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Gly Arg Arg Gln Pro
    50                  55                  60

Ile Pro Lys Ala Arg Arg Pro Glu Gly Arg Ser Trp Ala Gln Pro Gly
65                  70                  75                  80
```

```
Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Val Ala Arg Ala Leu Ala His Gly Val Arg Ala Leu Glu Asp
145                 150                 155                 160

Gly Val Asn Phe Ala Thr Gly Asn Leu Pro Gly Cys Ser Phe Ser Ile
                165                 170                 175

Phe Leu Leu Ala Leu Leu Ser Cys Leu Thr His Pro Ala Ser
            180                 185                 190

<210> SEQ ID NO 40
<211> LENGTH: 190
<212> TYPE: PRT
<213> ORGANISM: Homo sapiens

<400> SEQUENCE: 40

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser
            180                 185                 190

<210> SEQ ID NO 41
<211> LENGTH: 21
<212> TYPE: PRT
<213> ORGANISM: Homo sapiens

<400> SEQUENCE: 41

Val Asp Leu Leu Val Gly Ala Ala Thr Met Cys Ser Ala Leu Tyr Val
1               5                   10                  15

Gly Asp Leu Cys Gly
            20
```

<210> SEQ ID NO 42
<211> LENGTH: 21
<212> TYPE: PRT
<213> ORGANISM: Homo sapiens

<400> SEQUENCE: 42

Val Asp Leu Leu Val Gly Ala Ala Thr Met Cys Ser Ala Leu Tyr Val
1               5                   10                  15

Gly Asp Leu Cys Gly
            20

<210> SEQ ID NO 43
<211> LENGTH: 20
<212> TYPE: PRT
<213> ORGANISM: Homo sapiens

<400> SEQUENCE: 43

His Trp Gly Val Leu Ala Gly Leu Ala Tyr Tyr Ser Met Gln Gly Asn
1               5                   10                  15

Trp Ala Lys Val
            20

<210> SEQ ID NO 44
<211> LENGTH: 21
<212> TYPE: PRT
<213> ORGANISM: Homo sapiens

<400> SEQUENCE: 44

Ser Val Cys Gly Pro Val Tyr Cys Phe Thr Pro Ser Pro Val Val Val
1               5                   10                  15

Gly Thr Thr Asp Arg
            20

<210> SEQ ID NO 45
<211> LENGTH: 26
<212> TYPE: PRT
<213> ORGANISM: Homo sapiens

<400> SEQUENCE: 45

Arg Cys Gly Ser Gly Pro Trp Leu Thr Pro Arg Cys Leu Val Asp Tyr
1               5                   10                  15

Pro Tyr Arg Leu Trp His Tyr Pro Cys Thr
            20                  25

<210> SEQ ID NO 46
<211> LENGTH: 21
<212> TYPE: PRT
<213> ORGANISM: Homo sapiens

<400> SEQUENCE: 46

Ala Ala Cys Asn Trp Thr Arg Gly Glu Arg Cys Asp Ile Glu Asp Arg
1               5                   10                  15

Asp Arg Ser Glu Leu
            20

<210> SEQ ID NO 47
<211> LENGTH: 41
<212> TYPE: PRT
<213> ORGANISM: Homo sapiens

<400> SEQUENCE: 47

```
Thr Thr Glu Leu Ala Ile Leu Pro Cys Ser Phe Thr Pro Leu Pro Ala
1               5                   10                  15

Leu Ser Thr Gly Leu Ile His Leu His Gln Asn Ile Val Asp Val Gln
            20                  25                  30

Tyr Leu Tyr Gly Val Gly Ser Gly Met
        35                  40
```

<210> SEQ ID NO 48
<211> LENGTH: 45
<212> TYPE: PRT
<213> ORGANISM: Homo sapiens

<400> SEQUENCE: 48

```
Met Gly Trp Arg Leu Leu Ala Pro Ile Thr Ala Tyr Ala Gln Gln Thr
1               5                   10                  15

Arg Gly Leu Leu Gly Cys Ile Val Thr Ser Leu Thr Gly Arg Asp Lys
            20                  25                  30

Asn Val Val Glu Gly Glu Val Gln Val Leu Ser Thr Ala
        35                  40                  45
```

<210> SEQ ID NO 49
<211> LENGTH: 45
<212> TYPE: PRT
<213> ORGANISM: Homo sapiens

<400> SEQUENCE: 49

```
Met Gly Trp Arg Leu Leu Ala Pro Ile Thr Ala Tyr Ala Gln Gln Thr
1               5                   10                  15

Arg Gly Leu Leu Gly Thr Ile Val Thr Ser Leu Thr Gly Arg Asp Lys
            20                  25                  30

Asn Val Val Thr Gly Glu Val Gln Val Leu Ser Thr Ala
        35                  40                  45
```

<210> SEQ ID NO 50
<211> LENGTH: 80
<212> TYPE: PRT
<213> ORGANISM: Homo sapiens

<400> SEQUENCE: 50

```
Pro Cys Thr Cys Gly Ser Ser Asp Leu Tyr Leu Val Thr Arg His Ala
1               5                   10                  15

Asp Val Ile Pro Ala Arg Arg Gly Asp Ser Arg Ala Ser Leu Leu
            20                  25                  30

Ser Pro Arg Pro Leu Ala Tyr Leu Lys Gly Ser Ser Gly Gly Pro Leu
            35                  40                  45

Leu Cys Pro Ser Gly His Val Ala Gly Ile Phe Arg Ala Ala Val Cys
    50                  55                  60

Thr Arg Gly Val Ala Lys Ala Leu Gln Phe Ile Pro Val Glu Thr Leu
65                  70                  75                  80
```

<210> SEQ ID NO 51
<211> LENGTH: 80
<212> TYPE: PRT
<213> ORGANISM: Homo sapiens

<400> SEQUENCE: 51

```
Pro Cys Thr Cys Gly Ser Ala Asp Leu Tyr Leu Val Thr Arg Asp Ala
1               5                   10                  15

Asp Val Ile Pro Ala Arg Arg Gly Asp Ser Thr Ala Ser Leu Leu
            20                  25                  30
```

Ser Pro Arg Pro Leu Ala Cys Leu Lys Gly Ser Ser Gly Gly Pro Val
        35                  40                  45

Met Cys Pro Ser Gly His Val Ala Gly Ile Phe Arg Ala Ala Val Cys
 50                  55                  60

Thr Arg Gly Val Ala Lys Ala Leu Gln Phe Ile Pro Val Glu Thr Leu
 65                  70                  75                  80

<210> SEQ ID NO 52
<211> LENGTH: 66
<212> TYPE: PRT
<213> ORGANISM: Homo sapiens

<400> SEQUENCE: 52

Arg Ser Pro Ser Phe Ser Asp Asn Ser Thr Pro Pro Ala Val Pro Gln
 1               5                  10                  15

Ser Tyr Gln Val Ala His Leu His Ala Pro Thr Gly Ser Gly Lys Ser
                20                  25                  30

Thr Lys Val Pro Ala Ala Tyr Ala Ala Gln Gly Tyr Lys Val Leu Val
        35                  40                  45

Leu Asn Pro Ser Val Ala Ala Thr Leu Gly Phe Gly Ala Tyr Met Ser
 50                  55                  60

Lys Ala
 65

<210> SEQ ID NO 53
<211> LENGTH: 66
<212> TYPE: PRT
<213> ORGANISM: Homo sapiens

<400> SEQUENCE: 53

Arg Ser Pro Val Phe Ser Asp Asn Ser Ser Pro Ala Val Pro Gln
 1               5                  10                  15

Ser Tyr Gln Val Ala His Leu His Ala Pro Thr Gly Ser Gly Lys Ser
                20                  25                  30

Thr Lys Val Pro Ala Ala Tyr Ala Ala Gln Gly Tyr Lys Val Leu Val
        35                  40                  45

Leu Asn Pro Ser Val Ala Ala Thr Leu Gly Phe Gly Ala Tyr Met Ser
 50                  55                  60

Lys Ala
 65

<210> SEQ ID NO 54
<211> LENGTH: 88
<212> TYPE: PRT
<213> ORGANISM: Homo sapiens

<400> SEQUENCE: 54

Thr Gly Asn Arg Thr Ile Thr Thr Gly Ala Lys Ile Thr Tyr Ser Thr
 1               5                  10                  15

Tyr Gly Lys Phe Leu Ala Asp Gly Gly Cys Ser Gly Gly Ala Tyr Asp
                20                  25                  30

Ile Ile Ile Cys Asp Glu Cys His Ser Gln Asp Ala Thr Ser Ile Leu
        35                  40                  45

Gly Ile Gly Thr Val Leu Asp Gln Ala Glu Thr Ala Gly Ala Arg Leu
 50                  55                  60

Thr Val Leu Ala Thr Ala Thr Pro Pro Gly Ser Ile Thr Val Pro His
 65                  70                  75                  80

```
Ser Asn Ile Glu Glu Val Ala Leu
            85
```

<210> SEQ ID NO 55
<211> LENGTH: 88
<212> TYPE: PRT
<213> ORGANISM: Homo sapiens

<400> SEQUENCE: 55

```
Thr Gly Asn Arg Thr Ile Thr Thr Gly Ala Lys Leu Thr Tyr Ser Thr
1               5                   10                  15

Tyr Gly Lys Phe Leu Ala Asp Gly Gly Cys Ser Gly Gly Ala Tyr Asp
                20                  25                  30

Val Ile Ile Cys Asp Glu Cys His Ala Gln Asp Ala Thr Ser Ile Leu
            35                  40                  45

Gly Ile Gly Thr Val Leu Asp Gln Ala Glu Thr Ala Gly Val Arg Leu
    50                  55                  60

Thr Val Leu Ala Thr Ala Thr Pro Pro Gly Ser Ile Thr Val Pro His
65                  70                  75                  80

Ser Asn Ile Glu Glu Val Ala Leu
            85
```

<210> SEQ ID NO 56
<211> LENGTH: 210
<212> TYPE: PRT
<213> ORGANISM: Homo sapiens

<400> SEQUENCE: 56

```
Ser Val Ile Pro Thr Ser Gly Asp Val Val Cys Ala Thr Asp Ala
1               5                   10                  15

Leu Met Thr Gly Phe Thr Gly Asp Phe Asp Ser Val Ile Asp Cys Asn
                20                  25                  30

Thr Cys Val Glu Gln Thr Val Asp Phe Ser Leu Asp Pro Thr Phe Ser
            35                  40                  45

Ile Glu Thr Thr Thr Ala Pro Gln Asp Ala Val Ser Arg Ser Gln Arg
    50                  55                  60

Arg Gly Arg Thr Gly Arg Gly Arg Leu Gly Thr Tyr Arg Phe Val Thr
65                  70                  75                  80

Pro Gly Glu Arg Pro Ser Gly Met Phe Asp Ser Val Val Leu Cys Glu
                85                  90                  95

Cys Tyr Asp Ala Gly Cys Ala Trp Tyr Glu Leu Gln Pro Ala Glu Thr
            100                 105                 110

Thr Val Arg Leu Arg Ala Tyr Leu Asn Thr Pro Gly Leu Pro Val Cys
    115                 120                 125

Gln Asp His Leu Glu Phe Trp Glu Ser Val Phe Thr Gly Leu Thr His
130                 135                 140

Ile Asp Ala His Phe Leu Ser Gln Thr Lys Gln Gln Gly Leu Asn Phe
145                 150                 155                 160

Pro Tyr Leu Val Ala Tyr Gln Ala Thr Val Cys Ala Arg Ala Gln Ala
                165                 170                 175

Pro Pro Pro Ser Trp Asp Glu Met Trp Lys Cys Leu Val Arg Leu Lys
            180                 185                 190

Pro Thr Leu His Gly Pro Thr Pro Leu Leu Tyr Arg Leu Gly Ala Val
    195                 200                 205

Gln Asn
    210
```

<210> SEQ ID NO 57
<211> LENGTH: 210
<212> TYPE: PRT
<213> ORGANISM: Homo sapiens

<400> SEQUENCE: 57

Ser Val Ile Pro Thr Ala Gly Asp Val Val Cys Ala Thr Asp Ala
1               5                   10                  15

Leu Met Thr Gly Phe Thr Gly Asp Phe Asp Ser Val Ile Asp Cys Asn
            20                  25                  30

Val Ala Val Glu Gln Tyr Val Asp Phe Ser Leu Asp Pro Thr Phe Ser
        35                  40                  45

Ile Glu Thr Arg Thr Ala Pro Gln Asp Ala Val Ser Arg Ser Gln Arg
50                  55                  60

Arg Gly Arg Thr Gly Arg Gly Arg Leu Gly Thr Tyr Arg Tyr Val Gly
65                  70                  75                  80

Pro Gly Glu Arg Pro Ser Gly Met Phe Asp Ser Val Val Leu Cys Glu
                85                  90                  95

Cys Tyr Asp Ala Gly Cys Ala Trp Tyr Glu Leu Gln Pro Ala Glu Thr
            100                 105                 110

Thr Val Arg Leu Arg Ala Tyr Leu Ser Thr Pro Gly Leu Pro Val Cys
        115                 120                 125

Gln Asp His Leu Asp Phe Trp Glu Ser Val Phe Thr Gly Leu Thr His
    130                 135                 140

Ile Asp Ala His Phe Leu Ser Gln Thr Lys Gln Gln Gly Leu Asn Phe
145                 150                 155                 160

Pro Tyr Leu Thr Ala Tyr Gln Ala Thr Val Cys Ala Arg Ala Gln Ala
                165                 170                 175

Pro Pro Pro Ser Trp Asp Glu Met Trp Lys Cys Leu Val Arg Leu Lys
            180                 185                 190

Pro Thr Leu His Gly Pro Thr Pro Leu Leu Tyr Arg Leu Gly Pro Val
        195                 200                 205

Gln Asn
    210

<210> SEQ ID NO 58
<211> LENGTH: 40
<212> TYPE: PRT
<213> ORGANISM: Homo sapiens

<400> SEQUENCE: 58

Met Ala Cys Met Ser Ala Asp Leu Glu Val Thr Thr Ser Thr Trp Val
1               5                   10                  15

Leu Leu Gly Gly Val Leu Ala Ala Leu Ala Ala Tyr Cys Leu Ser Thr
            20                  25                  30

Gly Cys Val Val Ile Val Gly His
        35                  40

<210> SEQ ID NO 59
<211> LENGTH: 40
<212> TYPE: PRT
<213> ORGANISM: Homo sapiens

<400> SEQUENCE: 59

Met Ala Cys Met Ser Ala Asp Leu Glu Val Thr Thr Ser Thr Trp Val
1               5                   10                  15

Leu Leu Gly Gly Val Leu Ala Ala Leu Ala Ala Tyr Cys Leu Ser Val

```
                20                  25                  30

Gly Cys Val Val Ile Val Gly His
         35                  40

<210> SEQ ID NO 60
<211> LENGTH: 36
<212> TYPE: PRT
<213> ORGANISM: Homo sapiens

<400> SEQUENCE: 60

Phe Trp Ala Lys His Met Trp Asn Phe Ile Ser Gly Ile Gln Tyr Leu
1               5                   10                  15

Ala Gly Leu Ser Thr Leu Pro Gly Asn Pro Ala Ile Ala Ser Leu Met
            20                  25                  30

Ala Phe Thr Ala
        35

<210> SEQ ID NO 61
<211> LENGTH: 114
<212> TYPE: PRT
<213> ORGANISM: Homo sapiens

<400> SEQUENCE: 61

Ile Gly Ser Ile Gly Leu Gly Lys Val Leu Val Asp Ile Leu Ala Gly
1               5                   10                  15

Tyr Gly Ala Gly Val Ala Gly Ala Leu Val Ala Phe Lys Ile Met Gly
            20                  25                  30

Gly Glu Leu Pro Ser Thr Glu Asp Met Val Asn Leu Leu Pro Ala Ile
        35                  40                  45

Leu Ser Pro Gly Ala Leu Val Val Gly Val Val Cys Ala Ala Ile Leu
    50                  55                  60

Arg Arg His Val Gly Pro Gly Glu Gly Ala Val Gln Trp Met Asn Arg
65                  70                  75                  80

Leu Ile Ala Phe Ala Ser Arg Gly Asn His Val Ser Pro Thr His Tyr
                85                  90                  95

Val Pro Glu Ser Asp Ala Ala Arg Val Thr Ala Ile Leu Ser Ser
            100                 105                 110

Leu Thr

<210> SEQ ID NO 62
<211> LENGTH: 114
<212> TYPE: PRT
<213> ORGANISM: Homo sapiens

<400> SEQUENCE: 62

Ile Gly Ser Val Gly Leu Gly Lys Val Leu Val Asp Ile Leu Ala Gly
1               5                   10                  15

Tyr Gly Ala Gly Val Ala Gly Ala Leu Val Ala Phe Lys Ile Met Ser
            20                  25                  30

Gly Glu Ile Pro Ser Thr Glu Asp Leu Val Asn Leu Leu Pro Ala Ile
        35                  40                  45

Leu Ser Pro Gly Ala Leu Val Val Gly Val Val Cys Ala Ala Ile Leu
    50                  55                  60

Arg Arg His Val Gly Pro Gly Glu Gly Ala Val Gln Trp Met Asn Arg
65                  70                  75                  80

Leu Ile Ala Phe Ala Ser Arg Gly Asn His Val Ser Pro Thr His Tyr
                85                  90                  95
```

Val Pro Glu Ser Asp Ala Ala Ala Arg Val Thr Ala Ile Leu Ser Ser
            100                 105                 110

Leu Thr

<210> SEQ ID NO 63
<211> LENGTH: 21
<212> TYPE: PRT
<213> ORGANISM: Homo sapiens

<400> SEQUENCE: 63

Cys Pro Cys Gln Val Pro Ala Pro Glu Phe Phe Thr Glu Val Asp Gly
1               5                   10                  15

Val Arg Leu His Arg
            20

<210> SEQ ID NO 64
<211> LENGTH: 20
<212> TYPE: PRT
<213> ORGANISM: Homo sapiens

<400> SEQUENCE: 64

Ile Gly Ser Gln Leu Pro Cys Glu Pro Glu Pro Asp Val Ser Val Leu
1               5                   10                  15

Thr Ser Met Leu
            20

<210> SEQ ID NO 65
<211> LENGTH: 35
<212> TYPE: PRT
<213> ORGANISM: Homo sapiens

<400> SEQUENCE: 65

Thr Ala Ala Arg Arg Leu Ala Arg Gly Ser Pro Pro Ser Glu Ala Ser
1               5                   10                  15

Ser Ser Ala Ser Gln Leu Ser Ala Pro Ser Leu Lys Ala Thr Cys Gln
            20                  25                  30

Thr His His
        35

<210> SEQ ID NO 66
<211> LENGTH: 35
<212> TYPE: PRT
<213> ORGANISM: Homo sapiens

<400> SEQUENCE: 66

Thr Ala Ala Arg Arg Leu Ala Arg Gly Ser Pro Pro Ser Glu Ala Ser
1               5                   10                  15

Ser Ser Ala Ser Gln Leu Ser Ala Pro Ser Leu Lys Ala Thr Cys Gln
            20                  25                  30

Thr His Arg
        35

<210> SEQ ID NO 67
<211> LENGTH: 32
<212> TYPE: PRT
<213> ORGANISM: Homo sapiens

<400> SEQUENCE: 67

Glu Ser Asp Ser Glu Ser Cys Ser Ser Met Pro Pro Leu Glu Gly Glu
1               5                   10                  15

Pro Gly Asp Pro Asp Leu Ser Asp Gly Ser Trp Ser Thr Val Ser Asp 20                  25                  30

<210> SEQ ID NO 68
<211> LENGTH: 32
<212> TYPE: PRT
<213> ORGANISM: Homo sapiens

<400> SEQUENCE: 68

Glu Ser Asp Ser Glu Ser Cys Ser Ser Met Pro Pro Leu Glu Gly Glu
1               5                   10                  15

Pro Gly Asp Pro Asp Leu Ser Cys Asp Ser Trp Ser Thr Val Ser Asp
                20                  25                  30

<210> SEQ ID NO 69
<211> LENGTH: 71
<212> TYPE: PRT
<213> ORGANISM: Homo sapiens

<400> SEQUENCE: 69

Gln Asp Val Val Cys Cys Ser Met Ser Tyr Ser Trp Thr Gly Ala Leu
1               5                   10                  15

Ile Thr Pro Cys Ala Ala Glu Glu Lys Leu Pro Ile Asn Pro Leu
                20                  25                  30

Ser Asn Ser Leu Leu Arg His His Asn Leu Val Tyr Ser Thr Ser Ser
        35                  40                  45

Arg Ser Ala Ser Gln Arg Gln Lys Lys Val Thr Phe Asp Arg Leu Gln
    50                  55                  60

Val Leu Asp Asp His Tyr Lys
65                  70

<210> SEQ ID NO 70
<211> LENGTH: 71
<212> TYPE: PRT
<213> ORGANISM: Homo sapiens

<400> SEQUENCE: 70

Gln Ser Val Val Cys Cys Ser Met Ser Tyr Ser Trp Thr Gly Ala Leu
1               5                   10                  15

Ile Thr Pro Cys Ser Ala Glu Glu Lys Leu Pro Ile Asn Pro Leu
                20                  25                  30

Ser Asn Ser Leu Leu Arg His His Asn Leu Val Tyr Ser Thr Ser Ser
        35                  40                  45

Arg Ser Ala Ser Gln Arg Gln Lys Lys Val Thr Phe Asp Arg Leu Gln
    50                  55                  60

Val Leu Asp Asp His Tyr Lys
65                  70

<210> SEQ ID NO 71
<211> LENGTH: 30
<212> TYPE: PRT
<213> ORGANISM: Homo sapiens

<400> SEQUENCE: 71

Pro Glu Lys Gly Gly Arg Lys Pro Ala Arg Leu Ile Val Tyr Pro Asp
1               5                   10                  15

Leu Gly Val Arg Val Cys Glu Lys Met Ala Leu Tyr Asp Val
                20                  25                  30

<210> SEQ ID NO 72
<211> LENGTH: 31

<212> TYPE: PRT
<213> ORGANISM: Homo sapiens

<400> SEQUENCE: 72

Trp Thr Ser Lys Lys Thr Pro Met Gly Phe Ser Tyr Asp Thr Arg Cys
1               5                   10                  15

Phe Asp Ser Thr Val Thr Glu Gln Asp Ile Arg Val Glu Glu
            20                  25                  30

<210> SEQ ID NO 73
<211> LENGTH: 30
<212> TYPE: PRT
<213> ORGANISM: Homo sapiens

<400> SEQUENCE: 73

Cys Gly Tyr Arg Arg Cys Arg Ala Ser Gly Val Leu Pro Thr Ser Cys
1               5                   10                  15

Gly Asn Thr Leu Thr Cys Tyr Ile Lys Ala Thr Ala Ala Cys
            20                  25                  30

<210> SEQ ID NO 74
<211> LENGTH: 30
<212> TYPE: PRT
<213> ORGANISM: Homo sapiens

<400> SEQUENCE: 74

Cys Gly Tyr Arg Arg Cys Arg Ala Ser Gly Val Leu Thr Thr Ser Cys
1               5                   10                  15

Gly Asn Thr Leu Thr Cys Tyr Ile Lys Ala Arg Ala Ala Cys
            20                  25                  30

<210> SEQ ID NO 75
<211> LENGTH: 22
<212> TYPE: PRT
<213> ORGANISM: Homo sapiens

<400> SEQUENCE: 75

Ala Leu Arg Ala Phe Thr Glu Ala Met Thr Arg Tyr Ser Ala Pro Pro
1               5                   10                  15

Gly Asp Ala Pro Gln Pro
            20

<210> SEQ ID NO 76
<211> LENGTH: 49
<212> TYPE: PRT
<213> ORGANISM: Homo sapiens

<400> SEQUENCE: 76

Lys Gly Lys Arg Val Tyr Tyr Leu Thr Arg Asp Pro Thr Thr Pro Leu
1               5                   10                  15

Ala Arg Ala Ala Trp Glu Thr Ala Arg His Thr Pro Val Asn Ser Trp
            20                  25                  30

Leu Gly Asn Ile Ile Met Tyr Ala Pro Thr Ile Trp Val Arg Met Val
        35                  40                  45

Leu

<210> SEQ ID NO 77
<211> LENGTH: 49
<212> TYPE: PRT
<213> ORGANISM: Homo sapiens

<400> SEQUENCE: 77

```
Lys Gly Lys Arg Tyr Tyr Leu Thr Arg Asp Pro Thr Thr Pro Leu
1               5                   10                  15

Ala Arg Ala Ala Trp Glu Thr Ala Arg His Thr Pro Val Asn Ser Trp
            20                  25                  30

Leu Gly Asn Ile Ile Met Tyr Ala Pro Thr Ile Trp Val Arg Met Val
            35                  40                  45

Met
```

<210> SEQ ID NO 78
<211> LENGTH: 56
<212> TYPE: PRT
<213> ORGANISM: Homo sapiens

<400> SEQUENCE: 78

```
Tyr Gly Ala Thr Tyr Ser Val Glu Pro Leu Asp Leu Pro Ala Ile Ile
1               5                   10                  15

Glu Arg Leu His Gly Leu Ser Ala Phe Ser Leu His Ser Tyr Ser Pro
            20                  25                  30

Gly Glu Ile Asn Arg Val Ala Gly Cys Leu Arg Lys Leu Gly Cys Pro
            35                  40                  45

Pro Leu Arg Ala Trp Arg His Arg
        50                  55
```

<210> SEQ ID NO 79
<211> LENGTH: 56
<212> TYPE: PRT
<213> ORGANISM: Homo sapiens

<400> SEQUENCE: 79

```
Tyr Gly Ala Thr Tyr Ser Val Thr Pro Leu Asp Leu Pro Ala Ile Ile
1               5                   10                  15

Glu Arg Leu His Gly Leu Ser Ala Phe Thr Leu His Ser Tyr Ser Pro
            20                  25                  30

Val Glu Leu Asn Arg Val Ala Gly Thr Leu Arg Lys Leu Gly Cys Pro
            35                  40                  45

Pro Leu Arg Ala Trp Arg His Arg
        50                  55
```

<210> SEQ ID NO 80
<211> LENGTH: 27
<212> TYPE: PRT
<213> ORGANISM: Homo sapiens

<400> SEQUENCE: 80

```
Val Arg Ala Lys Leu Leu Ser Gln Gly Gly Arg Ala Ala Ile Cys Gly
1               5                   10                  15

Lys Tyr Leu Phe Asn Trp Ala Val Arg Thr Lys
            20                  25
```

<210> SEQ ID NO 81
<211> LENGTH: 180
<212> TYPE: PRT
<213> ORGANISM: Homo sapiens

<400> SEQUENCE: 81

```
Thr Lys Arg Asn Thr Asn Arg Arg Pro Gln Asp Val Lys Phe Pro Gly
1               5                   10                  15

Gly Gly Gln Ile Val Gly Gly Val Tyr Leu Leu Pro Arg Arg Gly Pro
            20                  25                  30
```

```
Arg Leu Gly Val Arg Ala Thr Arg Lys Thr Ser Glu Arg Ser Gln Pro
            35                  40                  45

Arg Gly Arg Arg Gln Pro Ile Pro Lys Ala Arg Arg Pro Glu Gly Arg
    50                  55                  60

Ser Trp Ala Gln Pro Gly Tyr Pro Trp Pro Leu Tyr Gly Asn Glu Gly
65                  70                  75                  80

Cys Gly Trp Ala Gly Trp Leu Leu Ser Pro Arg Gly Ser Arg Pro Ser
                85                  90                  95

Trp Gly Pro Asn Asp Pro Arg Arg Ser Arg Asn Leu Gly Lys Val
                100                 105                 110

Ile Asp Thr Leu Thr Cys Gly Phe Ala Asp Leu Met Gly Tyr Ile Pro
                115                 120                 125

Leu Val Gly Ala Pro Val Gly Gly Val Ala Arg Ala Leu Ala His Gly
            130                 135                 140

Val Arg Val Leu Glu Asp Gly Ile Asn Tyr Ala Thr Gly Asn Leu Pro
145                 150                 155                 160

Gly Cys Ser Phe Ser Ile Phe Leu Leu Ala Leu Leu Ser Cys Leu Thr
                165                 170                 175

Val Pro Ala Ser
            180

<210> SEQ ID NO 82
<211> LENGTH: 180
<212> TYPE: PRT
<213> ORGANISM: Homo sapiens

<400> SEQUENCE: 82

Thr Lys Arg Asn Thr Asn Arg Arg Pro Met Asp Val Lys Phe Pro Gly
1               5                   10                  15

Gly Gly Gln Ile Val Gly Gly Val Tyr Leu Leu Pro Arg Arg Gly Pro
            20                  25                  30

Arg Leu Gly Val Arg Ala Thr Arg Lys Thr Ser Glu Arg Ser Gln Pro
            35                  40                  45

Arg Gly Arg Arg Gln Pro Ile Pro Lys Ala Arg Arg Pro Glu Gly Arg
    50                  55                  60

Ser Trp Ala Gln Pro Gly Tyr Pro Trp Pro Leu Tyr Gly Asn Glu Gly
65                  70                  75                  80

Cys Gly Trp Ala Gly Trp Leu Leu Ser Pro Arg Gly Ser Arg Pro Ser
                85                  90                  95

Trp Gly Pro Asn Asp Pro Arg Arg Ser Arg Asn Leu Gly Lys Val
                100                 105                 110

Ile Asp Thr Leu Thr Cys Gly Phe Ala Asp Leu Met Gly Tyr Ile Pro
                115                 120                 125

Leu Val Gly Ala Pro Val Gly Gly Val Ala Arg Ala Leu Ala His Gly
            130                 135                 140

Val Arg Ala Leu Glu Asp Gly Ile Asn Tyr Ala Thr Gly Asn Leu Pro
145                 150                 155                 160

Gly Cys Ser Phe Ser Ile Phe Leu Leu Ala Leu Leu Ser Cys Leu Thr
                165                 170                 175

Val Pro Ala Ser
            180

<210> SEQ ID NO 83
<211> LENGTH: 27
<212> TYPE: PRT
```

<213> ORGANISM: Homo sapiens

<400> SEQUENCE: 83

Cys Asn Cys Ser Ile Tyr Pro Gly His Ile Thr Gly His Arg Met Ala
1               5                   10                  15
Trp Asp Met Met Met Asn Trp Ser Pro Thr Thr
            20                  25

<210> SEQ ID NO 84
<211> LENGTH: 22
<212> TYPE: PRT
<213> ORGANISM: Homo sapiens

<400> SEQUENCE: 84

Asn Gly Ser Trp His Ile Asn Arg Thr Ala Leu Asn Cys Asn Asp Ser
1               5                   10                  15
Leu Asn Thr Gly Phe Ile
            20

<210> SEQ ID NO 85
<211> LENGTH: 44
<212> TYPE: PRT
<213> ORGANISM: Homo sapiens

<400> SEQUENCE: 85

Cys Pro Thr Asp Cys Phe Arg Lys His Pro Glu Ala Thr Tyr Thr Lys
1               5                   10                  15
Cys Gly Ser Gly Pro Trp Leu Thr Pro Arg Cys Leu Val Asp Tyr Pro
            20                  25                  30
Tyr Arg Leu Trp His Tyr Pro Cys Thr Val Asn Phe
        35                  40

<210> SEQ ID NO 86
<211> LENGTH: 43
<212> TYPE: PRT
<213> ORGANISM: Homo sapiens

<400> SEQUENCE: 86

Leu Leu His Ser Thr Thr Glu Trp Ala Ile Leu Pro Cys Ser Phe Thr
1               5                   10                  15
Thr Leu Pro Ala Leu Ser Thr Gly Leu Ile His Leu His Gln Asn Ile
            20                  25                  30
Val Asp Val Gln Tyr Leu Tyr Gly Val Gly Ser
        35                  40

<210> SEQ ID NO 87
<211> LENGTH: 43
<212> TYPE: PRT
<213> ORGANISM: Homo sapiens

<400> SEQUENCE: 87

Leu Leu Leu Ser Thr Thr Glu Trp Gln Ile Leu Pro Cys Ser Phe Thr
1               5                   10                  15
Thr Leu Pro Ala Leu Ser Thr Gly Leu Ile His Leu His Gln Asn Ile
            20                  25                  30
Val Asp Val Gln Tyr Leu Tyr Gly Val Gly Ser
        35                  40

<210> SEQ ID NO 88
<211> LENGTH: 33
<212> TYPE: PRT

<213> ORGANISM: Homo sapiens

<400> SEQUENCE: 88

Lys Gly Trp Arg Leu Leu Ala Pro Ile Thr Ala Tyr Ala Gln Gln Thr
1               5                   10                  15

Arg Gly Leu Leu Gly Thr Ile Val Thr Ser Leu Thr Gly Arg Asp Lys
            20                  25                  30

Asn

<210> SEQ ID NO 89
<211> LENGTH: 33
<212> TYPE: PRT
<213> ORGANISM: Homo sapiens

<400> SEQUENCE: 89

Met Gly Trp Arg Leu Leu Ala Pro Ile Thr Ala Tyr Ala Gln Gln Thr
1               5                   10                  15

Arg Gly Leu Leu Gly Thr Ile Val Thr Ser Leu Thr Gly Arg Asp Lys
            20                  25                  30

Asn

<210> SEQ ID NO 90
<211> LENGTH: 81
<212> TYPE: PRT
<213> ORGANISM: Homo sapiens

<400> SEQUENCE: 90

Pro Cys Thr Cys Gly Ser Ser Asp Leu Tyr Leu Val Thr Arg His Ala
1               5                   10                  15

Asp Val Ile Pro Ala Arg Arg Gly Asp Ser Arg Ala Ser Leu Leu
            20                  25                  30

Ser Pro Arg Pro Ile Ser Thr Leu Lys Gly Ser Ser Gly Gly Pro Val
        35                  40                  45

Leu Cys Pro Ser Gly His Val Val Gly Ile Phe Arg Ala Ala Val Cys
    50                  55                  60

Thr Arg Gly Val Ala Lys Ala Leu Asp Phe Ile Pro Val Glu Ser Leu
65                  70                  75                  80

Glu

<210> SEQ ID NO 91
<211> LENGTH: 81
<212> TYPE: PRT
<213> ORGANISM: Homo sapiens

<400> SEQUENCE: 91

Pro Cys Thr Cys Gly Ser Ser Asp Leu Tyr Leu Val Thr Arg His Ala
1               5                   10                  15

Asp Val Ile Pro Val Arg Arg Arg Gly Asp Ser Arg Gly Ser Leu Leu
            20                  25                  30

Ser Pro Arg Pro Ile Ser Tyr Leu Lys Gly Ser Ser Gly Gly Pro Val
        35                  40                  45

Leu Cys Pro Ser Gly His Ala Val Gly Ile Phe Arg Ala Ala Val Cys
    50                  55                  60

Thr Arg Gly Val Ala Lys Ala Val Asp Phe Ile Pro Val Glu Ser Leu
65                  70                  75                  80

Glu

```
<210> SEQ ID NO 92
<211> LENGTH: 70
<212> TYPE: PRT
<213> ORGANISM: Homo sapiens

<400> SEQUENCE: 92

Met Arg Ser Pro Val Phe Thr Asp Asn Ser Thr Pro Pro Ala Val Pro
1               5                   10                  15

Gln Thr Tyr Gln Val Gly His Leu His Ala Pro Thr Gly Ser Gly Lys
            20                  25                  30

Ser Thr Lys Val Pro Ala Ala Tyr Ala Ala Gln Gly Tyr Lys Val Leu
        35                  40                  45

Val Leu Asn Pro Ser Val Ala Ala Thr Leu Gly Phe Gly Ala Tyr Met
    50                  55                  60

Ser Lys Ala Tyr Gly Ile
65                  70

<210> SEQ ID NO 93
<211> LENGTH: 70
<212> TYPE: PRT
<213> ORGANISM: Homo sapiens

<400> SEQUENCE: 93

Met Arg Ser Pro Val Phe Thr Asp Asn Ser Thr Pro Pro Ala Val Pro
1               5                   10                  15

Gln Thr Tyr Gln Val Ala His Leu His Ala Pro Thr Gly Ser Gly Lys
            20                  25                  30

Ser Thr Lys Val Pro Ala Ala Tyr Ala Ala Gln Gly Tyr Lys Val Leu
        35                  40                  45

Val Leu Asn Pro Ser Val Ala Ala Thr Leu Gly Phe Gly Ala Tyr Met
    50                  55                  60

Ser Lys Ala Tyr Gly Ile
65                  70

<210> SEQ ID NO 94
<211> LENGTH: 75
<212> TYPE: PRT
<213> ORGANISM: Homo sapiens

<400> SEQUENCE: 94

Arg Thr Gly Val Arg Thr Val Thr Gly Ala Pro Ile Thr Tyr Ser
1               5                   10                  15

Thr Tyr Gly Lys Phe Leu Ala Asp Gly Gly Cys Ser Gly Gly Ala Tyr
            20                  25                  30

Asp Ile Ile Ile Cys Asp Glu Cys His Ser Thr Asp Ala Thr Thr Ile
        35                  40                  45

Leu Gly Ile Gly Thr Val Leu Asp Gln Ala Glu Thr Ala Gly Val Arg
    50                  55                  60

Leu Val Val Leu Ala Thr Ala Thr Pro Pro Gly
65                  70                  75

<210> SEQ ID NO 95
<211> LENGTH: 75
<212> TYPE: PRT
<213> ORGANISM: Homo sapiens

<400> SEQUENCE: 95

Arg Ser Gly Val Arg Thr Ile Thr Thr Gly Ala Pro Ile Thr Tyr Ser
1               5                   10                  15
```

```
Thr Tyr Gly Lys Phe Leu Ala Asp Gly Gly Cys Ser Gly Gly Ala Tyr
            20                  25                  30

Asp Ile Ile Cys Asp Glu Cys His Ser Thr Asp Ser Thr Thr Ile
        35                  40                  45

Leu Gly Ile Gly Thr Val Leu Asp Gln Ala Glu Thr Ala Gly Val Arg
        50                  55                  60

Leu Val Val Leu Ala Thr Ala Thr Pro Pro Gly
65                  70                  75
```

<210> SEQ ID NO 96
<211> LENGTH: 20
<212> TYPE: PRT
<213> ORGANISM: Homo sapiens

<400> SEQUENCE: 96

```
Ile Lys Gly Gly Arg His Leu Ile Phe Cys His Ser Lys Lys Lys Cys
1               5                   10                  15

Asp Glu Leu Ala
            20
```

<210> SEQ ID NO 97
<211> LENGTH: 196
<212> TYPE: PRT
<213> ORGANISM: Homo sapiens

<400> SEQUENCE: 97

```
Asn Ala Val Ala Tyr Tyr Arg Gly Leu Asp Val Ser Val Ile Pro Thr
1               5                   10                  15

Ser Gly Asp Val Val Cys Ala Thr Asp Ala Leu Met Thr Gly Phe
            20                  25                  30

Thr Gly Asp Phe Asp Ser Val Ile Asp Cys Asn Val Ala Val Thr Gln
        35                  40                  45

Thr Val Asp Phe Ser Leu Asp Pro Thr Phe Thr Ile Glu Thr Thr Thr
    50                  55                  60

Val Pro Gln Asp Ala Val Ser Arg Ser Gln Arg Arg Gly Arg Thr Gly
65                  70                  75                  80

Arg Gly Arg Leu Gly Ile Tyr Arg Tyr Val Ser Pro Gly Glu Arg Pro
                85                  90                  95

Ser Gly Met Phe Asp Ser Val Val Leu Cys Glu Cys Tyr Asp Ala Gly
            100                 105                 110

Cys Ala Trp Tyr Glu Leu Thr Pro Ala Glu Thr Thr Val Arg Leu Arg
        115                 120                 125

Ala Tyr Leu Asn Thr Pro Gly Leu Pro Val Cys Gln Asp His Leu Glu
    130                 135                 140

Phe Trp Glu Gly Val Phe Thr Gly Leu Thr His Ile Asp Ala His Phe
145                 150                 155                 160

Leu Ser Gln Thr Lys Gln Gly Gly Glu Asn Phe Pro Tyr Leu Val Ala
                165                 170                 175

Tyr Gln Ala Thr Val Cys Ala Arg Ala Lys Ala Pro Pro Pro Ser Trp
            180                 185                 190

Asp Thr Met Trp
            195
```

<210> SEQ ID NO 98
<211> LENGTH: 196
<212> TYPE: PRT
<213> ORGANISM: Homo sapiens

<400> SEQUENCE: 98

Asn Ala Val Ala Tyr Tyr Arg Gly Leu Asp Val Ser Val Ile Pro Thr
1               5                   10                  15

Ser Gly Asp Val Val Val Ala Thr Asp Ala Leu Met Thr Gly Phe
            20                  25                  30

Thr Gly Asp Phe Asp Ser Val Ile Asp Cys Asn Thr Cys Val Thr Gln
        35                  40                  45

Thr Val Asp Phe Ser Leu Asp Pro Thr Phe Thr Ile Glu Thr Thr Thr
    50                  55                  60

Val Pro Gln Asp Ala Val Ser Arg Ser Gln Arg Gly Arg Thr Gly
65                  70                  75                  80

Arg Gly Arg Arg Gly Ile Tyr Arg Phe Val Thr Pro Gly Glu Arg Pro
                85                  90                  95

Ser Gly Met Phe Asp Ser Ser Val Leu Cys Glu Cys Tyr Asp Ala Gly
            100                 105                 110

Cys Ala Trp Tyr Glu Leu Thr Pro Ala Glu Thr Ser Val Arg Leu Arg
            115                 120                 125

Ala Tyr Leu Asn Thr Pro Gly Leu Pro Val Cys Gln Asp His Leu Glu
        130                 135                 140

Phe Trp Glu Gly Val Phe Thr Gly Leu Thr His Ile Asp Ala His Phe
145                 150                 155                 160

Leu Ser Gln Thr Lys Gln Ala Gly Asp Asn Phe Pro Tyr Leu Val Ala
                165                 170                 175

Tyr Gln Ala Thr Val Cys Ala Arg Ala Gln Ala Pro Pro Pro Ser Trp
            180                 185                 190

Asp Gln Met Trp
        195

<210> SEQ ID NO 99
<211> LENGTH: 47
<212> TYPE: PRT
<213> ORGANISM: Homo sapiens

<400> SEQUENCE: 99

Thr His Pro Ile Thr Lys Tyr Ile Met Ala Cys Met Ser Ala Asp Leu
1               5                   10                  15

Glu Val Val Thr Ser Thr Trp Val Leu Val Gly Gly Val Leu Ala Ala
            20                  25                  30

Leu Ala Ala Tyr Cys Leu Ser Val Gly Cys Val Val Ile Val Gly
            35                  40                  45

<210> SEQ ID NO 100
<211> LENGTH: 47
<212> TYPE: PRT
<213> ORGANISM: Homo sapiens

<400> SEQUENCE: 100

Thr His Pro Ile Thr Lys Tyr Ile Met Ala Cys Met Ser Ala Asp Leu
1               5                   10                  15

Glu Val Val Thr Ser Thr Trp Val Leu Val Gly Gly Val Leu Ala Ala
            20                  25                  30

Leu Ala Ala Tyr Cys Leu Ser Val Gly Ser Val Val Ile Val Gly
            35                  40                  45

<210> SEQ ID NO 101
<211> LENGTH: 42
<212> TYPE: PRT

<213> ORGANISM: Homo sapiens

<400> SEQUENCE: 101

Phe Trp Ala Lys His Met Trp Asn Phe Ile Ser Gly Ile Gln Tyr Leu
1               5                   10                  15
Ala Gly Leu Ser Thr Leu Pro Gly Asn Pro Ala Val Ala Ser Leu Met
            20                  25                  30
Ala Phe Thr Ala Ala Val Thr Ser Pro Leu
        35                  40

<210> SEQ ID NO 102
<211> LENGTH: 42
<212> TYPE: PRT
<213> ORGANISM: Homo sapiens

<400> SEQUENCE: 102

Phe Trp Ala Lys His Met Trp Asn Phe Ile Ser Gly Ile Gln Tyr Leu
1               5                   10                  15
Ala Gly Leu Ser Thr Leu Pro Gly Asn Pro Ala Ile Ala Ser Leu Met
            20                  25                  30
Ala Phe Thr Ala Ala Val Thr Ser Pro Leu
        35                  40

<210> SEQ ID NO 103
<211> LENGTH: 109
<212> TYPE: PRT
<213> ORGANISM: Homo sapiens

<400> SEQUENCE: 103

Gly Ala Ala Val Gly Ser Ile Gly Leu Gly Lys Val Leu Val Asp Ile
1               5                   10                  15
Leu Ala Gly Tyr Gly Ala Gly Val Ala Gly Ala Leu Val Ala Phe Lys
            20                  25                  30
Ile Met Ser Gly Glu Lys Pro Ser Thr Glu Asp Leu Val Asn Leu Leu
        35                  40                  45
Pro Ala Ile Leu Ser Pro Gly Ala Leu Val Val Gly Val Val Cys Ala
    50                  55                  60
Ala Ile Leu Arg Arg His Val Gly Pro Gly Glu Gly Ala Val Gln Trp
65                  70                  75                  80
Met Asn Arg Leu Ile Ala Phe Ala Ser Arg Gly Asn His Val Ser Pro
                85                  90                  95
Thr His Tyr Val Pro Glu Ser Asp Ala Ala Arg Val
            100                 105

<210> SEQ ID NO 104
<211> LENGTH: 109
<212> TYPE: PRT
<213> ORGANISM: Homo sapiens

<400> SEQUENCE: 104

Gly Ala Ala Val Gly Ser Val Gly Leu Gly Lys Val Leu Val Asp Ile
1               5                   10                  15
Leu Ala Gly Tyr Gly Ala Gly Val Ala Gly Ala Leu Val Ala Phe Lys
            20                  25                  30
Ile Met Ser Gly Glu Val Pro Ser Thr Glu Asp Leu Val Asn Leu Leu
        35                  40                  45
Pro Ala Ile Leu Ser Pro Gly Ala Leu Val Val Gly Val Val Cys Ala
    50                  55                  60

```
Ala Ile Leu Arg Arg His Val Gly Pro Gly Glu Gly Ala Val Gln Trp
 65                  70                  75                  80

Met Asn Arg Leu Ile Ala Phe Ala Ser Arg Gly Asn His Val Ser Pro
                 85                  90                  95

Thr His Tyr Val Pro Glu Ser Asp Ala Ala Ala Arg Val
            100                 105
```

<210> SEQ ID NO 105
<211> LENGTH: 35
<212> TYPE: PRT
<213> ORGANISM: Homo sapiens

<400> SEQUENCE: 105

```
Thr Ala Glu Thr Ala Ala Arg Arg Leu Ala Arg Gly Ser Pro Pro Ser
  1               5                  10                  15

Leu Ala Ser Ser Ser Ala Ser Gln Leu Ser Ala Pro Ser Leu Lys Ala
                 20                  25                  30

Thr Cys Thr
         35
```

<210> SEQ ID NO 106
<211> LENGTH: 59
<212> TYPE: PRT
<213> ORGANISM: Homo sapiens

<400> SEQUENCE: 106

```
Val Cys Cys Ser Met Ser Tyr Ser Trp Thr Gly Ala Leu Ile Thr Pro
  1               5                  10                  15

Cys Ala Ala Glu Glu Lys Leu Pro Ile Asn Pro Leu Ser Asn Ser
                 20                  25                  30

Leu Leu Arg His His Asn Leu Val Tyr Ser Thr Thr Ser Arg Ser Ala
                 35                  40                  45

Ser Leu Arg Gln Lys Lys Val Thr Phe Asp Arg
 50                  55
```

<210> SEQ ID NO 107
<211> LENGTH: 59
<212> TYPE: PRT
<213> ORGANISM: Homo sapiens

<400> SEQUENCE: 107

```
Val Cys Cys Ser Met Ser Tyr Ser Trp Thr Gly Ala Leu Ile Thr Pro
  1               5                  10                  15

Cys Ala Ala Glu Glu Lys Leu Pro Ile Asn Pro Leu Ser Asn Ser
                 20                  25                  30

Leu Ile Arg His His Asn Met Val Tyr Ser Thr Thr Ser Arg Ser Ala
                 35                  40                  45

Ser Leu Arg Gln Lys Lys Val Thr Phe Asp Arg
 50                  55
```

<210> SEQ ID NO 108
<211> LENGTH: 30
<212> TYPE: PRT
<213> ORGANISM: Homo sapiens

<400> SEQUENCE: 108

```
Pro Ser Lys Gly Gly Arg Lys Pro Ala Arg Leu Ile Val Tyr Pro Asp
  1               5                  10                  15

Leu Gly Val Arg Val Cys Glu Lys Arg Ala Leu Tyr Asp Val
                 20                  25                  30
```

<210> SEQ ID NO 109
<211> LENGTH: 26
<212> TYPE: PRT
<213> ORGANISM: Homo sapiens

<400> SEQUENCE: 109

Lys Lys Thr Pro Met Gly Phe Ser Tyr Asp Thr Arg Cys Phe Asp Ser
1               5                   10                  15

Thr Val Thr Glu Arg Asp Ile Arg Thr Glu
            20                  25

<210> SEQ ID NO 110
<211> LENGTH: 29
<212> TYPE: PRT
<213> ORGANISM: Homo sapiens

<400> SEQUENCE: 110

Cys Gly Tyr Arg Arg Cys Arg Ala Ser Gly Val Leu Thr Thr Ser Met
1               5                   10                  15

Gly Asn Thr Leu Thr Cys Tyr Ile Lys Ala Leu Ala Ala
            20                  25

<210> SEQ ID NO 111
<211> LENGTH: 29
<212> TYPE: PRT
<213> ORGANISM: Homo sapiens

<400> SEQUENCE: 111

Cys Gly Tyr Arg Arg Cys Arg Ala Ser Gly Val Leu Thr Thr Ser Met
1               5                   10                  15

Gly Asn Thr Ile Thr Cys Tyr Ile Lys Ala Leu Ala Ala
            20                  25

<210> SEQ ID NO 112
<211> LENGTH: 35
<212> TYPE: PRT
<213> ORGANISM: Homo sapiens

<400> SEQUENCE: 112

Glu Ala Met Thr Arg Tyr Ser Ala Pro Pro Gly Asp Pro Pro Gln Pro
1               5                   10                  15

Glu Tyr Asp Leu Glu Leu Ile Thr Ser Cys Ser Ser Asn Val Ser Val
            20                  25                  30

Ala His Asp
        35

<210> SEQ ID NO 113
<211> LENGTH: 45
<212> TYPE: PRT
<213> ORGANISM: Homo sapiens

<400> SEQUENCE: 113

Thr Pro Leu Ala Arg Ala Ala Trp Glu Thr Ala Arg His Thr Pro Val
1               5                   10                  15

Asn Ser Trp Leu Gly Asn Ile Ile Met Tyr Ala Pro Thr Ile Trp Val
            20                  25                  30

Arg Met Val Leu Met Thr His Phe Phe Ser Ile Leu Gln
        35                  40                  45

<210> SEQ ID NO 114

<211> LENGTH: 31
<212> TYPE: PRT
<213> ORGANISM: Homo sapiens

<400> SEQUENCE: 114

Tyr Gly Ala Thr Tyr Ser Val Thr Pro Leu Asp Leu Pro Ala Ile Ile
1               5                   10                  15

Gln Arg Leu His Gly Leu Ser Ala Phe Ser Leu His Ser Tyr Ser
            20                  25                  30

<210> SEQ ID NO 115
<211> LENGTH: 31
<212> TYPE: PRT
<213> ORGANISM: Homo sapiens

<400> SEQUENCE: 115

Tyr Gly Ala Thr Tyr Ser Val Thr Pro Leu Asp Leu Pro Ala Ile Ile
1               5                   10                  15

Glu Arg Leu His Gly Leu Ser Ala Phe Thr Leu His Ser Tyr Ser
            20                  25                  30

<210> SEQ ID NO 116
<211> LENGTH: 50
<212> TYPE: PRT
<213> ORGANISM: Homo sapiens

<400> SEQUENCE: 116

Glu Leu Asn Arg Val Ala Ala Cys Leu Arg Lys Leu Gly Val Pro Pro
1               5                   10                  15

Leu Arg Ala Trp Arg His Arg Ala Arg Ala Val Arg Ala Lys Leu Ile
            20                  25                  30

Ala Gln Gly Gly Arg Ala Ala Ile Cys Gly Lys Tyr Leu Phe Asn Trp
        35                  40                  45

Ala Val
    50

<210> SEQ ID NO 117
<211> LENGTH: 50
<212> TYPE: PRT
<213> ORGANISM: Homo sapiens

<400> SEQUENCE: 117

Glu Leu Asn Arg Val Gly Ala Cys Leu Arg Lys Leu Gly Val Pro Pro
1               5                   10                  15

Leu Arg Ala Trp Arg His Arg Ala Arg Ala Val Arg Ala Lys Leu Ile
            20                  25                  30

Ala Gln Gly Gly Lys Ala Ala Ile Cys Gly Lys Tyr Leu Phe Asn Trp
        35                  40                  45

Ala Val
    50

<210> SEQ ID NO 118
<211> LENGTH: 1123
<212> TYPE: PRT
<213> ORGANISM: Homo sapiens

<400> SEQUENCE: 118

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

```
Lys Gly Gly Gly Pro Gly Gly Lys Ser Thr Asn Pro Lys Pro Gln
        35                  40                  45

Arg Lys Thr Lys Arg Asn Thr Asn Arg Arg Pro Gln Asp Val Lys Phe
        50                  55                  60

Pro Gly Gly Gly Gln Ile Val Gly Gly Val Tyr Leu Leu Pro Arg Arg
65                  70                  75                  80

Gly Pro Arg Leu Gly Val Arg Ala Thr Arg Lys Thr Ser Glu Arg Ser
                85                  90                  95

Gln Pro Arg Gly Arg Arg Gln Pro Ile Pro Lys Ala Arg Arg Pro Glu
                100                 105                 110

Gly Arg Thr Trp Ala Gln Pro Gly Tyr Pro Trp Pro Leu Tyr Gly Asn
            115                 120                 125

Glu Gly Cys Gly Trp Ala Gly Trp Leu Leu Ser Pro Arg Gly Ser Arg
            130                 135                 140

Pro Ser Trp Gly Pro Thr Asp Pro Arg Arg Ser Arg Asn Leu Gly
145                 150                 155                 160

Lys Val Ile Asp Thr Leu Thr Cys Gly Phe Ala Asp Leu Met Gly Tyr
                165                 170                 175

Ile Pro Leu Val Gly Ala Pro Leu Gly Gly Ala Ala Arg Ala Leu Ala
                180                 185                 190

His Gly Val Arg Val Leu Glu Asp Gly Val Asn Tyr Ala Thr Gly Asn
            195                 200                 205

Leu Pro Gly Cys Ser Phe Ser Ile Phe Leu Leu Ala Leu Leu Ser Cys
            210                 215                 220

Leu Thr Val Pro Ala Ser Ala Gly Gly Ser Gly Asp Arg Asp Arg Ser
225                 230                 235                 240

Glu Leu Ser Pro Leu Leu Leu Ser Thr Thr Gln Trp Gln Val Leu Pro
                245                 250                 255

Cys Ser Phe Thr Thr Leu Pro Ala Leu Ser Thr Gly Leu Ile His Leu
            260                 265                 270

His Gln Asn Ile Val Asp Val Gln Tyr Leu Tyr Gly Val Gly Ser Ser
            275                 280                 285

Val Gly Pro Pro Cys Thr Cys Gly Ser Ser Asp Leu Tyr Leu Val Thr
            290                 295                 300

Arg His Ala Asp Val Ile Pro Val Arg Arg Arg Gly Asp Ser Arg Gly
305                 310                 315                 320

Ser Leu Leu Ser Pro Arg Pro Ile Ser Tyr Leu Lys Gly Ser Ser Gly
                325                 330                 335

Gly Pro Leu Leu Cys Pro Ser Gly His Ala Val Gly Ile Phe Arg Ala
            340                 345                 350

Ala Val Cys Thr Arg Gly Val Ala Lys Ala Val Asp Phe Ile Pro Val
            355                 360                 365

Glu Ser Met Glu Thr Thr Met Arg Ser Pro Val Phe Thr Asp Asn Ser
370                 375                 380

Ser Pro Pro Ala Val Pro Gln Thr Phe Gln Val Ala His Leu His Ala
385                 390                 395                 400

Pro Thr Gly Ser Gly Lys Ser Thr Lys Val Pro Ala Ala Tyr Ala Ala
                405                 410                 415

Gln Gly Tyr Lys Val Leu Val Leu Asn Pro Ser Val Ala Ala Thr Leu
                420                 425                 430

Gly Phe Gly Ala Tyr Met Ser Lys Ala His Gly Val Ser Gly Thr Gly
            435                 440                 445
```

```
Val Arg Thr Ile Thr Thr Gly Ser Pro Ile Thr Tyr Ser Thr Tyr Gly
450                 455                 460

Lys Phe Leu Ala Asp Gly Gly Cys Ser Gly Gly Ala Tyr Asp Ile Ile
465                 470                 475                 480

Ile Cys Asp Glu Cys His Ser Thr Asp Ala Thr Ser Ile Leu Gly Ile
            485                 490                 495

Gly Thr Val Leu Asp Gln Ala Glu Thr Ala Gly Ala Arg Leu Val Val
                500                 505                 510

Leu Ala Thr Ala Thr Pro Pro Gly Ser Val Thr Val Pro His Pro Asn
            515                 520                 525

Ile Glu Glu Val Gly Pro Gly Asn Ala Val Ala Tyr Tyr Arg Gly Leu
530                 535                 540

Asp Val Ser Val Ile Pro Thr Ser Gly Asp Val Val Val Ala Thr
545                 550                 555                 560

Asp Ala Leu Met Thr Gly Phe Thr Gly Asp Phe Asp Ser Val Ile Asp
                565                 570                 575

Cys Asn Thr Cys Val Thr Gln Thr Val Asp Phe Ser Leu Asp Pro Thr
            580                 585                 590

Phe Thr Ile Glu Thr Thr Thr Leu Pro Gln Asp Ala Val Ser Arg Thr
            595                 600                 605

Gln Arg Arg Gly Arg Thr Gly Arg Gly Arg Pro Gly Gly Gly Ser Gly
610                 615                 620

Gly Gly Tyr Arg Phe Val Thr Pro Gly Glu Arg Pro Ser Gly Met Phe
625                 630                 635                 640

Asp Ser Ser Val Leu Cys Glu Cys Tyr Asp Ala Gly Cys Ala Trp Tyr
                645                 650                 655

Glu Leu Thr Pro Ala Glu Thr Thr Val Arg Leu Arg Ala Tyr Leu Asn
            660                 665                 670

Thr Pro Gly Leu Pro Val Cys Gln Asp His Leu Glu Phe Trp Glu Gly
            675                 680                 685

Val Phe Thr Gly Leu Thr His Ile Asp Ala His Phe Leu Ser Gln Thr
690                 695                 700

Lys Gln Ala Gly Asp Asn Phe Pro Tyr Leu Val Ala Tyr Gln Ala Thr
705                 710                 715                 720

Val Cys Ala Arg Ala Gln Ala Pro Pro Pro Ser Trp Asp Gln Met Trp
                725                 730                 735

Lys Cys Leu Ile Arg Leu Lys Pro Gly Gly Lys Gly Pro Gly Lys
            740                 745                 750

Tyr Ile Met Thr Cys Met Ser Ala Asp Leu Glu Val Val Thr Ser Thr
            755                 760                 765

Trp Val Leu Val Gly Gly Val Leu Ala Ala Leu Ala Ala Tyr Cys Leu
770                 775                 780

Ser Thr Gly Cys Val Val Ile Val Gly Arg Ile Val Leu Ser Gly Gly
785                 790                 795                 800

Ser Gly Gly Ser Ile Gly Leu Gly Lys Val Leu Val Asp Ile Leu Ala
                805                 810                 815

Gly Tyr Gly Ala Gly Val Ala Gly Ala Leu Val Ala Phe Lys Ile Met
            820                 825                 830

Ser Gly Glu Val Pro Ser Thr Glu Asp Leu Val Asn Leu Leu Pro Ala
            835                 840                 845

Ile Leu Ser Pro Gly Ala Leu Val Val Gly Val Cys Ala Ala Ile
850                 855                 860

Leu Arg Arg His Val Gly Pro Gly Glu Gly Ala Val Gln Trp Met Asn
```

```
             865                 870                 875                 880
Arg Leu Ile Ala Phe Ala Ser Arg Gly Asn His Val Ser Pro Thr His
                        885                 890                 895

Tyr Val Pro Glu Ser Asp Ala Ala Arg Val Thr Gln Ile Leu Ser
                900                 905                 910

Gly Pro Ser Leu Thr Glu Arg Leu Tyr Val Gly Pro Leu Thr Asn
                915                 920                 925

Ser Lys Gly Gln Asn Cys Gly Tyr Arg Cys Arg Ala Ser Gly Val
        930                 935                 940

Leu Thr Thr Ser Cys Gly Asn Thr Leu Thr Cys Tyr Leu Lys Ala Ser
945                 950                 955                 960

Ala Ala Cys Arg Ala Ala Lys Leu Gly Pro Gly Ser Leu Arg Ala
                965                 970                 975

Phe Thr Glu Ala Met Thr Arg Tyr Ser Ala Pro Pro Gly Asp Pro Pro
                980                 985                 990

Gln Pro Glu Tyr Asp Leu Glu Leu Ile Thr Ser Cys Ser Ser Asn Val
                995                 1000                1005

Ser Val Ala His Asp Ala Ser Gly Lys Arg Val Tyr Tyr Leu Thr
    1010                1015                1020

Arg Asp Pro Thr Thr Pro Leu Ala Arg Ala Ala Trp Glu Thr Ala
    1025                1030                1035

Arg His Thr Pro Val Asn Ser Trp Leu Gly Asn Ile Met Tyr
    1040                1045                1050

Ala Pro Thr Leu Trp Ala Arg Met Ile Leu Gly Ser Gly Gly
    1055                1060                1065

Glu Pro Leu Asp Leu Pro Gln Ile Ile Gln Arg Leu His Gly Leu
    1070                1075                1080

Ser Ala Phe Ser Leu His Ser Tyr Ser Pro Gly Glu Ile Asn Arg
    1085                1090                1095

Val Ala Ala Cys Leu Arg Lys Leu Gly Val Pro Pro Leu Arg Ala
    1100                1105                1110

Trp Arg His Arg Ala Arg Ser Val Arg Ala
    1115                1120

<210> SEQ ID NO 119
<211> LENGTH: 1655
<212> TYPE: PRT
<213> ORGANISM: Homo sapiens

<400> SEQUENCE: 119

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Lys Gly Gly Pro Gly Gly Gly Lys Ser Thr Asn Pro Lys Pro Gln
        35                  40                  45

Arg Lys Thr Lys Arg Asn Thr Asn Arg Arg Pro Gln Asp Val Lys Phe
    50                  55                  60

Pro Gly Gly Gly Gln Ile Val Gly Gly Val Tyr Leu Leu Pro Arg Arg
65                  70                  75                  80

Gly Pro Arg Leu Gly Val Arg Ala Thr Arg Lys Thr Ser Glu Arg Ser
                85                  90                  95

Gln Pro Arg Gly Arg Arg Gln Pro Ile Pro Lys Ala Arg Arg Pro Glu
                100                 105                 110
```

```
Gly Arg Thr Trp Ala Gln Pro Gly Tyr Pro Trp Pro Leu Tyr Gly Asn
        115                 120                 125

Glu Gly Cys Gly Trp Ala Gly Trp Leu Leu Ser Pro Arg Gly Ser Arg
    130                 135                 140

Pro Ser Trp Gly Pro Thr Asp Pro Arg Arg Ser Arg Asn Leu Gly
145                 150                 155                 160

Lys Val Ile Asp Thr Leu Thr Cys Gly Phe Ala Asp Leu Met Gly Tyr
                165                 170                 175

Ile Pro Leu Val Gly Ala Pro Leu Gly Ala Ala Arg Ala Leu Ala
                180                 185                 190

His Gly Val Arg Val Leu Glu Asp Gly Val Asn Tyr Ala Thr Gly Asn
            195                 200                 205

Leu Pro Gly Cys Ser Phe Ser Ile Phe Leu Leu Ala Leu Leu Ser Cys
210                 215                 220

Leu Thr Val Pro Ala Ser Ala Gly Gly Ser Gly Tyr Val Gly Asp Leu
225                 230                 235                 240

Cys Gly Ser Val Phe Leu Val Ser Gln Leu Phe Thr Phe Ser Pro Arg
                245                 250                 255

Pro Tyr Pro Gly His Ile Thr Gly His Arg Met Ala Trp Asp Met Met
            260                 265                 270

Met Asn Trp Ser Pro Val Cys Gly Pro Val Tyr Cys Phe Thr Pro Ser
        275                 280                 285

Pro Val Val Gly Thr Thr Asp Arg Thr Asp Val Phe Leu Leu Asn
        290                 295                 300

Asn Thr Arg Pro Pro Leu Gly Asn Trp Phe Gly Cys Thr Trp Met Cys
305                 310                 315                 320

Pro Thr Asp Cys Phe Arg Lys His Pro Glu Ala Thr Tyr Ser Arg Cys
                325                 330                 335

Gly Ser Gly Pro Trp Leu Thr Pro Arg Cys Leu Val Asp Tyr Pro Tyr
                340                 345                 350

Arg Leu Trp Gly Asp Arg Asp Arg Ser Glu Leu Ser Pro Leu Leu Leu
            355                 360                 365

Ser Thr Thr Gln Trp Gln Val Leu Pro Cys Ser Phe Thr Thr Leu Pro
        370                 375                 380

Ala Leu Ser Thr Gly Leu Ile His Leu His Gln Asn Ile Val Asp Val
385                 390                 395                 400

Gln Tyr Leu Tyr Gly Val Gly Ser Ser Val Ala Arg Val Cys Ala Cys
                405                 410                 415

Leu Trp Met Met Leu Leu Ile Ala Gln Ala Glu Ala Leu Glu Asn
        420                 425                 430

Leu Val Lys Gly Trp Arg Leu Leu Ala Pro Ile Thr Ala Tyr Ala Gln
            435                 440                 445

Gln Thr Arg Gly Leu Leu Gly Cys Ile Ile Thr Ser Leu Thr Gly Arg
    450                 455                 460

Asp Lys Asn Gln Val Glu Gly Glu Val Gln Ile Val Ser Thr Gln Ser
465                 470                 475                 480

Phe Leu Ala Thr Cys Ile Asn Gly Val Cys Trp Thr Val Tyr His Gly
                485                 490                 495

Ala Gly Pro Cys Thr Cys Gly Ser Ser Asp Leu Tyr Leu Val Thr Arg
                500                 505                 510

His Ala Asp Val Ile Pro Val Arg Arg Arg Gly Asp Ser Arg Gly Ser
            515                 520                 525

Leu Leu Ser Pro Arg Pro Ile Ser Tyr Leu Lys Gly Ser Ser Gly Gly
```

```
                530             535             540
Pro Leu Leu Cys Pro Ser Gly His Ala Val Gly Ile Phe Arg Ala Ala
545                 550                 555                 560

Val Cys Thr Arg Gly Val Ala Lys Ala Val Asp Phe Ile Pro Val Glu
                565                 570                 575

Ser Met Glu Thr Thr Met Arg Ser Pro Val Phe Thr Asp Asn Ser Ser
                580                 585                 590

Pro Pro Ala Val Pro Gln Thr Phe Gln Val Ala His Leu His Ala Pro
                595                 600                 605

Thr Gly Ser Gly Lys Ser Thr Lys Val Pro Ala Ala Tyr Ala Ala Gln
                610                 615                 620

Gly Tyr Lys Val Leu Val Leu Asn Pro Ser Val Ala Ala Thr Leu Gly
625                 630                 635                 640

Phe Gly Ala Tyr Met Ser Lys Ala His Gly Val Ser Gly Thr Gly Val
                645                 650                 655

Arg Thr Ile Thr Thr Gly Ser Pro Ile Thr Tyr Ser Thr Tyr Gly Lys
                660                 665                 670

Phe Leu Ala Asp Gly Gly Cys Ser Gly Gly Ala Tyr Asp Ile Ile Ile
                675                 680                 685

Cys Asp Glu Cys His Ser Thr Asp Ala Thr Ser Ile Leu Gly Ile Gly
                690                 695                 700

Thr Val Leu Asp Gln Ala Glu Thr Ala Gly Ala Arg Leu Val Val Leu
705                 710                 715                 720

Ala Thr Ala Thr Pro Pro Gly Ser Val Thr Val Pro His Pro Asn Ile
                725                 730                 735

Glu Glu Val Gly Pro Gly Asn Ala Val Ala Tyr Tyr Arg Gly Leu Asp
                740                 745                 750

Val Ser Val Ile Pro Thr Ser Gly Asp Val Val Val Ala Thr Asp
                755                 760                 765

Ala Leu Met Thr Gly Phe Thr Gly Asp Phe Asp Ser Val Ile Asp Cys
770                 775                 780

Asn Thr Cys Val Thr Gln Thr Val Asp Phe Ser Leu Asp Pro Thr Phe
785                 790                 795                 800

Thr Ile Glu Thr Thr Thr Leu Pro Gln Asp Ala Val Ser Arg Thr Gln
                805                 810                 815

Arg Arg Gly Arg Thr Gly Arg Gly Arg Pro Gly Gly Gly Ser Gly Gly
                820                 825                 830

Gly Tyr Arg Phe Val Thr Pro Gly Glu Arg Pro Ser Gly Met Phe Asp
                835                 840                 845

Ser Ser Val Leu Cys Glu Cys Tyr Asp Ala Gly Cys Ala Trp Tyr Glu
850                 855                 860

Leu Thr Pro Ala Glu Thr Thr Val Arg Leu Arg Ala Tyr Leu Asn Thr
865                 870                 875                 880

Pro Gly Leu Pro Val Cys Gln Asp His Leu Glu Phe Trp Glu Gly Val
                885                 890                 895

Phe Thr Gly Leu Thr His Ile Asp Ala His Phe Leu Ser Gln Thr Lys
                900                 905                 910

Gln Ala Gly Asp Asn Phe Pro Tyr Leu Val Ala Tyr Gln Ala Thr Val
                915                 920                 925

Cys Ala Arg Ala Gln Ala Pro Pro Ser Trp Asp Gln Met Trp Lys
                930                 935                 940

Cys Leu Ile Arg Leu Lys Pro Gly Gly Lys Gly Pro Gly Gly Lys Tyr
945                 950                 955                 960
```

```
Ile Met Thr Cys Met Ser Ala Asp Leu Glu Val Val Thr Ser Thr Trp
            965                 970                 975

Val Leu Val Gly Gly Val Leu Ala Ala Leu Ala Ala Tyr Cys Leu Ser
            980                 985                 990

Thr Gly Cys Val Val Ile Val Gly Arg Ile Val Leu Ser Gly Gly Pro
            995                 1000                1005

Gly Phe Trp Ala Lys His Met Trp Asn Phe Ile Ser Gly Ile Gln
        1010                1015                1020

Tyr Leu Ala Gly Leu Ser Thr Leu Pro Gly Asn Pro Ala Ile Ala
        1025                1030                1035

Ser Leu Met Ala Phe Thr Ala Ser Val Thr Ser Pro Leu Thr Thr
        1040                1045                1050

Gln Pro Gly Ser Ile Gly Leu Gly Lys Val Leu Val Asp Ile Leu
        1055                1060                1065

Ala Gly Tyr Gly Ala Gly Val Ala Gly Ala Leu Val Ala Phe Lys
        1070                1075                1080

Ile Met Ser Gly Glu Val Pro Ser Thr Glu Asp Leu Val Asn Leu
        1085                1090                1095

Leu Pro Ala Ile Leu Ser Pro Gly Ala Leu Val Val Gly Val Val
        1100                1105                1110

Cys Ala Ala Ile Leu Arg Arg His Val Gly Pro Gly Glu Gly Ala
        1115                1120                1125

Val Gln Trp Met Asn Arg Leu Ile Ala Phe Ala Ser Arg Gly Asn
        1130                1135                1140

His Val Ser Pro Thr His Tyr Val Pro Glu Ser Asp Ala Ala Ala
        1145                1150                1155

Arg Val Thr Gln Ile Leu Ser Ser Trp Leu Arg Asp Ile Trp Asp
        1160                1165                1170

Trp Ile Cys Glu Val Leu Ser Asp Phe Lys Thr Trp Leu Lys Cys
        1175                1180                1185

Pro Cys Gln Val Pro Ser Pro Glu Phe Phe Thr Glu Leu Asp Gly
        1190                1195                1200

Val Arg Leu His Arg Lys Lys Gly Pro Gly Ser Gly Pro Gly Pro
        1205                1210                1215

Arg Arg Leu Ala Arg Gly Ser Pro Pro Ser Leu Ala Ser Ser Ser
        1220                1225                1230

Ala Ser Gln Leu Ser Ala Pro Ser Leu Lys Ala Thr Cys Thr Thr
        1235                1240                1245

Asn His Ser Asp Ala Glu Ser Tyr Ser Ser Met Pro Pro Leu Glu
        1250                1255                1260

Gly Glu Pro Gly Asp Pro Asp Leu Ser Asp Gly Ser Trp Ser Thr
        1265                1270                1275

Val Ser Ser Glu Ala Gly Ser Gly Ser Leu Ser Asn Ser Leu Leu
        1280                1285                1290

Arg His His Asn Met Val Tyr Ala Thr Thr Ser Arg Ser Ala Gly
        1295                1300                1305

Pro Leu Thr Pro Pro His Ser Ala Lys Ser Lys Phe Gly Tyr Gly
        1310                1315                1320

Ala Lys Asp Val Arg Cys His Ser Gly Ser Gly Gly Ser Lys
        1325                1330                1335

Pro Ala Arg Leu Ile Val Phe Pro Asp Leu Gly Val Arg Val Cys
        1340                1345                1350
```

Glu Lys Met Ala Leu Tyr Asp Val Val Gly Gly Pro Met Gly Phe
1355                1360                1365

Ser Tyr Asp Thr Arg Cys Phe Asp Ser Thr Val Thr Glu Ser Asp
1370                1375                1380

Ile Arg Thr Glu Gly Gly Ser Gly Gly Gly Ser Leu Thr Glu Arg
1385                1390                1395

Leu Tyr Val Gly Gly Pro Leu Thr Asn Ser Lys Gly Gln Asn Cys
1400                1405                1410

Gly Tyr Arg Arg Cys Arg Ala Ser Gly Val Leu Thr Thr Ser Cys
1415                1420                1425

Gly Asn Thr Leu Thr Cys Tyr Leu Lys Ala Ser Ala Ala Cys Arg
1430                1435                1440

Ala Ala Lys Leu Gly Gly Ser Gly Gly Cys Thr Met Leu Val Cys
1445                1450                1455

Gly Asp Asp Leu Val Val Ile Cys Glu Ser Ala Gly Thr Gln Glu
1460                1465                1470

Asp Ala Ser Leu Arg Ala Phe Thr Glu Ala Met Thr Arg Tyr Ser
1475                1480                1485

Ala Pro Pro Gly Asp Pro Pro Gln Pro Glu Tyr Asp Leu Glu Leu
1490                1495                1500

Ile Thr Ser Cys Ser Ser Asn Val Ser Val Ala His Asp Ala Ser
1505                1510                1515

Gly Lys Arg Val Tyr Tyr Leu Thr Arg Asp Pro Thr Thr Pro Leu
1520                1525                1530

Ala Arg Ala Ala Trp Glu Thr Ala Arg His Thr Pro Val Asn Ser
1535                1540                1545

Trp Leu Gly Asn Ile Ile Met Tyr Ala Pro Thr Leu Trp Ala Arg
1550                1555                1560

Met Ile Leu Gly Gly Ser Gly Gly Glu Pro Leu Asp Leu Pro Gln
1565                1570                1575

Ile Ile Gln Arg Leu His Gly Leu Ser Ala Phe Ser Leu His Ser
1580                1585                1590

Tyr Ser Pro Gly Glu Ile Asn Arg Val Ala Ala Cys Leu Arg Lys
1595                1600                1605

Leu Gly Val Pro Pro Leu Arg Ala Trp Arg His Arg Ala Arg Ser
1610                1615                1620

Val Arg Ala Ser Gly Gly Arg Ala Ala Ile Cys Gly Lys Tyr Leu
1625                1630                1635

Phe Asn Trp Ala Val Arg Thr Lys Leu Lys Leu Thr Pro Ile Pro
1640                1645                1650

Ala Ala
1655

<210> SEQ ID NO 120
<211> LENGTH: 1072
<212> TYPE: PRT
<213> ORGANISM: Homo sapiens

<400> SEQUENCE: 120

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Lys Gly Gly Gly Pro Gly Gly Gly Lys Ser Thr Asn Pro Lys Pro Gln
        35                  40                  45

-continued

```
Arg Lys Thr Lys Arg Asn Thr Asn Arg Arg Pro Gln Asp Val Lys Phe
 50                  55                  60

Pro Gly Gly Gly Gln Ile Val Gly Gly Val Tyr Leu Leu Pro Arg Arg
 65                      70                  75                  80

Gly Pro Arg Leu Gly Val Arg Ala Thr Arg Lys Thr Ser Glu Arg Ser
                 85                  90                  95

Gln Pro Arg Gly Arg Arg Gln Pro Ile Pro Lys Ala Arg Arg Pro Glu
             100                 105                 110

Gly Arg Ser Trp Ala Gln Pro Gly Tyr Pro Trp Pro Leu Tyr Gly Asn
         115                 120                 125

Glu Gly Cys Gly Trp Ala Gly Trp Leu Leu Ser Pro Arg Gly Ser Arg
 130                 135                 140

Pro Ser Trp Gly Pro Thr Asp Pro Arg Arg Ser Arg Asn Leu Gly
145                 150                 155                 160

Lys Val Ile Asp Thr Leu Thr Cys Gly Phe Ala Asp Leu Met Gly Tyr
                 165                 170                 175

Ile Pro Leu Val Gly Ala Pro Leu Gly Gly Ala Ala Arg Ala Leu Ala
             180                 185                 190

His Gly Val Arg Val Leu Glu Asp Gly Val Asn Tyr Ala Thr Gly Asn
         195                 200                 205

Leu Pro Gly Cys Ser Phe Ser Ile Phe Leu Leu Ala Leu Leu Ser Cys
 210                 215                 220

Leu Thr Val Pro Ala Ser Gly Lys Gly Gly Thr Thr Glu Leu Ala Ile
225                 230                 235                 240

Leu Pro Cys Ser Phe Thr Pro Leu Pro Ala Leu Ser Thr Gly Leu Ile
                 245                 250                 255

His Leu His Gln Asn Ile Val Asp Val Gln Tyr Leu Tyr Gly Val Gly
             260                 265                 270

Ser Gly Met Met Gly Trp Arg Leu Leu Ala Pro Ile Thr Ala Tyr Ala
         275                 280                 285

Gln Gln Thr Arg Gly Leu Leu Gly Thr Ile Val Thr Ser Leu Thr Gly
 290                 295                 300

Arg Asp Lys Asn Val Val Thr Gly Glu Val Gln Val Leu Ser Thr Ala
305                 310                 315                 320

Gly Ser Gly Pro Cys Thr Cys Gly Ser Ala Asp Leu Tyr Leu Val Thr
                 325                 330                 335

Arg Asp Ala Asp Val Ile Pro Ala Arg Arg Arg Gly Asp Ser Thr Ala
             340                 345                 350

Ser Leu Leu Ser Pro Arg Pro Leu Ala Cys Leu Lys Gly Ser Ser Gly
         355                 360                 365

Gly Pro Val Met Cys Pro Ser Gly His Val Ala Gly Ile Phe Arg Ala
 370                 375                 380

Ala Val Cys Thr Arg Gly Val Ala Lys Ala Leu Gln Phe Ile Pro Val
385                 390                 395                 400

Glu Thr Leu Arg Ser Pro Val Phe Ser Asp Asn Ser Ser Pro Pro Ala
                 405                 410                 415

Val Pro Gln Ser Tyr Gln Val Ala His Leu His Ala Pro Thr Gly Ser
             420                 425                 430

Gly Lys Ser Thr Lys Val Pro Ala Ala Tyr Ala Ala Gln Gly Tyr Lys
         435                 440                 445

Val Leu Val Leu Asn Pro Ser Val Ala Ala Thr Leu Gly Phe Gly Ala
 450                 455                 460
```

-continued

Tyr Met Ser Lys Ala Thr Gly Asn Arg Thr Ile Thr Thr Gly Ala Lys
465                 470                 475                 480

Leu Thr Tyr Ser Thr Tyr Gly Lys Phe Leu Ala Asp Gly Gly Cys Ser
            485                 490                 495

Gly Gly Ala Tyr Asp Val Ile Ile Cys Asp Glu Cys His Ala Gln Asp
            500                 505                 510

Ala Thr Ser Ile Leu Gly Ile Gly Thr Val Leu Asp Gln Ala Glu Thr
        515                 520                 525

Ala Gly Val Arg Leu Thr Val Leu Ala Thr Ala Thr Pro Pro Gly Ser
    530                 535                 540

Ile Thr Val Pro His Ser Asn Ile Glu Glu Val Ala Leu Ser Val Ile
545                 550                 555                 560

Pro Thr Ala Gly Asp Val Val Cys Ala Thr Asp Ala Leu Met Thr
                565                 570                 575

Gly Phe Thr Gly Asp Phe Asp Ser Val Ile Asp Cys Asn Val Ala Val
            580                 585                 590

Glu Gln Tyr Val Asp Phe Ser Leu Asp Pro Thr Phe Ser Ile Glu Thr
        595                 600                 605

Arg Thr Ala Pro Gln Asp Ala Val Ser Arg Ser Gln Arg Gly Arg
    610                 615                 620

Thr Gly Arg Gly Arg Leu Gly Thr Tyr Arg Tyr Val Gly Pro Gly Glu
625                 630                 635                 640

Arg Pro Ser Gly Met Phe Asp Ser Val Val Leu Cys Glu Cys Tyr Asp
                645                 650                 655

Ala Gly Cys Ala Trp Tyr Glu Leu Gln Pro Ala Glu Thr Thr Val Arg
            660                 665                 670

Leu Arg Ala Tyr Leu Ser Thr Pro Gly Leu Pro Val Cys Gln Asp His
        675                 680                 685

Leu Asp Phe Trp Glu Ser Val Phe Thr Gly Leu Thr His Ile Asp Ala
    690                 695                 700

His Phe Leu Ser Gln Thr Lys Gln Gln Gly Leu Asn Phe Pro Tyr Leu
705                 710                 715                 720

Thr Ala Tyr Gln Ala Thr Val Cys Ala Arg Ala Gln Ala Pro Pro Pro
                725                 730                 735

Ser Trp Asp Glu Met Trp Lys Cys Leu Val Arg Leu Lys Pro Thr Leu
            740                 745                 750

His Gly Pro Thr Pro Leu Leu Tyr Arg Leu Gly Pro Val Gln Asn Gly
        755                 760                 765

Gly Ser Gly Lys Gly Gly Ile Gly Ser Val Gly Leu Gly Lys Val Leu
    770                 775                 780

Val Asp Ile Leu Ala Gly Tyr Gly Ala Gly Val Ala Gly Ala Leu Val
785                 790                 795                 800

Ala Phe Lys Ile Met Ser Gly Glu Ile Pro Ser Thr Glu Asp Leu Val
                805                 810                 815

Asn Leu Leu Pro Ala Ile Leu Ser Pro Gly Ala Leu Val Val Gly Val
            820                 825                 830

Val Cys Ala Ala Ile Leu Arg Arg His Val Gly Pro Gly Glu Gly Ala
        835                 840                 845

Val Gln Trp Met Asn Arg Leu Ile Ala Phe Ala Ser Arg Gly Asn His
    850                 855                 860

Val Ser Pro Thr His Tyr Val Pro Glu Ser Asp Ala Ala Ala Arg Val
865                 870                 875                 880

Thr Ala Ile Leu Ser Ser Leu Thr Ser Gly Gln Ser Val Val Cys Cys

```
                        885                 890                 895
Ser Met Ser Tyr Ser Trp Thr Gly Ala Leu Ile Thr Pro Cys Ser Ala
                900                 905                 910

Glu Glu Glu Lys Leu Pro Ile Asn Pro Leu Ser Asn Ser Leu Leu Arg
            915                 920                 925

His His Asn Leu Val Tyr Ser Thr Ser Ser Arg Ser Ala Ser Gln Arg
        930                 935                 940

Gln Lys Lys Val Thr Phe Asp Arg Leu Gln Val Leu Asp Asp His Tyr
945                 950                 955                 960

Lys Lys Gly Lys Arg Tyr Tyr Leu Thr Arg Asp Pro Thr Thr Pro
                965                 970                 975

Leu Ala Arg Ala Ala Trp Glu Thr Ala Arg His Thr Pro Val Asn Ser
                980                 985                 990

Trp Leu Gly Asn Ile Ile Met Tyr Ala Pro Thr Ile Trp Val Arg Met
            995                 1000                1005

Val Met Gly Lys Gly Pro Gly Ser Tyr Gly Ala Thr Tyr Ser Val
        1010                1015                1020

Thr Pro Leu Asp Leu Pro Ala Ile Ile Glu Arg Leu His Gly Leu
        1025                1030                1035

Ser Ala Phe Thr Leu His Ser Tyr Ser Pro Val Glu Leu Asn Arg
        1040                1045                1050

Val Ala Gly Thr Leu Arg Lys Leu Gly Cys Pro Leu Arg Ala
        1055                1060                1065

Trp Arg His Arg
        1070

<210> SEQ ID NO 121
<211> LENGTH: 1554
<212> TYPE: PRT
<213> ORGANISM: Homo sapiens

<400> SEQUENCE: 121

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Lys Gly Gly Gly Pro Gly Gly Gly Lys Ser Thr Asn Pro Lys Pro Gln
        35                  40                  45

Arg Lys Thr Lys Arg Asn Thr Asn Arg Arg Pro Gln Asp Val Lys Phe
    50                  55                  60

Pro Gly Gly Gly Gln Ile Val Gly Gly Val Tyr Leu Leu Pro Arg Arg
65                  70                  75                  80

Gly Pro Arg Leu Gly Val Arg Ala Thr Arg Lys Thr Ser Glu Arg Ser
                85                  90                  95

Gln Pro Arg Gly Arg Arg Gln Pro Ile Pro Lys Ala Arg Arg Pro Glu
            100                 105                 110

Gly Arg Ser Trp Ala Gln Pro Gly Tyr Pro Trp Pro Leu Tyr Gly Asn
        115                 120                 125

Glu Gly Cys Gly Trp Ala Gly Trp Leu Leu Ser Pro Arg Gly Ser Arg
    130                 135                 140

Pro Ser Trp Gly Pro Thr Asp Pro Arg Arg Ser Arg Asn Leu Gly
145                 150                 155                 160

Lys Val Ile Asp Thr Leu Thr Cys Gly Phe Ala Asp Leu Met Gly Tyr
                165                 170                 175
```

```
Ile Pro Leu Val Gly Ala Pro Leu Gly Gly Ala Ala Arg Ala Leu Ala
            180                 185                 190

His Gly Val Arg Val Leu Glu Asp Gly Val Asn Tyr Ala Thr Gly Asn
        195                 200                 205

Leu Pro Gly Cys Ser Phe Ser Ile Phe Leu Leu Ala Leu Leu Ser Cys
    210                 215                 220

Leu Thr Val Pro Ala Ser Gly Gly Ser Gly Gly Val Asp Leu
225                 230                 235                 240

Leu Val Gly Ala Ala Thr Met Cys Ser Ala Leu Tyr Val Gly Asp Met
                245                 250                 255

Cys Gly Pro His Trp Gly Val Leu Ala Gly Leu Ala Tyr Tyr Ser Met
            260                 265                 270

Gln Gly Asn Trp Ala Lys Val Ser Val Cys Gly Pro Val Tyr Cys Phe
        275                 280                 285

Thr Pro Ser Pro Val Val Gly Thr Thr Asp Arg Gly Pro Gly Ser
    290                 295                 300

Gly Lys Gly Pro Gly Gly Arg Cys Gly Ser Gly Pro Trp Leu Thr Pro
305                 310                 315                 320

Arg Cys Leu Val Asp Tyr Pro Tyr Arg Leu Trp His Tyr Pro Cys Thr
                325                 330                 335

Ala Ala Cys Asn Trp Thr Arg Gly Glu Arg Cys Asp Ile Glu Asp Arg
            340                 345                 350

Asp Arg Ser Glu Leu Gly Gly Ser Gly Thr Thr Glu Leu Ala Ile Leu
        355                 360                 365

Pro Cys Ser Phe Thr Pro Leu Pro Ala Leu Ser Thr Gly Leu Ile His
    370                 375                 380

Leu His Gln Asn Ile Val Asp Val Gln Tyr Leu Tyr Gly Val Gly Ser
385                 390                 395                 400

Gly Met Met Gly Trp Arg Leu Leu Ala Pro Ile Thr Ala Tyr Ala Gln
                405                 410                 415

Gln Thr Arg Gly Leu Leu Gly Thr Ile Val Thr Ser Leu Thr Gly Arg
            420                 425                 430

Asp Lys Asn Val Val Thr Gly Glu Val Gln Val Leu Ser Thr Ala Gly
        435                 440                 445

Ser Gly Pro Cys Thr Cys Gly Ser Ala Asp Leu Tyr Leu Val Thr Arg
    450                 455                 460

Asp Ala Asp Val Ile Pro Ala Arg Arg Arg Gly Asp Ser Thr Ala Ser
465                 470                 475                 480

Leu Leu Ser Pro Arg Pro Leu Ala Cys Leu Lys Gly Ser Ser Gly Gly
                485                 490                 495

Pro Val Met Cys Pro Ser Gly His Val Ala Gly Ile Phe Arg Ala Ala
            500                 505                 510

Val Cys Thr Arg Gly Val Ala Lys Ala Leu Gln Phe Ile Pro Val Glu
        515                 520                 525

Thr Leu Arg Ser Pro Val Phe Ser Asp Asn Ser Pro Pro Ala Val
    530                 535                 540

Pro Gln Ser Tyr Gln Val Ala His Leu His Ala Pro Thr Gly Ser Gly
545                 550                 555                 560

Lys Ser Thr Lys Val Pro Ala Ala Tyr Ala Ala Gln Gly Tyr Lys Val
                565                 570                 575

Leu Val Leu Asn Pro Ser Val Ala Ala Thr Leu Gly Phe Gly Ala Tyr
            580                 585                 590

Met Ser Lys Ala Thr Gly Asn Arg Thr Ile Thr Thr Gly Ala Lys Leu
```

```
                   595                600                605
Thr Tyr Ser Thr Tyr Gly Lys Phe Leu Ala Asp Gly Gly Cys Ser Gly
    610                615                620
Gly Ala Tyr Asp Val Ile Ile Cys Asp Glu Cys His Ala Gln Asp Ala
625                630                635                640
Thr Ser Ile Leu Gly Ile Gly Thr Val Leu Asp Gln Ala Glu Thr Ala
                645                650                655
Gly Val Arg Leu Thr Val Leu Ala Thr Ala Thr Pro Pro Gly Ser Ile
            660                665                670
Thr Val Pro His Ser Asn Ile Glu Glu Val Ala Leu Ser Val Ile Pro
        675                680                685
Thr Ala Gly Asp Val Val Cys Ala Thr Asp Ala Leu Met Thr Gly
    690                695                700
Phe Thr Gly Asp Phe Asp Ser Val Ile Asp Cys Asn Val Ala Val Glu
705                710                715                720
Gln Tyr Val Asp Phe Ser Leu Asp Pro Thr Phe Ser Ile Glu Thr Arg
                725                730                735
Thr Ala Pro Gln Asp Ala Val Ser Arg Ser Gln Arg Gly Arg Thr
            740                745                750
Gly Arg Gly Arg Leu Gly Thr Tyr Arg Tyr Val Gly Pro Gly Glu Arg
        755                760                765
Pro Ser Gly Met Phe Asp Ser Val Val Leu Cys Glu Cys Tyr Asp Ala
    770                775                780
Gly Cys Ala Trp Tyr Glu Leu Gln Pro Ala Glu Thr Thr Val Arg Leu
785                790                795                800
Arg Ala Tyr Leu Ser Thr Pro Gly Leu Pro Val Cys Gln Asp His Leu
                805                810                815
Asp Phe Trp Glu Ser Val Phe Thr Gly Leu Thr His Ile Asp Ala His
            820                825                830
Phe Leu Ser Gln Thr Lys Gln Gln Gly Leu Asn Phe Pro Tyr Leu Thr
        835                840                845
Ala Tyr Gln Ala Thr Val Cys Ala Arg Ala Gln Ala Pro Pro Ser
    850                855                860
Trp Asp Glu Met Trp Lys Cys Leu Val Arg Leu Lys Pro Thr Leu His
865                870                875                880
Gly Pro Thr Pro Leu Leu Tyr Arg Leu Gly Pro Val Gln Asn Gly Pro
                885                890                895
Pro Met Ala Cys Met Ser Ala Asp Leu Glu Val Thr Thr Ser Thr Trp
            900                905                910
Val Leu Leu Gly Gly Val Leu Ala Ala Leu Ala Ala Tyr Cys Leu Ser
        915                920                925
Val Gly Cys Val Val Ile Val Gly His Phe Trp Ala Lys His Met Trp
    930                935                940
Asn Phe Ile Ser Gly Ile Gln Tyr Leu Ala Gly Leu Ser Thr Leu Pro
945                950                955                960
Gly Asn Pro Ala Ile Ala Ser Leu Met Ala Phe Thr Ala Gly Pro Ile
                965                970                975
Gly Ser Val Gly Leu Gly Lys Val Leu Val Asp Ile Leu Ala Gly Tyr
            980                985                990
Gly Ala Gly Val Ala Gly Ala Leu  Val Ala Phe Lys Ile  Met Ser Gly
        995                1000                1005
Glu Ile  Pro Ser Thr Glu Asp  Leu Val Asn Leu Leu  Pro Ala Ile
    1010                1015                1020
```

```
Leu Ser Pro Gly Ala Leu Val Gly Val Val Cys Ala Ala Ile
    1025                1030                1035

Leu Arg Arg His Val Gly Pro Gly Glu Gly Ala Val Gln Trp Met
    1040                1045                1050

Asn Arg Leu Ile Ala Phe Ala Ser Arg Gly Asn His Val Ser Pro
    1055                1060                1065

Thr His Tyr Val Pro Glu Ser Asp Ala Ala Arg Val Thr Ala
    1070                1075                1080

Ile Leu Ser Ser Leu Thr Cys Pro Cys Gln Val Pro Ala Pro Glu
    1085                1090                1095

Phe Phe Thr Glu Val Asp Gly Val Arg Leu His Arg Gly Gly Gly
    1100                1105                1110

Pro Pro Gly Gly Gly Ile Gly Ser Gln Leu Pro Cys Glu Pro Glu
    1115                1120                1125

Pro Asp Val Ser Val Leu Thr Ser Met Leu Pro Thr Ala Ala Arg
    1130                1135                1140

Arg Leu Ala Arg Gly Ser Pro Pro Ser Glu Ala Ser Ser Ser Ala
    1145                1150                1155

Ser Gln Leu Ser Ala Pro Ser Leu Lys Ala Thr Cys Gln Thr His
    1160                1165                1170

Arg Glu Ser Asp Ser Glu Ser Cys Ser Ser Met Pro Pro Leu Glu
    1175                1180                1185

Gly Glu Pro Gly Asp Pro Asp Leu Ser Cys Asp Ser Trp Ser Thr
    1190                1195                1200

Val Ser Asp Gln Ser Val Val Cys Cys Ser Met Ser Tyr Ser Trp
    1205                1210                1215

Thr Gly Ala Leu Ile Thr Pro Cys Ser Ala Glu Glu Lys Leu
    1220                1225                1230

Pro Ile Asn Pro Leu Ser Asn Ser Leu Leu Arg His His Asn Leu
    1235                1240                1245

Val Tyr Ser Thr Ser Ser Arg Ser Ala Ser Gln Arg Gln Lys Lys
    1250                1255                1260

Val Thr Phe Asp Arg Leu Gln Val Leu Asp Asp His Tyr Lys Gly
    1265                1270                1275

Pro Gly Pro Glu Lys Gly Gly Arg Lys Pro Ala Arg Leu Ile Val
    1280                1285                1290

Tyr Pro Asp Leu Gly Val Arg Val Cys Glu Lys Met Ala Leu Tyr
    1295                1300                1305

Asp Val Pro Gly Pro Gly Gly Trp Thr Ser Lys Lys Thr Pro
    1310                1315                1320

Met Gly Phe Ser Tyr Asp Thr Arg Cys Phe Asp Ser Thr Val Thr
    1325                1330                1335

Glu Gln Asp Ile Arg Val Glu Glu Gly Pro Cys Gly Tyr Arg
    1340                1345                1350

Arg Cys Arg Ala Ser Gly Val Leu Thr Thr Ser Cys Gly Asn Thr
    1355                1360                1365

Leu Thr Cys Tyr Ile Lys Ala Arg Ala Ala Cys Gly Gly Ser Gly
    1370                1375                1380

Gly Ala Leu Arg Ala Phe Thr Glu Ala Met Thr Arg Tyr Ser Ala
    1385                1390                1395

Pro Pro Gly Asp Ala Pro Gln Pro Gly Gly Lys Gly Lys Arg Tyr
    1400                1405                1410
```

```
Tyr Tyr Leu Thr Arg Asp Pro Thr Thr Pro Leu Ala Arg Ala Ala
    1415                1420                1425

Trp Glu Thr Ala Arg His Thr Pro Val Asn Ser Trp Leu Gly Asn
    1430                1435                1440

Ile Ile Met Tyr Ala Pro Thr Ile Trp Val Arg Met Val Met Gly
    1445                1450                1455

Lys Gly Pro Gly Ser Tyr Gly Ala Thr Tyr Ser Val Thr Pro Leu
    1460                1465                1470

Asp Leu Pro Ala Ile Ile Glu Arg Leu His Gly Leu Ser Ala Phe
    1475                1480                1485

Thr Leu His Ser Tyr Ser Pro Val Glu Leu Asn Arg Val Ala Gly
    1490                1495                1500

Thr Leu Arg Lys Leu Gly Cys Pro Pro Leu Arg Ala Trp Arg His
    1505                1510                1515

Arg Gly Gly Pro Gly Gly Pro Gly Gly Val Arg Ala Lys Leu Leu
    1520                1525                1530

Ser Gln Gly Gly Arg Ala Ala Ile Cys Gly Lys Tyr Leu Phe Asn
    1535                1540                1545

Trp Ala Val Arg Thr Lys
    1550

<210> SEQ ID NO 122
<211> LENGTH: 1115
<212> TYPE: PRT
<213> ORGANISM: Homo sapiens

<400> SEQUENCE: 122

Met Asp Ala Met Lys Arg Gly Leu Cys Cys Val Leu Leu Cys Gly
1               5                   10                  15

Ala Val Phe Val Ser Pro Ser Gln Glu Ile His Ala Arg Phe Arg Arg
                20                  25                  30

Lys Gly Gly Gly Pro Gly Gly Gly Thr Lys Arg Asn Thr Asn Arg Arg
                35                  40                  45

Pro Met Asp Val Lys Phe Pro Gly Gly Gln Ile Val Gly Gly Val
    50                  55                  60

Tyr Leu Leu Pro Arg Arg Gly Pro Arg Leu Gly Val Arg Ala Thr Arg
65                  70                  75                  80

Lys Thr Ser Glu Arg Ser Gln Pro Arg Gly Arg Arg Gln Pro Ile Pro
                85                  90                  95

Lys Ala Arg Arg Pro Glu Gly Arg Ser Trp Ala Gln Pro Gly Tyr Pro
                100                 105                 110

Trp Pro Leu Tyr Gly Asn Glu Gly Cys Gly Trp Ala Gly Trp Leu Leu
            115                 120                 125

Ser Pro Arg Gly Ser Arg Pro Ser Trp Gly Pro Asn Asp Pro Arg Arg
    130                 135                 140

Arg Ser Arg Asn Leu Gly Lys Val Ile Asp Thr Leu Thr Cys Gly Phe
145                 150                 155                 160

Ala Asp Leu Met Gly Tyr Ile Pro Leu Val Gly Ala Pro Val Gly Gly
                165                 170                 175

Val Ala Arg Ala Leu Ala His Gly Val Arg Ala Leu Glu Asp Gly Ile
                180                 185                 190

Asn Tyr Ala Thr Gly Asn Leu Pro Gly Cys Ser Phe Ser Ile Phe Leu
            195                 200                 205

Leu Ala Leu Leu Ser Cys Leu Thr Val Pro Ala Ser Cys Pro Thr Asp
    210                 215                 220
```

-continued

```
Cys Phe Arg Lys His Pro Glu Ala Thr Tyr Thr Lys Cys Gly Ser Gly
225                 230                 235                 240
Pro Trp Leu Thr Pro Arg Cys Leu Val Asp Tyr Pro Tyr Arg Leu Trp
            245                 250                 255
His Tyr Pro Cys Thr Val Asn Phe Gly Ser Gly Leu Leu Leu Ser Thr
                260                 265                 270
Thr Glu Trp Gln Ile Leu Pro Cys Ser Phe Thr Thr Leu Pro Ala Leu
            275                 280                 285
Ser Thr Gly Leu Ile His Leu His Gln Asn Ile Val Asp Val Gln Tyr
        290                 295                 300
Leu Tyr Gly Val Gly Ser Gly Pro Pro Cys Thr Cys Gly Ser Ser Asp
305                 310                 315                 320
Leu Tyr Leu Val Thr Arg His Ala Asp Val Ile Pro Val Arg Arg Arg
                325                 330                 335
Gly Asp Ser Arg Gly Ser Leu Leu Ser Pro Arg Pro Ile Ser Tyr Leu
            340                 345                 350
Lys Gly Ser Ser Gly Gly Pro Val Leu Cys Pro Ser Gly His Ala Val
            355                 360                 365
Gly Ile Phe Arg Ala Ala Val Cys Thr Arg Gly Val Ala Lys Ala Val
370                 375                 380
Asp Phe Ile Pro Val Glu Ser Leu Glu Met Arg Ser Pro Val Phe Thr
385                 390                 395                 400
Asp Asn Ser Thr Pro Pro Ala Val Pro Gln Thr Tyr Gln Val Ala His
                405                 410                 415
Leu His Ala Pro Thr Gly Ser Gly Lys Ser Thr Lys Val Pro Ala Ala
            420                 425                 430
Tyr Ala Ala Gln Gly Tyr Lys Val Leu Val Leu Asn Pro Ser Val Ala
        435                 440                 445
Ala Thr Leu Gly Phe Gly Ala Tyr Met Ser Lys Ala Tyr Gly Ile Gly
    450                 455                 460
Gly Ser Arg Ser Gly Val Arg Thr Ile Thr Thr Gly Ala Pro Ile Thr
465                 470                 475                 480
Tyr Ser Thr Tyr Gly Lys Phe Leu Ala Asp Gly Gly Cys Ser Gly Gly
                485                 490                 495
Ala Tyr Asp Ile Ile Cys Asp Glu Cys His Ser Thr Asp Ser Thr
            500                 505                 510
Thr Ile Leu Gly Ile Gly Thr Val Leu Asp Gln Ala Glu Thr Ala Gly
        515                 520                 525
Val Arg Leu Val Val Leu Ala Thr Ala Thr Pro Pro Gly Gly Asn Ala
530                 535                 540
Val Ala Tyr Tyr Arg Gly Leu Asp Val Ser Val Ile Pro Thr Ser Gly
545                 550                 555                 560
Asp Val Val Val Ala Thr Asp Ala Leu Met Thr Gly Phe Thr Gly
                565                 570                 575
Asp Phe Asp Ser Val Ile Asp Cys Asn Thr Cys Val Thr Gln Thr Val
            580                 585                 590
Asp Phe Ser Leu Asp Pro Thr Phe Thr Ile Glu Thr Thr Thr Val Pro
        595                 600                 605
Gln Asp Ala Val Ser Arg Ser Gln Arg Arg Gly Arg Thr Gly Arg Gly
    610                 615                 620
Arg Arg Gly Ile Tyr Arg Phe Val Thr Pro Gly Glu Arg Pro Ser Gly
625                 630                 635                 640
```

```
Met Phe Asp Ser Ser Val Leu Cys Glu Cys Tyr Asp Ala Gly Cys Ala
                645                 650                 655

Trp Tyr Glu Leu Thr Pro Ala Glu Thr Ser Val Arg Leu Arg Ala Tyr
        660                 665                 670

Leu Asn Thr Pro Gly Leu Pro Val Cys Gln Asp His Leu Glu Phe Trp
            675                 680                 685

Glu Gly Val Phe Thr Gly Leu Thr His Ile Asp Ala His Phe Leu Ser
690                 695                 700

Gln Thr Lys Gln Ala Gly Asp Asn Phe Pro Tyr Leu Val Ala Tyr Gln
705                 710                 715                 720

Ala Thr Val Cys Ala Arg Ala Gln Ala Pro Pro Ser Trp Asp Gln
                725                 730                 735

Met Trp Thr His Pro Ile Thr Lys Tyr Ile Met Ala Cys Met Ser Ala
                740                 745                 750

Asp Leu Glu Val Val Thr Ser Thr Trp Val Leu Val Gly Gly Val Leu
                755                 760                 765

Ala Ala Leu Ala Ala Tyr Cys Leu Ser Val Gly Ser Val Val Ile Val
                770                 775                 780

Gly Gly Pro Gly Phe Trp Ala Lys His Met Trp Asn Phe Ile Ser Gly
785                 790                 795                 800

Ile Gln Tyr Leu Ala Gly Leu Ser Thr Leu Pro Gly Asn Pro Ala Ile
                805                 810                 815

Ala Ser Leu Met Ala Phe Thr Ala Ala Val Thr Ser Pro Leu Gly Ala
                820                 825                 830

Ala Val Gly Ser Val Gly Leu Gly Lys Val Leu Val Asp Ile Leu Ala
                835                 840                 845

Gly Tyr Gly Ala Gly Val Ala Gly Ala Leu Val Ala Phe Lys Ile Met
        850                 855                 860

Ser Gly Glu Val Pro Ser Thr Glu Asp Leu Val Asn Leu Leu Pro Ala
865                 870                 875                 880

Ile Leu Ser Pro Gly Ala Leu Val Val Gly Val Val Cys Ala Ala Ile
                885                 890                 895

Leu Arg Arg His Val Gly Pro Gly Glu Gly Ala Val Gln Trp Met Asn
                900                 905                 910

Arg Leu Ile Ala Phe Ala Ser Arg Gly Asn His Val Ser Pro Thr His
        915                 920                 925

Tyr Val Pro Glu Ser Asp Ala Ala Ala Arg Val Gly Gly Gly Ser Gly
        930                 935                 940

Gly Gly Val Cys Cys Ser Met Ser Tyr Ser Trp Thr Gly Ala Leu Ile
945                 950                 955                 960

Thr Pro Cys Ala Ala Glu Glu Glu Lys Leu Pro Ile Asn Pro Leu Ser
                965                 970                 975

Asn Ser Leu Ile Arg His His Asn Met Val Tyr Ser Thr Thr Ser Arg
                980                 985                 990

Ser Ala Ser Leu Arg Gln Lys Lys Val Thr Phe Asp Arg Gly Gly Gly
            995                1000                1005

Lys Gly Gly Gly Pro Thr Pro Leu Ala Arg Ala Ala Trp Glu Thr
        1010                1015                1020

Ala Arg His Thr Pro Val Asn Ser Trp Leu Gly Asn Ile Ile Met
        1025                1030                1035

Tyr Ala Pro Thr Ile Trp Val Arg Met Val Leu Met Thr His Phe
        1040                1045                1050

Phe Ser Ile Leu Gln Gly Gly Gly Ser Gly Gly Pro Glu Leu Asn
```

```
                1055                1060                1065

Arg Val Gly Ala Cys Leu Arg Lys Leu Gly Val Pro Pro Leu Arg
            1070                1075                1080

Ala Trp Arg His Arg Ala Arg Ala Val Arg Ala Lys Leu Ile Ala
            1085                1090                1095

Gln Gly Gly Lys Ala Ala Ile Cys Gly Lys Tyr Leu Phe Asn Trp
            1100                1105                1110

Ala Val
    1115

<210> SEQ ID NO 123
<211> LENGTH: 1453
<212> TYPE: PRT
<213> ORGANISM: Homo sapiens

<400> SEQUENCE: 123

Met Asp Ala Met Lys Arg Gly Leu Cys Cys Val Leu Leu Cys Gly
1               5                   10                  15

Ala Val Phe Val Ser Pro Ser Gln Glu Ile His Ala Arg Phe Arg Arg
                20                  25                  30

Lys Gly Gly Gly Pro Gly Gly Gly Thr Lys Arg Asn Thr Asn Arg Arg
            35                  40                  45

Pro Met Asp Val Lys Phe Pro Gly Gly Gly Gln Ile Val Gly Gly Val
    50                  55                  60

Tyr Leu Leu Pro Arg Arg Gly Pro Arg Leu Gly Val Arg Ala Thr Arg
65                  70                  75                  80

Lys Thr Ser Glu Arg Ser Gln Pro Arg Gly Arg Arg Gln Pro Ile Pro
                85                  90                  95

Lys Ala Arg Arg Pro Glu Gly Arg Ser Trp Ala Gln Pro Gly Tyr Pro
            100                 105                 110

Trp Pro Leu Tyr Gly Asn Glu Gly Cys Gly Trp Ala Gly Trp Leu Leu
        115                 120                 125

Ser Pro Arg Gly Ser Arg Pro Ser Trp Gly Pro Asn Asp Pro Arg Arg
    130                 135                 140

Arg Ser Arg Asn Leu Gly Lys Val Ile Asp Thr Leu Thr Cys Gly Phe
145                 150                 155                 160

Ala Asp Leu Met Gly Tyr Ile Pro Leu Val Gly Ala Pro Val Gly Gly
                165                 170                 175

Val Ala Arg Ala Leu Ala His Gly Val Arg Ala Leu Glu Asp Gly Ile
            180                 185                 190

Asn Tyr Ala Thr Gly Asn Leu Pro Gly Cys Ser Phe Ser Ile Phe Leu
        195                 200                 205

Leu Ala Leu Leu Ser Cys Leu Thr Val Pro Ala Ser Pro Gly Cys Asn
    210                 215                 220

Cys Ser Ile Tyr Pro Gly His Ile Thr Gly His Arg Met Ala Trp Asp
225                 230                 235                 240

Met Met Met Asn Trp Ser Pro Thr Thr Lys Lys Asn Gly Ser Trp His
                245                 250                 255

Ile Asn Arg Thr Ala Leu Asn Cys Asn Asp Ser Leu Asn Thr Gly Phe
            260                 265                 270

Ile Gly Pro Gly Gly Ser Val Cys Gly Pro Val Tyr Cys Phe Thr Pro
        275                 280                 285

Ser Pro Val Val Val Gly Thr Thr Asp Arg Gly Pro Gly Cys Pro Thr
    290                 295                 300
```

```
Asp Cys Phe Arg Lys His Pro Glu Ala Thr Tyr Thr Lys Cys Gly Ser
305                 310                 315                 320

Gly Pro Trp Leu Thr Pro Arg Cys Leu Val Asp Tyr Pro Tyr Arg Leu
                325                 330                 335

Trp His Tyr Pro Cys Thr Val Asn Phe Gly Ser Gly Leu Leu Leu Ser
                340                 345                 350

Thr Thr Glu Trp Gln Ile Leu Pro Cys Ser Phe Thr Thr Leu Pro Ala
                355                 360                 365

Leu Ser Thr Gly Leu Ile His Leu His Gln Asn Ile Val Asp Val Gln
                370                 375                 380

Tyr Leu Tyr Gly Val Gly Ser Met Gly Trp Arg Leu Leu Ala Pro Ile
385                 390                 395                 400

Thr Ala Tyr Ala Gln Gln Thr Arg Gly Leu Leu Gly Thr Ile Val Thr
                405                 410                 415

Ser Leu Thr Gly Arg Asp Lys Asn Pro Cys Thr Cys Gly Ser Ser Asp
                420                 425                 430

Leu Tyr Leu Val Thr Arg His Ala Asp Val Ile Pro Val Arg Arg Arg
                435                 440                 445

Gly Asp Ser Arg Gly Ser Leu Leu Ser Pro Arg Pro Ile Ser Tyr Leu
450                 455                 460

Lys Gly Ser Ser Gly Gly Pro Val Leu Cys Pro Ser Gly His Ala Val
465                 470                 475                 480

Gly Ile Phe Arg Ala Ala Val Cys Thr Arg Gly Val Ala Lys Ala Val
                485                 490                 495

Asp Phe Ile Pro Val Glu Ser Leu Glu Met Arg Ser Pro Val Phe Thr
                500                 505                 510

Asp Asn Ser Thr Pro Pro Ala Val Pro Gln Thr Tyr Gln Val Ala His
                515                 520                 525

Leu His Ala Pro Thr Gly Ser Gly Lys Ser Thr Lys Val Pro Ala Ala
                530                 535                 540

Tyr Ala Ala Gln Gly Tyr Lys Val Leu Val Leu Asn Pro Ser Val Ala
545                 550                 555                 560

Ala Thr Leu Gly Phe Gly Ala Tyr Met Ser Lys Ala Tyr Gly Ile Gly
                565                 570                 575

Gly Ser Arg Ser Gly Val Arg Thr Ile Thr Thr Gly Ala Pro Ile Thr
                580                 585                 590

Tyr Ser Thr Tyr Gly Lys Phe Leu Ala Asp Gly Gly Cys Ser Gly Gly
                595                 600                 605

Ala Tyr Asp Ile Ile Ile Cys Asp Glu Cys His Ser Thr Asp Ser Thr
610                 615                 620

Thr Ile Leu Gly Ile Gly Thr Val Leu Asp Gln Ala Glu Thr Ala Gly
625                 630                 635                 640

Val Arg Leu Val Val Leu Ala Thr Ala Thr Pro Pro Gly Gly Lys Gly
                645                 650                 655

Gly Lys Gly Ile Lys Gly Arg His Leu Ile Phe Cys His Ser Lys
                660                 665                 670

Lys Lys Cys Asp Glu Leu Ala Gly Pro Gly Asn Ala Val Ala Tyr Tyr
                675                 680                 685

Arg Gly Leu Asp Val Ser Val Ile Pro Thr Ser Gly Asp Val Val Val
                690                 695                 700

Val Ala Thr Asp Ala Leu Met Thr Gly Phe Thr Gly Asp Phe Asp Ser
705                 710                 715                 720

Val Ile Asp Cys Asn Thr Cys Val Thr Gln Thr Val Asp Phe Ser Leu
```

-continued

```
                725                 730                 735
Asp Pro Thr Phe Thr Ile Glu Thr Thr Thr Val Pro Gln Asp Ala Val
                740                 745                 750
Ser Arg Ser Gln Arg Arg Gly Arg Thr Gly Arg Gly Arg Gly Arg Gly Ile
                755                 760                 765
Tyr Arg Phe Val Thr Pro Gly Glu Arg Pro Ser Gly Met Phe Asp Ser
                770                 775                 780
Ser Val Leu Cys Glu Cys Tyr Asp Ala Gly Cys Ala Trp Tyr Glu Leu
785                 790                 795                 800
Thr Pro Ala Glu Thr Ser Val Arg Leu Arg Ala Tyr Leu Asn Thr Pro
                805                 810                 815
Gly Leu Pro Val Cys Gln Asp His Leu Glu Phe Trp Glu Gly Val Phe
                820                 825                 830
Thr Gly Leu Thr His Ile Asp Ala His Phe Leu Ser Gln Thr Lys Gln
                835                 840                 845
Ala Gly Asp Asn Phe Pro Tyr Leu Val Ala Tyr Gln Ala Thr Val Cys
                850                 855                 860
Ala Arg Ala Gln Ala Pro Pro Pro Ser Trp Asp Gln Met Trp Thr His
865                 870                 875                 880
Pro Ile Thr Lys Tyr Ile Met Ala Cys Met Ser Ala Asp Leu Glu Val
                                    885                 890                 895
Val Thr Ser Thr Trp Val Leu Val Gly Gly Val Leu Ala Ala Leu Ala
                900                 905                 910
Ala Tyr Cys Leu Ser Val Gly Ser Val Val Ile Val Gly Gly Pro Gly
                915                 920                 925
Phe Trp Ala Lys His Met Trp Asn Phe Ile Ser Gly Ile Gln Tyr Leu
                930                 935                 940
Ala Gly Leu Ser Thr Leu Pro Gly Asn Pro Ala Ile Ala Ser Leu Met
945                 950                 955                 960
Ala Phe Thr Ala Ala Val Thr Ser Pro Leu Gly Ala Ala Val Gly Ser
                965                 970                 975
Val Gly Leu Gly Lys Val Leu Val Asp Ile Leu Ala Gly Tyr Gly Ala
                980                 985                 990
Gly Val Ala Gly Ala Leu Val Ala  Phe Lys Ile Met Ser  Gly Glu Val
                995                 1000                1005
Pro Ser Thr Glu Asp Leu Val  Asn Leu Leu Pro Ala  Ile Leu Ser
        1010                1015                1020
Pro Gly Ala Leu Val Val Gly  Val Val Cys Ala Ala  Ile Leu Arg
        1025                1030                1035
Arg His Val Gly Pro Gly Glu  Gly Ala Val Gln Trp  Met Asn Arg
        1040                1045                1050
Leu Ile Ala Phe Ala Ser Arg  Gly Asn His Val Ser  Pro Thr His
        1055                1060                1065
Tyr Val Pro Glu Ser Asp Ala  Ala Ala Arg Val Gly  Pro Thr Ala
        1070                1075                1080
Glu Thr Ala Ala Arg Arg Leu  Ala Arg Gly Ser Pro  Pro Ser Leu
        1085                1090                1095
Ala Ser Ser Ser Ala Ser Gln  Leu Ser Ala Pro Ser  Leu Lys Ala
        1100                1105                1110
Thr Cys Thr Val Cys Cys Ser  Met Ser Tyr Ser Trp  Thr Gly Ala
        1115                1120                1125
Leu Ile Thr Pro Cys Ala Ala  Glu Glu Glu Lys Leu  Pro Ile Asn
        1130                1135                1140
```

Pro Leu Ser Asn Ser Leu Ile Arg His His Asn Met Val Tyr Ser
     1145                1150                1155

Thr Thr Ser Arg Ser Ala Ser Leu Arg Gln Lys Lys Val Thr Phe
     1160                1165                1170

Asp Arg Gly Gly Ser Gly Gly Pro Gly Pro Ser Lys Gly Gly Arg
     1175                1180                1185

Lys Pro Ala Arg Leu Ile Val Tyr Pro Asp Leu Gly Val Arg Val
     1190                1195                1200

Cys Glu Lys Arg Ala Leu Tyr Asp Val Pro Gly Gly Pro Lys Lys
     1205                1210                1215

Thr Pro Met Gly Phe Ser Tyr Asp Thr Arg Cys Phe Asp Ser Thr
     1220                1225                1230

Val Thr Glu Arg Asp Ile Arg Thr Glu Gly Gly Gly Pro Gly Gly
     1235                1240                1245

Cys Gly Tyr Arg Arg Cys Arg Ala Ser Gly Val Leu Thr Thr Ser
     1250                1255                1260

Met Gly Asn Thr Ile Thr Cys Tyr Ile Lys Ala Leu Ala Ala Glu
     1265                1270                1275

Ala Met Thr Arg Tyr Ser Ala Pro Pro Gly Asp Pro Pro Gln Pro
     1280                1285                1290

Glu Tyr Asp Leu Glu Leu Ile Thr Ser Cys Ser Ser Asn Val Ser
     1295                1300                1305

Val Ala His Asp Gly Gly Ser Gly Gly Thr Pro Leu Ala Arg Ala
     1310                1315                1320

Ala Trp Glu Thr Ala Arg His Thr Pro Val Asn Ser Trp Leu Gly
     1325                1330                1335

Asn Ile Ile Met Tyr Ala Pro Thr Ile Trp Val Arg Met Val Leu
     1340                1345                1350

Met Thr His Phe Phe Ser Ile Leu Gln Gly Gly Pro Gly Tyr Gly
     1355                1360                1365

Ala Thr Tyr Ser Val Thr Pro Leu Asp Leu Pro Ala Ile Ile Glu
     1370                1375                1380

Arg Leu His Gly Leu Ser Ala Phe Thr Leu His Ser Tyr Ser Gly
     1385                1390                1395

Gly Pro Gly Gly Pro Glu Leu Asn Arg Val Gly Ala Cys Leu Arg
     1400                1405                1410

Lys Leu Gly Val Pro Pro Leu Arg Ala Trp Arg His Arg Ala Arg
     1415                1420                1425

Ala Val Arg Ala Lys Leu Ile Ala Gln Gly Gly Lys Ala Ala Ile
     1430                1435                1440

Cys Gly Lys Tyr Leu Phe Asn Trp Ala Val
     1445                1450

<210> SEQ ID NO 124
<211> LENGTH: 1390
<212> TYPE: PRT
<213> ORGANISM: Homo sapiens

<400> SEQUENCE: 124

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Lys Gly Gly Gly Pro Gly Gly Gly Thr Lys Arg Asn Thr Asn Arg Arg

-continued

```
                35                  40                  45
Pro Met Asp Val Lys Phe Pro Gly Gly Gln Ile Val Gly Gly Val
        50                  55                  60
Tyr Leu Leu Pro Arg Arg Gly Pro Arg Leu Gly Val Arg Ala Thr Arg
65                  70                  75                  80
Lys Thr Ser Glu Arg Ser Gln Pro Arg Gly Arg Arg Gln Pro Ile Pro
                85                  90                  95
Lys Ala Arg Arg Pro Glu Gly Arg Ser Trp Ala Gln Pro Gly Tyr Pro
            100                 105                 110
Trp Pro Leu Tyr Gly Asn Glu Gly Cys Gly Trp Ala Gly Trp Leu Leu
            115                 120                 125
Ser Pro Arg Gly Ser Arg Pro Ser Trp Gly Pro Asn Asp Pro Arg Arg
            130                 135                 140
Arg Ser Arg Asn Leu Gly Lys Val Ile Asp Thr Leu Thr Cys Gly Phe
145                 150                 155                 160
Ala Asp Leu Met Gly Tyr Ile Pro Leu Val Gly Ala Pro Val Gly Gly
                165                 170                 175
Val Ala Arg Ala Leu Ala His Gly Val Arg Ala Leu Glu Asp Gly Ile
            180                 185                 190
Asn Tyr Ala Thr Gly Asn Leu Pro Gly Cys Ser Phe Ser Ile Phe Leu
            195                 200                 205
Leu Ala Leu Leu Ser Cys Leu Thr Val Pro Ala Ser Cys Asn Cys Ser
            210                 215                 220
Ile Tyr Pro Gly His Ile Thr Gly His Arg Met Ala Trp Asp Met Met
225                 230                 235                 240
Met Asn Trp Ser Pro Thr Thr Asn Gly Ser Trp His Ile Asn Arg Thr
                245                 250                 255
Ala Leu Asn Cys Asn Asp Ser Leu Asn Thr Gly Phe Ile Ser Val Cys
            260                 265                 270
Gly Pro Val Tyr Cys Phe Thr Pro Ser Pro Val Val Gly Thr Thr
            275                 280                 285
Asp Arg Cys Pro Thr Asp Cys Phe Arg Lys His Pro Glu Ala Thr Tyr
        290                 295                 300
Thr Lys Cys Gly Ser Gly Pro Trp Leu Thr Pro Arg Cys Leu Val Asp
305                 310                 315                 320
Tyr Pro Tyr Arg Leu Trp His Tyr Pro Cys Thr Val Asn Phe Leu Leu
                325                 330                 335
Leu Ser Thr Thr Glu Trp Gln Ile Leu Pro Cys Ser Phe Thr Thr Leu
            340                 345                 350
Pro Ala Leu Ser Thr Gly Leu Ile His Leu His Gln Asn Ile Val Asp
            355                 360                 365
Val Gln Tyr Leu Tyr Gly Val Gly Ser Met Gly Trp Arg Leu Leu Ala
        370                 375                 380
Pro Ile Thr Ala Tyr Ala Gln Gln Thr Arg Gly Leu Leu Gly Thr Ile
385                 390                 395                 400
Val Thr Ser Leu Thr Gly Arg Asp Lys Asn Pro Cys Thr Cys Gly Ser
                405                 410                 415
Ser Asp Leu Tyr Leu Val Thr Arg His Ala Asp Val Ile Pro Val Arg
            420                 425                 430
Arg Arg Gly Asp Ser Arg Gly Ser Leu Leu Ser Pro Arg Pro Ile Ser
            435                 440                 445
Tyr Leu Lys Gly Ser Ser Gly Gly Pro Val Leu Cys Pro Ser Gly His
            450                 455                 460
```

```
Ala Val Gly Ile Phe Arg Ala Val Cys Thr Arg Val Ala Lys
465                 470                 475                 480

Ala Val Asp Phe Ile Pro Val Glu Ser Leu Glu Met Arg Ser Pro Val
                485                 490                 495

Phe Thr Asp Asn Ser Thr Pro Pro Ala Val Pro Gln Thr Tyr Gln Val
            500                 505                 510

Ala His Leu His Ala Pro Thr Gly Ser Gly Lys Ser Thr Lys Val Pro
        515                 520                 525

Ala Ala Tyr Ala Ala Gln Gly Tyr Lys Val Leu Val Leu Asn Pro Ser
    530                 535                 540

Val Ala Ala Thr Leu Gly Phe Gly Ala Tyr Met Ser Lys Ala Tyr Gly
545                 550                 555                 560

Ile Arg Ser Gly Val Arg Thr Ile Thr Thr Gly Ala Pro Ile Thr Tyr
                565                 570                 575

Ser Thr Tyr Gly Lys Phe Leu Ala Asp Gly Gly Cys Ser Gly Gly Ala
            580                 585                 590

Tyr Asp Ile Ile Ile Cys Asp Glu Cys His Ser Thr Asp Ser Thr Thr
        595                 600                 605

Ile Leu Gly Ile Gly Thr Val Leu Asp Gln Ala Glu Thr Ala Gly Val
    610                 615                 620

Arg Leu Val Val Leu Ala Thr Ala Thr Pro Pro Gly Ile Lys Gly Gly
625                 630                 635                 640

Arg His Leu Ile Phe Cys His Ser Lys Lys Lys Cys Asp Glu Leu Ala
                645                 650                 655

Asn Ala Val Ala Tyr Tyr Arg Gly Leu Asp Val Ser Val Ile Pro Thr
            660                 665                 670

Ser Gly Asp Val Val Val Ala Thr Asp Ala Leu Met Thr Gly Phe
        675                 680                 685

Thr Gly Asp Phe Asp Ser Val Ile Asp Cys Asn Thr Cys Val Thr Gln
        690                 695                 700

Thr Val Asp Phe Ser Leu Asp Pro Thr Phe Thr Ile Glu Thr Thr Thr
705                 710                 715                 720

Val Pro Gln Asp Ala Val Ser Arg Ser Gln Arg Arg Gly Arg Thr Gly
            725                 730                 735

Arg Gly Arg Arg Gly Ile Tyr Arg Phe Val Thr Pro Gly Glu Arg Pro
            740                 745                 750

Ser Gly Met Phe Asp Ser Ser Val Leu Cys Glu Cys Tyr Asp Ala Gly
            755                 760                 765

Cys Ala Trp Tyr Glu Leu Thr Pro Ala Glu Thr Ser Val Arg Leu Arg
        770                 775                 780

Ala Tyr Leu Asn Thr Pro Gly Leu Pro Val Cys Gln Asp His Leu Glu
785                 790                 795                 800

Phe Trp Glu Gly Val Phe Thr Gly Leu Thr His Ile Asp Ala His Phe
                805                 810                 815

Leu Ser Gln Thr Lys Gln Ala Gly Asp Asn Phe Pro Tyr Leu Val Ala
            820                 825                 830

Tyr Gln Ala Thr Val Cys Ala Arg Ala Gln Ala Pro Pro Pro Ser Trp
        835                 840                 845

Asp Gln Met Trp Thr His Pro Ile Thr Lys Tyr Ile Met Ala Cys Met
        850                 855                 860

Ser Ala Asp Leu Glu Val Val Thr Ser Thr Trp Val Leu Val Gly Gly
865                 870                 875                 880
```

```
Val Leu Ala Ala Leu Ala Ala Tyr Cys Leu Ser Val Gly Ser Val Val
            885                 890                 895
Ile Val Gly Phe Trp Ala Lys His Met Trp Asn Phe Ile Ser Gly Ile
        900                 905                 910
Gln Tyr Leu Ala Gly Leu Ser Thr Leu Pro Gly Asn Pro Ala Ile Ala
        915                 920                 925
Ser Leu Met Ala Phe Thr Ala Ala Val Thr Ser Pro Leu Gly Ala Ala
    930                 935                 940
Val Gly Ser Val Gly Leu Gly Lys Val Leu Val Asp Ile Leu Ala Gly
945                 950                 955                 960
Tyr Gly Ala Gly Val Ala Gly Ala Leu Val Ala Phe Lys Ile Met Ser
                965                 970                 975
Gly Glu Val Pro Ser Thr Glu Asp Leu Val Asn Leu Leu Pro Ala Ile
            980                 985                 990
Leu Ser Pro Gly Ala Leu Val Val  Gly Val Val Cys Ala  Ala Ile Leu
        995                 1000                1005
Arg Arg  His Val Gly Pro Gly  Glu Gly Ala Val Gln  Trp Met Asn
    1010                1015                1020
Arg Leu  Ile Ala Phe Ala Ser  Arg Gly Asn His Val  Ser Pro Thr
    1025                1030                1035
His Tyr  Val Pro Glu Ser Asp  Ala Ala Ala Arg Val  Thr Ala Glu
    1040                1045                1050
Thr Ala  Ala Arg Arg Leu Ala  Arg Gly Ser Pro Pro  Ser Leu Ala
    1055                1060                1065
Ser Ser  Ser Ala Ser Gln Leu  Ser Ala Pro Ser Leu  Lys Ala Thr
    1070                1075                1080
Cys Thr  Val Cys Cys Ser Met  Ser Tyr Ser Trp Thr  Gly Ala Leu
    1085                1090                1095
Ile Thr  Pro Cys Ala Ala Glu  Glu Lys Leu Pro  Ile Asn Pro
    1100                1105                1110
Leu Ser  Asn Ser Leu Ile Arg  His His Asn Met Val  Tyr Ser Thr
    1115                1120                1125
Thr Ser  Arg Ser Ala Ser Leu  Arg Gln Lys Lys Val  Thr Phe Asp
    1130                1135                1140
Arg Pro  Ser Lys Gly Gly Arg  Lys Pro Ala Arg Leu  Ile Val Tyr
    1145                1150                1155
Pro Asp  Leu Gly Val Arg Val  Cys Glu Lys Arg Ala  Leu Tyr Asp
    1160                1165                1170
Val Lys  Lys Thr Pro Met Gly  Phe Ser Tyr Asp Thr  Arg Cys Phe
    1175                1180                1185
Asp Ser  Thr Val Thr Glu Arg  Asp Ile Arg Thr Glu  Cys Gly Tyr
    1190                1195                1200
Arg Arg  Cys Arg Ala Ser Gly  Val Leu Thr Thr Ser  Met Gly Asn
    1205                1210                1215
Thr Ile  Thr Cys Tyr Ile Lys  Ala Leu Ala Ala Glu  Ala Met Thr
    1220                1225                1230
Arg Tyr  Ser Ala Pro Pro Gly  Asp Pro Pro Gln Pro  Glu Tyr Asp
    1235                1240                1245
Leu Glu  Leu Ile Thr Ser Cys  Ser Ser Asn Val Ser  Val Ala His
    1250                1255                1260
Asp Thr  Pro Leu Ala Arg Ala  Ala Trp Glu Thr Ala  Arg His Thr
    1265                1270                1275
Pro Val  Asn Ser Trp Leu Gly  Asn Ile Ile Met Tyr  Ala Pro Thr
```

```
              1280                1285                1290
Ile Trp Val Arg Met Val Leu Met Thr His Phe Phe Ser Ile Leu
      1295                1300                1305
Gln Tyr Gly Ala Thr Tyr Ser Val Thr Pro Leu Asp Leu Pro Ala
      1310                1315                1320
Ile Ile Glu Arg Leu His Gly Leu Ser Ala Phe Thr Leu His Ser
      1325                1330                1335
Tyr Ser Glu Leu Asn Arg Val Gly Ala Cys Leu Arg Lys Leu Gly
      1340                1345                1350
Val Pro Pro Leu Arg Ala Trp Arg His Arg Ala Arg Ala Val Arg
      1355                1360                1365
Ala Lys Leu Ile Ala Gln Gly Gly Lys Ala Ala Ile Cys Gly Lys
      1370                1375                1380
Tyr Leu Phe Asn Trp Ala Val
      1385                1390

<210> SEQ ID NO 125
<211> LENGTH: 1414
<212> TYPE: PRT
<213> ORGANISM: Homo sapiens

<400> SEQUENCE: 125

Met Thr Lys Arg Asn Thr Asn Arg Arg Pro Met Asp Val Lys Phe Pro
1               5                   10                  15

Gly Gly Gly Gln Ile Val Gly Val Tyr Leu Leu Pro Arg Arg Gly
                20                  25                  30

Pro Arg Leu Gly Val Arg Ala Thr Arg Lys Thr Ser Glu Arg Ser Gln
            35                  40                  45

Pro Arg Gly Arg Arg Gln Pro Ile Pro Lys Ala Arg Arg Pro Glu Gly
        50                  55                  60

Arg Ser Trp Ala Gln Pro Gly Tyr Pro Trp Pro Leu Tyr Gly Asn Glu
65                  70                  75                  80

Gly Cys Gly Trp Ala Gly Trp Leu Leu Ser Pro Arg Gly Ser Arg Pro
                85                  90                  95

Ser Trp Gly Pro Asn Asp Pro Arg Arg Ser Arg Asn Leu Gly Lys
                100                 105                 110

Val Ile Asp Thr Leu Thr Cys Gly Phe Ala Asp Leu Met Gly Tyr Ile
            115                 120                 125

Pro Leu Val Gly Ala Pro Val Gly Gly Val Ala Arg Ala Leu Ala His
        130                 135                 140

Gly Val Arg Ala Leu Glu Asp Gly Ile Asn Tyr Ala Thr Gly Asn Leu
145                 150                 155                 160

Pro Gly Cys Ser Phe Ser Ile Phe Leu Leu Ala Leu Leu Ser Cys Leu
                165                 170                 175

Thr Val Pro Ala Ser Pro Gly Cys Asn Cys Ser Ile Tyr Pro Gly His
            180                 185                 190

Ile Thr Gly His Arg Met Ala Trp Asp Met Met Met Asn Trp Ser Pro
        195                 200                 205

Thr Thr Lys Lys Asn Gly Ser Trp His Ile Asn Arg Thr Ala Leu Asn
        210                 215                 220

Cys Asn Asp Ser Leu Asn Thr Gly Phe Ile Gly Pro Gly Ser Val
225                 230                 235                 240

Cys Gly Pro Val Tyr Cys Phe Thr Pro Ser Pro Val Val Val Gly Thr
                245                 250                 255
```

```
Thr Asp Arg Gly Pro Gly Cys Pro Thr Asp Cys Phe Arg Lys His Pro
            260                 265                 270

Glu Ala Thr Tyr Thr Lys Cys Gly Ser Gly Pro Trp Leu Thr Pro Arg
            275                 280                 285

Cys Leu Val Asp Tyr Pro Tyr Arg Leu Trp His Tyr Pro Cys Thr Val
            290                 295                 300

Asn Phe Gly Ser Gly Leu Leu Leu Ser Thr Thr Glu Trp Gln Ile Leu
305                 310                 315                 320

Pro Cys Ser Phe Thr Thr Leu Pro Ala Leu Ser Thr Gly Leu Ile His
                325                 330                 335

Leu His Gln Asn Ile Val Asp Val Gln Tyr Leu Tyr Gly Val Gly Ser
            340                 345                 350

Met Gly Trp Arg Leu Leu Ala Pro Ile Thr Ala Tyr Ala Gln Gln Thr
            355                 360                 365

Arg Gly Leu Leu Gly Thr Ile Val Thr Ser Leu Thr Gly Arg Asp Lys
            370                 375                 380

Asn Pro Cys Thr Cys Gly Ser Ser Asp Leu Tyr Leu Val Thr Arg His
385                 390                 395                 400

Ala Asp Val Ile Pro Val Arg Arg Gly Asp Ser Arg Gly Ser Leu
                405                 410                 415

Leu Ser Pro Arg Pro Ile Ser Tyr Leu Lys Gly Ser Ser Gly Gly Pro
            420                 425                 430

Val Leu Cys Pro Ser Gly His Ala Val Gly Ile Phe Arg Ala Ala Val
            435                 440                 445

Cys Thr Arg Gly Val Ala Lys Ala Val Asp Phe Ile Pro Val Glu Ser
450                 455                 460

Leu Glu Met Arg Ser Pro Val Phe Thr Asp Asn Ser Thr Pro Pro Ala
465                 470                 475                 480

Val Pro Gln Thr Tyr Gln Val Ala His Leu His Ala Pro Thr Gly Ser
            485                 490                 495

Gly Lys Ser Thr Lys Val Pro Ala Ala Tyr Ala Ala Gln Gly Tyr Lys
            500                 505                 510

Val Leu Val Leu Asn Pro Ser Val Ala Ala Thr Leu Gly Phe Gly Ala
            515                 520                 525

Tyr Met Ser Lys Ala Tyr Gly Ile Gly Gly Ser Arg Ser Gly Val Arg
530                 535                 540

Thr Ile Thr Thr Gly Ala Pro Ile Thr Tyr Ser Thr Tyr Gly Lys Phe
545                 550                 555                 560

Leu Ala Asp Gly Gly Cys Ser Gly Gly Ala Tyr Asp Ile Ile Ile Cys
                565                 570                 575

Asp Glu Cys His Ser Thr Asp Ser Thr Thr Ile Leu Gly Ile Gly Thr
            580                 585                 590

Val Leu Asp Gln Ala Glu Thr Ala Gly Val Arg Leu Val Val Leu Ala
            595                 600                 605

Thr Ala Thr Pro Pro Gly Gly Lys Gly Lys Gly Ile Lys Gly Gly
            610                 615                 620

Arg His Leu Ile Phe Cys His Ser Lys Lys Lys Cys Asp Glu Leu Ala
625                 630                 635                 640

Gly Pro Gly Asn Ala Val Ala Tyr Tyr Arg Gly Leu Asp Val Ser Val
                645                 650                 655

Ile Pro Thr Ser Gly Asp Val Val Val Ala Thr Asp Ala Leu Met
            660                 665                 670

Thr Gly Phe Thr Gly Asp Phe Asp Ser Val Ile Asp Cys Asn Thr Cys
```

-continued

```
            675                 680                 685
Val Thr Gln Thr Val Asp Phe Ser Leu Asp Pro Thr Phe Thr Ile Glu
        690                 695                 700

Thr Thr Thr Val Pro Gln Asp Ala Val Ser Arg Ser Gln Arg Arg Gly
705                 710                 715                 720

Arg Thr Gly Arg Gly Arg Arg Gly Ile Tyr Arg Phe Val Thr Pro Gly
                725                 730                 735

Glu Arg Pro Ser Gly Met Phe Asp Ser Ser Val Leu Cys Glu Cys Tyr
            740                 745                 750

Asp Ala Gly Cys Ala Trp Tyr Glu Leu Thr Pro Ala Glu Thr Ser Val
            755                 760                 765

Arg Leu Arg Ala Tyr Leu Asn Thr Pro Gly Leu Pro Val Cys Gln Asp
        770                 775                 780

His Leu Glu Phe Trp Glu Gly Val Phe Thr Gly Leu Thr His Ile Asp
785                 790                 795                 800

Ala His Phe Leu Ser Gln Thr Lys Gln Ala Gly Asp Asn Phe Pro Tyr
                805                 810                 815

Leu Val Ala Tyr Gln Ala Thr Val Cys Ala Arg Ala Gln Ala Pro Pro
            820                 825                 830

Pro Ser Trp Asp Gln Met Trp Thr His Pro Ile Thr Lys Tyr Ile Met
            835                 840                 845

Ala Cys Met Ser Ala Asp Leu Glu Val Val Thr Ser Thr Trp Val Leu
850                 855                 860

Val Gly Gly Val Leu Ala Ala Leu Ala Ala Tyr Cys Leu Ser Val Gly
865                 870                 875                 880

Ser Val Val Ile Val Gly Gly Pro Gly Phe Trp Ala Lys His Met Trp
                885                 890                 895

Asn Phe Ile Ser Gly Ile Gln Tyr Leu Ala Gly Leu Ser Thr Leu Pro
            900                 905                 910

Gly Asn Pro Ala Ile Ala Ser Leu Met Ala Phe Thr Ala Ala Val Thr
        915                 920                 925

Ser Pro Leu Gly Ala Ala Val Gly Ser Val Gly Leu Gly Lys Val Leu
    930                 935                 940

Val Asp Ile Leu Ala Gly Tyr Gly Ala Gly Val Ala Gly Ala Leu Val
945                 950                 955                 960

Ala Phe Lys Ile Met Ser Gly Glu Val Pro Ser Thr Glu Asp Leu Val
                965                 970                 975

Asn Leu Leu Pro Ala Ile Leu Ser Pro Gly Ala Leu Val Val Gly Val
            980                 985                 990

Val Cys Ala Ala Ile Leu Arg Arg His Val Gly Pro Gly Glu Gly Ala
        995                 1000                1005

Val Gln Trp Met Asn Arg Leu Ile Ala Phe Ala Ser Arg Gly Asn
    1010                1015                1020

His Val Ser Pro Thr His Tyr Val Pro Glu Ser Asp Ala Ala Ala
    1025                1030                1035

Arg Val Gly Pro Thr Ala Glu Thr Ala Ala Arg Arg Leu Ala Arg
    1040                1045                1050

Gly Ser Pro Pro Ser Leu Ala Ser Ser Ser Ala Ser Gln Leu Ser
    1055                1060                1065

Ala Pro Ser Leu Lys Ala Thr Cys Thr Val Cys Cys Ser Met Ser
    1070                1075                1080

Tyr Ser Trp Thr Gly Ala Leu Ile Thr Pro Cys Ala Ala Glu Glu
    1085                1090                1095
```

-continued

```
Glu Lys Leu Pro Ile Asn Pro Leu Ser Asn Ser Leu Ile Arg His
    1100            1105                1110

His Asn Met Val Tyr Ser Thr Thr Ser Arg Ser Ala Ser Leu Arg
    1115            1120                1125

Gln Lys Lys Val Thr Phe Asp Arg Gly Ser Gly Gly Pro Gly
    1130            1135                1140

Pro Ser Lys Gly Gly Arg Lys Pro Ala Arg Leu Ile Val Tyr Pro
    1145            1150                1155

Asp Leu Gly Val Arg Val Cys Glu Lys Arg Ala Leu Tyr Asp Val
    1160            1165                1170

Pro Gly Gly Pro Lys Lys Thr Pro Met Gly Phe Ser Tyr Asp Thr
    1175            1180                1185

Arg Cys Phe Asp Ser Thr Val Thr Glu Arg Asp Ile Arg Thr Glu
    1190            1195                1200

Gly Gly Gly Pro Gly Gly Cys Gly Tyr Arg Arg Cys Arg Ala Ser
    1205            1210                1215

Gly Val Leu Thr Thr Ser Met Gly Asn Thr Ile Thr Cys Tyr Ile
    1220            1225                1230

Lys Ala Leu Ala Ala Glu Ala Met Thr Arg Tyr Ser Ala Pro Pro
    1235            1240                1245

Gly Asp Pro Pro Gln Pro Glu Tyr Asp Leu Glu Leu Ile Thr Ser
    1250            1255                1260

Cys Ser Ser Asn Val Ser Val Ala His Asp Gly Gly Ser Gly Gly
    1265            1270                1275

Thr Pro Leu Ala Arg Ala Ala Trp Glu Thr Ala Arg His Thr Pro
    1280            1285                1290

Val Asn Ser Trp Leu Gly Asn Ile Ile Met Tyr Ala Pro Thr Ile
    1295            1300                1305

Trp Val Arg Met Val Leu Met Thr His Phe Phe Ser Ile Leu Gln
    1310            1315                1320

Gly Gly Pro Gly Tyr Gly Ala Thr Tyr Ser Val Thr Pro Leu Asp
    1325            1330                1335

Leu Pro Ala Ile Ile Glu Arg Leu His Gly Leu Ser Ala Phe Thr
    1340            1345                1350

Leu His Ser Tyr Ser Gly Gly Pro Gly Gly Pro Glu Leu Asn Arg
    1355            1360                1365

Val Gly Ala Cys Leu Arg Lys Leu Gly Val Pro Pro Leu Arg Ala
    1370            1375                1380

Trp Arg His Arg Ala Arg Ala Val Arg Ala Lys Leu Ile Ala Gln
    1385            1390                1395

Gly Gly Lys Ala Ala Ile Cys Gly Lys Tyr Leu Phe Asn Trp Ala
    1400            1405                1410

Val

<210> SEQ ID NO 126
<211> LENGTH: 180
<212> TYPE: PRT
<213> ORGANISM: Homo sapiens
<220> FEATURE:
<221> NAME/KEY: VARIANT
<222> LOCATION: (65)..(65)
<223> OTHER INFORMATION: X is T or S
<220> FEATURE:
<221> NAME/KEY: VARIANT
<222> LOCATION: (100)..(100)
<223> OTHER INFORMATION: X is T or N
```

```
<220> FEATURE:
<221> NAME/KEY: VARIANT
<222> LOCATION: (134)..(134)
<223> OTHER INFORMATION: X is L or V
<220> FEATURE:
<221> NAME/KEY: VARIANT
<222> LOCATION: (137)..(137)
<223> OTHER INFORMATION: X is A or V
<220> FEATURE:
<221> NAME/KEY: VARIANT
<222> LOCATION: (147)..(147)
<223> OTHER INFORMATION: X is V or A
<220> FEATURE:
<221> NAME/KEY: VARIANT
<222> LOCATION: (152)..(152)
<223> OTHER INFORMATION: X is V or I
<220> FEATURE:
<221> NAME/KEY: VARIANT
<222> LOCATION: (154)..(154)
<223> OTHER INFORMATION: X is Y or F
<220> FEATURE:
<221> NAME/KEY: VARIANT
<222> LOCATION: (177)..(177)
<223> OTHER INFORMATION: X is V or H

<400> SEQUENCE: 126

Thr Lys Arg Asn Thr Asn Arg Arg Pro Gln Asp Val Lys Phe Pro Gly
1               5                   10                  15

Gly Gly Gln Ile Val Gly Gly Val Tyr Leu Leu Pro Arg Arg Gly Pro
            20                  25                  30

Arg Leu Gly Val Arg Ala Thr Arg Lys Thr Ser Glu Arg Ser Gln Pro
        35                  40                  45

Arg Gly Arg Arg Gln Pro Ile Pro Lys Ala Arg Arg Pro Glu Gly Arg
    50                  55                  60

Xaa Trp Ala Gln Pro Gly Tyr Pro Trp Pro Leu Tyr Gly Asn Glu Gly
65                  70                  75                  80

Cys Gly Trp Ala Gly Trp Leu Leu Ser Pro Arg Gly Ser Arg Pro Ser
                85                  90                  95

Trp Gly Pro Xaa Asp Pro Arg Arg Ser Arg Asn Leu Gly Lys Val
            100                 105                 110

Ile Asp Thr Leu Thr Cys Gly Phe Ala Asp Leu Met Gly Tyr Ile Pro
            115                 120                 125

Leu Val Gly Ala Pro Xaa Gly Gly Xaa Ala Arg Ala Leu Ala His Gly
    130                 135                 140

Val Arg Xaa Leu Glu Asp Gly Xaa Asn Xaa Ala Thr Gly Asn Leu Pro
145                 150                 155                 160

Gly Cys Ser Phe Ser Ile Phe Leu Leu Ala Leu Leu Ser Cys Leu Thr
                165                 170                 175

Xaa Pro Ala Ser
            180

<210> SEQ ID NO 127
<211> LENGTH: 20
<212> TYPE: PRT
<213> ORGANISM: Homo sapiens

<400> SEQUENCE: 127

Val Cys Gly Pro Val Tyr Cys Phe Thr Pro Ser Pro Val Val Val Gly
1               5                   10                  15

Thr Thr Asp Arg
            20

<210> SEQ ID NO 128
```

```
<211> LENGTH: 21
<212> TYPE: PRT
<213> ORGANISM: Homo sapiens
<220> FEATURE:
<221> NAME/KEY: VARIANT
<222> LOCATION: (1)..(1)
<223> OTHER INFORMATION: X is R or K

<400> SEQUENCE: 128

Xaa Cys Gly Ser Gly Pro Trp Leu Thr Pro Arg Cys Leu Val Asp Tyr
1               5                   10                  15

Pro Tyr Arg Leu Trp
            20

<210> SEQ ID NO 129
<211> LENGTH: 39
<212> TYPE: PRT
<213> ORGANISM: Homo sapiens
<220> FEATURE:
<221> NAME/KEY: VARIANT
<222> LOCATION: (4)..(4)
<223> OTHER INFORMATION: X is W or L
<220> FEATURE:
<221> NAME/KEY: VARIANT
<222> LOCATION: (5)..(5)
<223> OTHER INFORMATION: X is Q or A
<220> FEATURE:
<221> NAME/KEY: VARIANT
<222> LOCATION: (6)..(6)
<223> OTHER INFORMATION: X is V or I
<220> FEATURE:
<221> NAME/KEY: VARIANT
<222> LOCATION: (13)..(13)
<223> OTHER INFORMATION: X is T or P

<400> SEQUENCE: 129

Thr Thr Glu Xaa Xaa Xaa Leu Pro Cys Ser Phe Thr Xaa Leu Pro Ala
1               5                   10                  15

Leu Ser Thr Gly Leu Ile His Leu His Gln Asn Ile Val Asp Val Gln
            20                  25                  30

Tyr Leu Tyr Gly Val Gly Ser
        35

<210> SEQ ID NO 130
<211> LENGTH: 33
<212> TYPE: PRT
<213> ORGANISM: Homo sapiens
<220> FEATURE:
<221> NAME/KEY: VARIANT
<222> LOCATION: (1)..(1)
<223> OTHER INFORMATION: X is Q or M or K
<220> FEATURE:
<221> NAME/KEY: VARIANT
<222> LOCATION: (22)..(22)
<223> OTHER INFORMATION: X is C or T
<220> FEATURE:
<221> NAME/KEY: VARIANT
<222> LOCATION: (24)..(24)
<223> OTHER INFORMATION: X is I or V

<400> SEQUENCE: 130

Xaa Gly Trp Arg Leu Leu Ala Pro Ile Thr Ala Tyr Ala Gln Gln Thr
1               5                   10                  15

Arg Gly Leu Leu Gly Xaa Ile Xaa Thr Ser Leu Thr Gly Arg Asp Lys
            20                  25                  30

Asn

<210> SEQ ID NO 131
```

<211> LENGTH: 80
<212> TYPE: PRT
<213> ORGANISM: Homo sapiens
<220> FEATURE:
<221> NAME/KEY: VARIANT
<222> LOCATION: (21)..(21)
<223> OTHER INFORMATION: X is V or A
<220> FEATURE:
<221> NAME/KEY: VARIANT
<222> LOCATION: (29)..(29)
<223> OTHER INFORMATION: X is G or A
<220> FEATURE:
<221> NAME/KEY: VARIANT
<222> LOCATION: (37)..(37)
<223> OTHER INFORMATION: X is I or L
<220> FEATURE:
<221> NAME/KEY: VARIANT
<222> LOCATION: (38)..(38)
<223> OTHER INFORMATION: X is S or A
<220> FEATURE:
<221> NAME/KEY: VARIANT
<222> LOCATION: (39)..(39)
<223> OTHER INFORMATION: X is Y or T
<220> FEATURE:
<221> NAME/KEY: VARIANT
<222> LOCATION: (48)..(48)
<223> OTHER INFORMATION: X is L or V
<220> FEATURE:
<221> NAME/KEY: VARIANT
<222> LOCATION: (55)..(55)
<223> OTHER INFORMATION: X is A or V
<220> FEATURE:
<221> NAME/KEY: VARIANT
<222> LOCATION: (56)..(56)
<223> OTHER INFORMATION: X is A or V
<220> FEATURE:
<221> NAME/KEY: VARIANT
<222> LOCATION: (72)..(72)
<223> OTHER INFORMATION: X is V or L
<220> FEATURE:
<221> NAME/KEY: VARIANT
<222> LOCATION: (73)..(73)
<223> OTHER INFORMATION: X is D or Q
<220> FEATURE:
<221> NAME/KEY: VARIANT
<222> LOCATION: (79)..(79)
<223> OTHER INFORMATION: X is S or T

<400> SEQUENCE: 131

Pro Cys Thr Cys Gly Ser Ser Asp Leu Tyr Leu Val Thr Arg His Ala
1               5                   10                  15

Asp Val Ile Pro Xaa Arg Arg Arg Gly Asp Ser Arg Xaa Ser Leu Leu
            20                  25                  30

Ser Pro Arg Pro Xaa Xaa Xaa Leu Lys Gly Ser Ser Gly Gly Pro Xaa
        35                  40                  45

Leu Cys Pro Ser Gly His Xaa Xaa Gly Ile Phe Arg Ala Ala Val Cys
    50                  55                  60

Thr Arg Gly Val Ala Lys Ala Xaa Xaa Phe Ile Pro Val Glu Xaa Leu
65                  70                  75                  80

<210> SEQ ID NO 132
<211> LENGTH: 66
<212> TYPE: PRT
<213> ORGANISM: Homo sapiens
<220> FEATURE:
<221> NAME/KEY: VARIANT
<222> LOCATION: (4)..(4)
<223> OTHER INFORMATION: X is V or S
<220> FEATURE:
<221> NAME/KEY: VARIANT
<222> LOCATION: (6)..(6)
<223> OTHER INFORMATION: X is T or S
<220> FEATURE:

```
<221> NAME/KEY: VARIANT
<222> LOCATION: (10)..(10)
<223> OTHER INFORMATION: X is S or T
<220> FEATURE:
<221> NAME/KEY: VARIANT
<222> LOCATION: (17)..(17)
<223> OTHER INFORMATION: X is T or S
<220> FEATURE:
<221> NAME/KEY: VARIANT
<222> LOCATION: (18)..(18)
<223> OTHER INFORMATION: X is F or Y
<220> FEATURE:
<221> NAME/KEY: VARIANT
<222> LOCATION: (21)..(21)
<223> OTHER INFORMATION: X is A or G

<400> SEQUENCE: 132

Arg Ser Pro Xaa Phe Xaa Asp Asn Ser Xaa Pro Pro Ala Val Pro Gln
1               5                   10                  15

Xaa Xaa Gln Val Xaa His Leu His Ala Pro Thr Gly Ser Gly Lys Ser
            20                  25                  30

Thr Lys Val Pro Ala Ala Tyr Ala Ala Gln Gly Tyr Lys Val Leu Val
        35                  40                  45

Leu Asn Pro Ser Val Ala Ala Thr Leu Gly Phe Gly Ala Tyr Met Ser
    50                  55                  60

Lys Ala
65

<210> SEQ ID NO 133
<211> LENGTH: 74
<212> TYPE: PRT
<213> ORGANISM: Homo sapiens
<220> FEATURE:
<221> NAME/KEY: VARIANT
<222> LOCATION: (3)..(3)
<223> OTHER INFORMATION: X is V or N
<220> FEATURE:
<221> NAME/KEY: VARIANT
<222> LOCATION: (6)..(6)
<223> OTHER INFORMATION: X is I or V
<220> FEATURE:
<221> NAME/KEY: VARIANT
<222> LOCATION: (11)..(11)
<223> OTHER INFORMATION: X is P or K
<220> FEATURE:
<221> NAME/KEY: VARIANT
<222> LOCATION: (42)..(42)
<223> OTHER INFORMATION: X is T or Q
<220> FEATURE:
<221> NAME/KEY: VARIANT
<222> LOCATION: (46)..(46)
<223> OTHER INFORMATION: X is S or T
<220> FEATURE:
<221> NAME/KEY: VARIANT
<222> LOCATION: (62)..(62)
<223> OTHER INFORMATION: X is A or V
<220> FEATURE:
<221> NAME/KEY: VARIANT
<222> LOCATION: (65)..(65)
<223> OTHER INFORMATION: X is V or T

<400> SEQUENCE: 133

Thr Gly Xaa Arg Thr Xaa Thr Thr Gly Ala Xaa Ile Thr Tyr Ser Thr
1               5                   10                  15

Tyr Gly Lys Phe Leu Ala Asp Gly Gly Cys Ser Gly Gly Ala Tyr Asp
            20                  25                  30

Ile Ile Ile Cys Asp Glu Cys His Ser Xaa Asp Ala Thr Xaa Ile Leu
        35                  40                  45

Gly Ile Gly Thr Val Leu Asp Gln Ala Glu Thr Ala Gly Xaa Arg Leu
```

```
                    50                  55                  60

Xaa Val Leu Ala Thr Ala Thr Pro Pro Gly
 65                  70

<210> SEQ ID NO 134
<211> LENGTH: 72
<212> TYPE: PRT
<213> ORGANISM: Homo sapiens
<220> FEATURE:
<221> NAME/KEY: VARIANT
<222> LOCATION: (12)..(12)
<223> OTHER INFORMATION: X is V or C
<220> FEATURE:
<221> NAME/KEY: VARIANT
<222> LOCATION: (33)..(33)
<223> OTHER INFORMATION: X is T or V
<220> FEATURE:
<221> NAME/KEY: VARIANT
<222> LOCATION: (34)..(34)
<223> OTHER INFORMATION: X is C or A
<220> FEATURE:
<221> NAME/KEY: VARIANT
<222> LOCATION: (36)..(36)
<223> OTHER INFORMATION: X is T or E
<220> FEATURE:
<221> NAME/KEY: VARIANT
<222> LOCATION: (48)..(48)
<223> OTHER INFORMATION: X is T or S
<220> FEATURE:
<221> NAME/KEY: VARIANT
<222> LOCATION: (54)..(54)
<223> OTHER INFORMATION: X is L or A
<220> FEATURE:
<221> NAME/KEY: VARIANT
<222> LOCATION: (62)..(62)
<223> OTHER INFORMATION: X is T or S

<400> SEQUENCE: 134

Ser Val Ile Pro Thr Ser Gly Asp Val Val Xaa Ala Thr Asp Ala
  1               5                  10                  15

Leu Met Thr Gly Phe Thr Gly Asp Phe Asp Ser Val Ile Asp Cys Asn
                 20                  25                  30

Xaa Xaa Val Xaa Gln Thr Val Asp Phe Ser Leu Asp Pro Thr Phe Xaa
             35                  40                  45

Ile Glu Thr Thr Thr Xaa Pro Gln Asp Ala Val Ser Arg Xaa Gln Arg
     50                  55                  60

Arg Gly Arg Thr Gly Arg Gly Arg
 65                  70

<210> SEQ ID NO 135
<211> LENGTH: 110
<212> TYPE: PRT
<213> ORGANISM: Homo sapiens
<220> FEATURE:
<221> NAME/KEY: VARIANT
<222> LOCATION: (3)..(3)
<223> OTHER INFORMATION: X is F or Y
<220> FEATURE:
<221> NAME/KEY: VARIANT
<222> LOCATION: (5)..(5)
<223> OTHER INFORMATION: X is T or S
<220> FEATURE:
<221> NAME/KEY: VARIANT
<222> LOCATION: (17)..(17)
<223> OTHER INFORMATION: X is S or V
<220> FEATURE:
<221> NAME/KEY: VARIANT
<222> LOCATION: (33)..(33)
<223> OTHER INFORMATION: X is T or Q
<220> FEATURE:
<221> NAME/KEY: VARIANT
```

```
<222> LOCATION: (62)..(62)
<223> OTHER INFORMATION: X is G or S
<220> FEATURE:
<221> NAME/KEY: VARIANT
<222> LOCATION: (81)..(81)
<223> OTHER INFORMATION: X is A or Q or G
<220> FEATURE:
<221> NAME/KEY: VARIANT
<222> LOCATION: (83)..(83)
<223> OTHER INFORMATION: X is E or L
<220> FEATURE:
<221> NAME/KEY: VARIANT
<222> LOCATION: (100)..(100)
<223> OTHER INFORMATION: X is Q or K
<220> FEATURE:
<221> NAME/KEY: VARIANT
<222> LOCATION: (108)..(108)
<223> OTHER INFORMATION: X is Q or E or T

<400> SEQUENCE: 135

Tyr Arg Xaa Val Xaa Pro Gly Glu Arg Pro Ser Gly Met Phe Asp Ser
1               5                   10                  15

Xaa Val Leu Cys Glu Cys Tyr Asp Ala Gly Cys Ala Trp Tyr Glu Leu
            20                  25                  30

Xaa Pro Ala Glu Thr Thr Val Arg Leu Arg Ala Tyr Leu Asn Thr Pro
        35                  40                  45

Gly Leu Pro Val Cys Gln Asp His Leu Glu Phe Trp Glu Xaa Val Phe
    50                  55                  60

Thr Gly Leu Thr His Ile Asp Ala His Phe Leu Ser Gln Thr Lys Gln
65                  70                  75                  80

Xaa Gly Xaa Asn Phe Pro Tyr Leu Val Ala Tyr Gln Ala Thr Val Cys
            85                  90                  95

Ala Arg Ala Xaa Ala Pro Pro Ser Trp Asp Xaa Met Trp
        100                 105                 110

<210> SEQ ID NO 136
<211> LENGTH: 39
<212> TYPE: PRT
<213> ORGANISM: Homo sapiens
<220> FEATURE:
<221> NAME/KEY: VARIANT
<222> LOCATION: (2)..(2)
<223> OTHER INFORMATION: X is T or A
<220> FEATURE:
<221> NAME/KEY: VARIANT
<222> LOCATION: (11)..(11)
<223> OTHER INFORMATION: X is V or T
<220> FEATURE:
<221> NAME/KEY: VARIANT
<222> LOCATION: (18)..(18)
<223> OTHER INFORMATION: X is V or L
<220> FEATURE:
<221> NAME/KEY: VARIANT
<222> LOCATION: (32)..(32)
<223> OTHER INFORMATION: X is T or V

<400> SEQUENCE: 136

Met Xaa Cys Met Ser Ala Asp Leu Glu Val Xaa Thr Ser Thr Trp Val
1               5                   10                  15

Leu Xaa Gly Gly Val Leu Ala Ala Leu Ala Ala Tyr Cys Leu Ser Xaa
            20                  25                  30

Gly Cys Val Val Ile Val Gly
            35

<210> SEQ ID NO 137
<211> LENGTH: 36
<212> TYPE: PRT
```

```
<213> ORGANISM: Homo sapiens
<220> FEATURE:
<221> NAME/KEY: VARIANT
<222> LOCATION: (28)..(28)
<223> OTHER INFORMATION: X is I or V

<400> SEQUENCE: 137

Phe Trp Ala Lys His Met Trp Asn Phe Ile Ser Gly Ile Gln Tyr Leu
1               5                   10                  15

Ala Gly Leu Ser Thr Leu Pro Gly Asn Pro Ala Xaa Ala Ser Leu Met
            20                  25                  30

Ala Phe Thr Ala
            35

<210> SEQ ID NO 138
<211> LENGTH: 105
<212> TYPE: PRT
<213> ORGANISM: Homo sapiens
<220> FEATURE:
<221> NAME/KEY: VARIANT
<222> LOCATION: (31)..(31)
<223> OTHER INFORMATION: X is S or G
<220> FEATURE:
<221> NAME/KEY: VARIANT
<222> LOCATION: (34)..(34)
<223> OTHER INFORMATION: X is V or L or K
<220> FEATURE:
<221> NAME/KEY: VARIANT
<222> LOCATION: (40)..(40)
<223> OTHER INFORMATION: X is L or M

<400> SEQUENCE: 138

Gly Ser Ile Gly Leu Gly Lys Val Leu Val Asp Ile Leu Ala Gly Tyr
1               5                   10                  15

Gly Ala Gly Val Ala Gly Ala Leu Val Ala Phe Lys Ile Met Xaa Gly
            20                  25                  30

Glu Xaa Pro Ser Thr Glu Asp Xaa Val Asn Leu Leu Pro Ala Ile Leu
            35                  40                  45

Ser Pro Gly Ala Leu Val Val Gly Val Val Cys Ala Ala Ile Leu Arg
        50                  55                  60

Arg His Val Gly Pro Gly Glu Gly Ala Val Gln Trp Met Asn Arg Leu
65                  70                  75                  80

Ile Ala Phe Ala Ser Arg Gly Asn His Val Ser Pro Thr His Tyr Val
                85                  90                  95

Pro Glu Ser Asp Ala Ala Ala Arg Val
            100                 105

<210> SEQ ID NO 139
<211> LENGTH: 29
<212> TYPE: PRT
<213> ORGANISM: Homo sapiens
<220> FEATURE:
<221> NAME/KEY: VARIANT
<222> LOCATION: (11)..(11)
<223> OTHER INFORMATION: X is L or E
<220> FEATURE:
<221> NAME/KEY: VARIANT
<222> LOCATION: (29)..(29)
<223> OTHER INFORMATION: X is T or Q

<400> SEQUENCE: 139

Arg Arg Leu Ala Arg Gly Ser Pro Pro Ser Xaa Ala Ser Ser Ser Ala
1               5                   10                  15

Ser Gln Leu Ser Ala Pro Ser Leu Lys Ala Thr Cys Xaa
            20                  25
```

```
<210> SEQ ID NO 140
<211> LENGTH: 26
<212> TYPE: PRT
<213> ORGANISM: Homo sapiens
<220> FEATURE:
<221> NAME/KEY: VARIANT
<222> LOCATION: (3)..(3)
<223> OTHER INFORMATION: X is Y or C
<220> FEATURE:
<221> NAME/KEY: VARIANT
<222> LOCATION: (19)..(19)
<223> OTHER INFORMATION: X is S or E
<220> FEATURE:
<221> NAME/KEY: VARIANT
<222> LOCATION: (20)..(20)
<223> OTHER INFORMATION: X is D or F
<220> FEATURE:
<221> NAME/KEY: VARIANT
<222> LOCATION: (21)..(21)
<223> OTHER INFORMATION: X is G or E
<220> FEATURE:
<221> NAME/KEY: VARIANT
<222> LOCATION: (22)..(22)
<223> OTHER INFORMATION: X is S or Q
<220> FEATURE:
<221> NAME/KEY: VARIANT
<222> LOCATION: (23)..(23)
<223> OTHER INFORMATION: X is W or V
<220> FEATURE:
<221> NAME/KEY: VARIANT
<222> LOCATION: (24)..(24)
<223> OTHER INFORMATION: X is S or E
<220> FEATURE:
<221> NAME/KEY: VARIANT
<222> LOCATION: (25)..(25)
<223> OTHER INFORMATION: X is T or S
<220> FEATURE:
<221> NAME/KEY: VARIANT
<222> LOCATION: (26)..(26)
<223> OTHER INFORMATION: X is V or Q

<400> SEQUENCE: 140

Glu Ser Xaa Ser Ser Met Pro Pro Leu Glu Gly Glu Pro Gly Asp Pro
1               5                   10                  15

Asp Leu Xaa Xaa Xaa Xaa Xaa Xaa Xaa Xaa
            20                  25

<210> SEQ ID NO 141
<211> LENGTH: 20
<212> TYPE: PRT
<213> ORGANISM: Homo sapiens
<220> FEATURE:
<221> NAME/KEY: VARIANT
<222> LOCATION: (11)..(11)
<223> OTHER INFORMATION: X is M or L
<220> FEATURE:
<221> NAME/KEY: VARIANT
<222> LOCATION: (14)..(14)
<223> OTHER INFORMATION: X is A or S
<220> FEATURE:
<221> NAME/KEY: VARIANT
<222> LOCATION: (16)..(16)
<223> OTHER INFORMATION: X is T or S

<400> SEQUENCE: 141

Leu Ser Asn Ser Leu Leu Arg His His Asn Xaa Val Tyr Xaa Thr Xaa
1               5                   10                  15

Ser Arg Ser Ala
            20

<210> SEQ ID NO 142
```

```
<211> LENGTH: 24
<212> TYPE: PRT
<213> ORGANISM: Homo sapiens
<220> FEATURE:
<221> NAME/KEY: VARIANT
<222> LOCATION: (8)..(8)
<223> OTHER INFORMATION: X is F or Y
<220> FEATURE:
<221> NAME/KEY: VARIANT
<222> LOCATION: (19)..(19)
<223> OTHER INFORMATION: X is M or R

<400> SEQUENCE: 142

Lys Pro Ala Arg Leu Ile Val Xaa Pro Asp Leu Gly Val Arg Val Cys
1               5                  10                  15

Glu Lys Xaa Ala Leu Tyr Asp Val
            20

<210> SEQ ID NO 143
<211> LENGTH: 23
<212> TYPE: PRT
<213> ORGANISM: Homo sapiens
<220> FEATURE:
<221> NAME/KEY: VARIANT
<222> LOCATION: (18)..(18)
<223> OTHER INFORMATION: X is S or Q or R
<220> FEATURE:
<221> NAME/KEY: VARIANT
<222> LOCATION: (22)..(22)
<223> OTHER INFORMATION: X is T or V

<400> SEQUENCE: 143

Pro Met Gly Phe Ser Tyr Asp Thr Arg Cys Phe Asp Ser Thr Val Thr
1               5                  10                  15

Glu Xaa Asp Ile Arg Xaa Glu
            20

<210> SEQ ID NO 144
<211> LENGTH: 29
<212> TYPE: PRT
<213> ORGANISM: Homo sapiens
<220> FEATURE:
<221> NAME/KEY: VARIANT
<222> LOCATION: (13)..(13)
<223> OTHER INFORMATION: X is T or P
<220> FEATURE:
<221> NAME/KEY: VARIANT
<222> LOCATION: (16)..(16)
<223> OTHER INFORMATION: X is C or M
<220> FEATURE:
<221> NAME/KEY: VARIANT
<222> LOCATION: (24)..(24)
<223> OTHER INFORMATION: X is L or I
<220> FEATURE:
<221> NAME/KEY: VARIANT
<222> LOCATION: (27)..(27)
<223> OTHER INFORMATION: X is S or T or L

<400> SEQUENCE: 144

Cys Gly Tyr Arg Arg Cys Arg Ala Ser Gly Val Leu Xaa Thr Ser Xaa
1               5                  10                  15

Gly Asn Thr Leu Thr Cys Tyr Xaa Lys Ala Xaa Ala Ala
            20                  25

<210> SEQ ID NO 145
<211> LENGTH: 16
<212> TYPE: PRT
<213> ORGANISM: Homo sapiens
<220> FEATURE:
<221> NAME/KEY: VARIANT
```

```
<222> LOCATION: (13)..(13)
<223> OTHER INFORMATION: X is P or A

<400> SEQUENCE: 145

Glu Ala Met Thr Arg Tyr Ser Ala Pro Pro Gly Asp Xaa Pro Gln Pro
1               5                   10                  15

<210> SEQ ID NO 146
<211> LENGTH: 36
<212> TYPE: PRT
<213> ORGANISM: Homo sapiens
<220> FEATURE:
<221> NAME/KEY: VARIANT
<222> LOCATION: (26)..(26)
<223> OTHER INFORMATION: X is F or Y
<220> FEATURE:
<221> NAME/KEY: VARIANT
<222> LOCATION: (30)..(30)
<223> OTHER INFORMATION: X is L or [0anc]Tr;;63<220> FEATURE:
<221> NAME/KEY: VARIANT
<222> LOCATION: (32)..(32)
<223> OTHER INFORMATION: X is A or V
<220> FEATURE:
<221> NAME/KEY: VARIANT
<222> LOCATION: (35)..(35)
<223> OTHER INFORMATION: X is I or V

<400> SEQUENCE: 146

Thr Pro Leu Ala Arg Ala Ala Trp Glu Thr Ala Arg His Thr Pro Val
1               5                   10                  15

Asn Ser Trp Leu Gly Asn Ile Ile Met Xaa Ala Pro Thr Xaa Trp Xaa
            20                  25                  30

Arg Met Xaa Leu
        35

<210> SEQ ID NO 147
<211> LENGTH: 24
<212> TYPE: PRT
<213> ORGANISM: Homo sapiens
<220> FEATURE:
<221> NAME/KEY: VARIANT
<222> LOCATION: (1)..(1)
<223> OTHER INFORMATION: X is E or T
<220> FEATURE:
<221> NAME/KEY: VARIANT
<222> LOCATION: (7)..(7)
<223> OTHER INFORMATION: X is Q or A
<220> FEATURE:
<221> NAME/KEY: VARIANT
<222> LOCATION: (10)..(10)
<223> OTHER INFORMATION: X is Q or E

<400> SEQUENCE: 147

Xaa Pro Leu Asp Leu Pro Xaa Ile Ile Xaa Arg Leu His Gly Leu Ser
1               5                   10                  15

Ala Phe Ser Leu His Ser Tyr Ser
            20

<210> SEQ ID NO 148
<211> LENGTH: 23
<212> TYPE: PRT
<213> ORGANISM: Homo sapiens
<220> FEATURE:
<221> NAME/KEY: VARIANT
<222> LOCATION: (2)..(2)
<223> OTHER INFORMATION: X is I or L
<220> FEATURE:
<221> NAME/KEY: VARIANT
<222> LOCATION: (7)..(7)
<223> OTHER INFORMATION: X is A or G
```

```
<220> FEATURE:
<221> NAME/KEY: VARIANT
<222> LOCATION: (14)..(14)
<223> OTHER INFORMATION: X is V or C

<400> SEQUENCE: 148

Glu Xaa Asn Arg Val Ala Xaa Cys Leu Arg Lys Leu Gly Xaa Pro Pro
1               5                   10                  15

Leu Arg Ala Trp Arg His Arg
            20

<210> SEQ ID NO 149
<211> LENGTH: 16
<212> TYPE: PRT
<213> ORGANISM: Homo sapiens

<400> SEQUENCE: 149

Gly Gly Arg Ala Ala Ile Cys Gly Lys Tyr Leu Phe Asn Trp Ala Val
1               5                   10                  15

<210> SEQ ID NO 150
<211> LENGTH: 64
<212> TYPE: PRT
<213> ORGANISM: Homo sapiens

<400> SEQUENCE: 150

Thr Lys Arg Asn Thr Asn Arg Arg Pro Gln Asp Val Lys Phe Pro Gly
1               5                   10                  15

Gly Gly Gln Ile Val Gly Gly Val Tyr Leu Leu Pro Arg Arg Gly Pro
            20                  25                  30

Arg Leu Gly Val Arg Ala Thr Arg Lys Thr Ser Glu Arg Ser Gln Pro
        35                  40                  45

Arg Gly Arg Arg Gln Pro Ile Pro Lys Ala Arg Arg Pro Glu Gly Arg
    50                  55                  60

<210> SEQ ID NO 151
<211> LENGTH: 34
<212> TYPE: PRT
<213> ORGANISM: Homo sapiens

<400> SEQUENCE: 151

Trp Ala Gln Pro Gly Tyr Pro Trp Pro Leu Tyr Gly Asn Glu Gly Cys
1               5                   10                  15

Gly Trp Ala Gly Trp Leu Leu Ser Pro Arg Gly Ser Arg Pro Ser Trp
            20                  25                  30

Gly Pro

<210> SEQ ID NO 152
<211> LENGTH: 33
<212> TYPE: PRT
<213> ORGANISM: Homo sapiens

<400> SEQUENCE: 152

Asp Pro Arg Arg Arg Ser Arg Asn Leu Gly Lys Val Ile Asp Thr Leu
1               5                   10                  15

Thr Cys Gly Phe Ala Asp Leu Met Gly Tyr Ile Pro Leu Val Gly Ala
            20                  25                  30

Pro

<210> SEQ ID NO 153
<211> LENGTH: 9
```

<212> TYPE: PRT
<213> ORGANISM: Homo sapiens

<400> SEQUENCE: 153

Ala Arg Ala Leu Ala His Gly Val Arg
1               5

<210> SEQ ID NO 154
<211> LENGTH: 22
<212> TYPE: PRT
<213> ORGANISM: Homo sapiens

<400> SEQUENCE: 154

Ala Thr Gly Asn Leu Pro Gly Cys Ser Phe Ser Ile Phe Leu Leu Ala
1               5                   10                  15

Leu Leu Ser Cys Leu Thr
            20

<210> SEQ ID NO 155
<211> LENGTH: 20
<212> TYPE: PRT
<213> ORGANISM: Homo sapiens

<400> SEQUENCE: 155

Val Cys Gly Pro Val Tyr Cys Phe Thr Pro Ser Pro Val Val Val Gly
1               5                   10                  15

Thr Thr Asp Arg
            20

<210> SEQ ID NO 156
<211> LENGTH: 20
<212> TYPE: PRT
<213> ORGANISM: Homo sapiens

<400> SEQUENCE: 156

Cys Gly Ser Gly Pro Trp Leu Thr Pro Arg Cys Leu Val Asp Tyr Pro
1               5                   10                  15

Tyr Arg Leu Trp
            20

<210> SEQ ID NO 157
<211> LENGTH: 26
<212> TYPE: PRT
<213> ORGANISM: Homo sapiens

<400> SEQUENCE: 157

Leu Pro Ala Leu Ser Thr Gly Leu Ile His Leu His Gln Asn Ile Val
1               5                   10                  15

Asp Val Gln Tyr Leu Tyr Gly Val Gly Ser
            20                  25

<210> SEQ ID NO 158
<211> LENGTH: 20
<212> TYPE: PRT
<213> ORGANISM: Homo sapiens

<400> SEQUENCE: 158

Gly Trp Arg Leu Leu Ala Pro Ile Thr Ala Tyr Ala Gln Gln Thr Arg
1               5                   10                  15

Gly Leu Leu Gly
            20

```
<210> SEQ ID NO 159
<211> LENGTH: 9
<212> TYPE: PRT
<213> ORGANISM: Homo sapiens

<400> SEQUENCE: 159

Thr Ser Leu Thr Gly Arg Asp Lys Asn
1               5

<210> SEQ ID NO 160
<211> LENGTH: 20
<212> TYPE: PRT
<213> ORGANISM: Homo sapiens

<400> SEQUENCE: 160

Pro Cys Thr Cys Gly Ser Ser Asp Leu Tyr Leu Val Thr Arg His Ala
1               5                   10                  15

Asp Val Ile Pro
            20

<210> SEQ ID NO 161
<211> LENGTH: 8
<212> TYPE: PRT
<213> ORGANISM: Homo sapiens

<400> SEQUENCE: 161

Leu Lys Gly Ser Ser Gly Gly Pro
1               5

<210> SEQ ID NO 162
<211> LENGTH: 15
<212> TYPE: PRT
<213> ORGANISM: Homo sapiens

<400> SEQUENCE: 162

Gly Ile Phe Arg Ala Ala Val Cys Thr Arg Gly Val Ala Lys Ala
1               5                   10                  15

<210> SEQ ID NO 163
<211> LENGTH: 45
<212> TYPE: PRT
<213> ORGANISM: Homo sapiens

<400> SEQUENCE: 163

His Leu His Ala Pro Thr Gly Ser Gly Lys Ser Thr Lys Val Pro Ala
1               5                   10                  15

Ala Tyr Ala Ala Gln Gly Tyr Lys Val Leu Val Leu Asn Pro Ser Val
            20                  25                  30

Ala Ala Thr Leu Gly Phe Gly Ala Tyr Met Ser Lys Ala
        35                  40                  45

<210> SEQ ID NO 164
<211> LENGTH: 30
<212> TYPE: PRT
<213> ORGANISM: Homo sapiens

<400> SEQUENCE: 164

Ile Thr Tyr Ser Thr Tyr Gly Lys Phe Leu Ala Asp Gly Gly Cys Ser
1               5                   10                  15

Gly Gly Ala Tyr Asp Ile Ile Ile Cys Asp Glu Cys His Ser
            20                  25                  30

<210> SEQ ID NO 165
```

```
<211> LENGTH: 15
<212> TYPE: PRT
<213> ORGANISM: Homo sapiens

<400> SEQUENCE: 165

Ile Leu Gly Ile Gly Thr Val Leu Asp Gln Ala Glu Thr Ala Gly
1               5                   10                  15

<210> SEQ ID NO 166
<211> LENGTH: 9
<212> TYPE: PRT
<213> ORGANISM: Homo sapiens

<400> SEQUENCE: 166

Val Leu Ala Thr Ala Thr Pro Pro Gly
1               5

<210> SEQ ID NO 167
<211> LENGTH: 11
<212> TYPE: PRT
<213> ORGANISM: Homo sapiens

<400> SEQUENCE: 167

Ser Val Ile Pro Thr Ser Gly Asp Val Val Val
1               5                   10

<210> SEQ ID NO 168
<211> LENGTH: 20
<212> TYPE: PRT
<213> ORGANISM: Homo sapiens

<400> SEQUENCE: 168

Ala Thr Asp Ala Leu Met Thr Gly Phe Thr Gly Asp Phe Asp Ser Val
1               5                   10                  15

Ile Asp Cys Asn
            20

<210> SEQ ID NO 169
<211> LENGTH: 11
<212> TYPE: PRT
<213> ORGANISM: Homo sapiens

<400> SEQUENCE: 169

Gln Thr Val Asp Phe Ser Leu Asp Pro Thr Phe
1               5                   10

<210> SEQ ID NO 170
<211> LENGTH: 10
<212> TYPE: PRT
<213> ORGANISM: Homo sapiens

<400> SEQUENCE: 170

Gln Arg Arg Gly Arg Thr Gly Arg Gly Arg
1               5                   10

<210> SEQ ID NO 171
<211> LENGTH: 11
<212> TYPE: PRT
<213> ORGANISM: Homo sapiens

<400> SEQUENCE: 171

Pro Gly Glu Arg Pro Ser Gly Met Phe Asp Ser
1               5                   10
```

```
<210> SEQ ID NO 172
<211> LENGTH: 15
<212> TYPE: PRT
<213> ORGANISM: Homo sapiens

<400> SEQUENCE: 172

Val Leu Cys Glu Cys Tyr Asp Ala Gly Cys Ala Trp Tyr Glu Leu
1               5                   10                  15

<210> SEQ ID NO 173
<211> LENGTH: 28
<212> TYPE: PRT
<213> ORGANISM: Homo sapiens

<400> SEQUENCE: 173

Pro Ala Glu Thr Thr Val Arg Leu Arg Ala Tyr Leu Asn Thr Pro Gly
1               5                   10                  15

Leu Pro Val Cys Gln Asp His Leu Glu Phe Trp Glu
            20                  25

<210> SEQ ID NO 174
<211> LENGTH: 18
<212> TYPE: PRT
<213> ORGANISM: Homo sapiens

<400> SEQUENCE: 174

Val Phe Thr Gly Leu Thr His Ile Asp Ala His Phe Leu Ser Gln Thr
1               5                   10                  15

Lys Gln

<210> SEQ ID NO 175
<211> LENGTH: 16
<212> TYPE: PRT
<213> ORGANISM: Homo sapiens

<400> SEQUENCE: 175

Asn Phe Pro Tyr Leu Val Ala Tyr Gln Ala Thr Val Cys Ala Arg Ala
1               5                   10                  15

<210> SEQ ID NO 176
<211> LENGTH: 8
<212> TYPE: PRT
<213> ORGANISM: Homo sapiens

<400> SEQUENCE: 176

Cys Met Ser Ala Asp Leu Glu Val
1               5

<210> SEQ ID NO 177
<211> LENGTH: 13
<212> TYPE: PRT
<213> ORGANISM: Homo sapiens

<400> SEQUENCE: 177

Gly Gly Val Leu Ala Ala Leu Ala Ala Tyr Cys Leu Ser
1               5                   10

<210> SEQ ID NO 178
<211> LENGTH: 27
<212> TYPE: PRT
<213> ORGANISM: Homo sapiens

<400> SEQUENCE: 178

Phe Trp Ala Lys His Met Trp Asn Phe Ile Ser Gly Ile Gln Tyr Leu
```

```
                1               5                   10                  15
Ala Gly Leu Ser Thr Leu Pro Gly Asn Pro Ala
            20                  25

<210> SEQ ID NO 179
<211> LENGTH: 8
<212> TYPE: PRT
<213> ORGANISM: Homo sapiens

<400> SEQUENCE: 179

Ala Ser Leu Met Ala Phe Thr Ala
1               5

<210> SEQ ID NO 180
<211> LENGTH: 30
<212> TYPE: PRT
<213> ORGANISM: Homo sapiens

<400> SEQUENCE: 180

Gly Ser Ile Gly Leu Gly Lys Val Leu Val Asp Ile Leu Ala Gly Tyr
1               5                   10                  15

Gly Ala Gly Val Ala Gly Ala Leu Val Ala Phe Lys Ile Met
            20                  25                  30

<210> SEQ ID NO 181
<211> LENGTH: 65
<212> TYPE: PRT
<213> ORGANISM: Homo sapiens

<400> SEQUENCE: 181

Val Asn Leu Leu Pro Ala Ile Leu Ser Pro Gly Ala Leu Val Val Gly
1               5                   10                  15

Val Val Cys Ala Ala Ile Leu Arg Arg His Val Gly Pro Gly Glu Gly
            20                  25                  30

Ala Val Gln Trp Met Asn Arg Leu Ile Ala Phe Ala Ser Arg Gly Asn
        35                  40                  45

His Val Ser Pro Thr His Tyr Val Pro Glu Ser Asp Ala Ala Ala Arg
    50                  55                  60

Val
65

<210> SEQ ID NO 182
<211> LENGTH: 10
<212> TYPE: PRT
<213> ORGANISM: Homo sapiens

<400> SEQUENCE: 182

Arg Arg Leu Ala Arg Gly Ser Pro Pro Ser
1               5                   10

<210> SEQ ID NO 183
<211> LENGTH: 17
<212> TYPE: PRT
<213> ORGANISM: Homo sapiens

<400> SEQUENCE: 183

Ala Ser Ser Ser Ala Ser Gln Leu Ser Ala Pro Ser Leu Lys Ala Thr
1               5                   10                  15

Cys

<210> SEQ ID NO 184
```

```
<211> LENGTH: 15
<212> TYPE: PRT
<213> ORGANISM: Homo sapiens

<400> SEQUENCE: 184

Ser Ser Met Pro Pro Leu Glu Gly Glu Pro Gly Asp Pro Asp Leu
1               5                   10                  15

<210> SEQ ID NO 185
<211> LENGTH: 9
<212> TYPE: PRT
<213> ORGANISM: Homo sapiens

<400> SEQUENCE: 185

Leu Ser Asn Ser Leu Leu Arg His His
1               5

<210> SEQ ID NO 186
<211> LENGTH: 10
<212> TYPE: PRT
<213> ORGANISM: Homo sapiens

<400> SEQUENCE: 186

Pro Asp Leu Gly Val Arg Val Cys Glu Lys
1               5                   10

<210> SEQ ID NO 187
<211> LENGTH: 17
<212> TYPE: PRT
<213> ORGANISM: Homo sapiens

<400> SEQUENCE: 187

Pro Met Gly Phe Ser Tyr Asp Thr Arg Cys Phe Asp Ser Thr Val Thr
1               5                   10                  15

Glu

<210> SEQ ID NO 188
<211> LENGTH: 12
<212> TYPE: PRT
<213> ORGANISM: Homo sapiens

<400> SEQUENCE: 188

Cys Gly Tyr Arg Arg Cys Arg Ala Ser Gly Val Leu
1               5                   10

<210> SEQ ID NO 189
<211> LENGTH: 12
<212> TYPE: PRT
<213> ORGANISM: Homo sapiens

<400> SEQUENCE: 189

Glu Ala Met Thr Arg Tyr Ser Ala Pro Pro Gly Asp
1               5                   10

<210> SEQ ID NO 190
<211> LENGTH: 25
<212> TYPE: PRT
<213> ORGANISM: Homo sapiens

<400> SEQUENCE: 190

Thr Pro Leu Ala Arg Ala Ala Trp Glu Thr Ala Arg His Thr Pro Val
1               5                   10                  15

Asn Ser Trp Leu Gly Asn Ile Ile Met
            20                  25
```

<210> SEQ ID NO 191
<211> LENGTH: 14
<212> TYPE: PRT
<213> ORGANISM: Homo sapiens

<400> SEQUENCE: 191

Arg Leu His Gly Leu Ser Ala Phe Ser Leu His Ser Tyr Ser
1               5                   10

<210> SEQ ID NO 192
<211> LENGTH: 9
<212> TYPE: PRT
<213> ORGANISM: Homo sapiens

<400> SEQUENCE: 192

Pro Pro Leu Arg Ala Trp Arg His Arg
1               5

<210> SEQ ID NO 193
<211> LENGTH: 16
<212> TYPE: PRT
<213> ORGANISM: Homo sapiens

<400> SEQUENCE: 193

Gly Gly Arg Ala Ala Ile Cys Gly Lys Tyr Leu Phe Asn Trp Ala Val
1               5                   10                  15

<210> SEQ ID NO 194
<211> LENGTH: 32
<212> TYPE: PRT
<213> ORGANISM: Homo sapiens

<400> SEQUENCE: 194

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

<210> SEQ ID NO 195
<211> LENGTH: 27
<212> TYPE: PRT
<213> ORGANISM: Homo sapiens

<400> SEQUENCE: 195

Ser Leu Leu Trp Gly Gly Val Thr Val Leu Ala Ala Met Leu Ile Ala
1               5                   10                  15

Gly Gln Val Ala Ser Ser Val Val Phe Leu Val
                20                  25